(12) United States Patent
Li

(10) Patent No.: US 11,311,607 B2
(45) Date of Patent: *Apr. 26, 2022

(54) METHOD FOR MAKING GLUCAGON AND INSULIN RESTORE NORMAL BALANCE

(71) Applicant: Talengen International Limited, Wanchai (HK)

(72) Inventor: Jinan Li, Shenzhen (CN)

(73) Assignee: Talengen International Limited, Wanchai (HK)

( * ) Notice: Subject to any disclaimer, the term of this patent is extended or adjusted under 35 U.S.C. 154(b) by 415 days.

This patent is subject to a terminal disclaimer.

(21) Appl. No.: 16/469,817

(22) PCT Filed: Jun. 19, 2017

(86) PCT No.: PCT/CN2017/089066
§ 371 (c)(1),
(2) Date: Jun. 14, 2019

(87) PCT Pub. No.: WO2018/107706
PCT Pub. Date: Jun. 21, 2018

(65) Prior Publication Data
US 2019/0314463 A1 Oct. 17, 2019

Related U.S. Application Data

(63) Continuation of application No. PCT/CN2016/110171, filed on Dec. 15, 2016.

(30) Foreign Application Priority Data

Dec. 15, 2016 (WO) ................ PCT/CN2016/110171

(51) Int. Cl.
| *A61K 38/48* | (2006.01) |
| *A61P 3/10* | (2006.01) |
| *A61K 45/06* | (2006.01) |
| *A61P 3/04* | (2006.01) |
| *A61K 38/43* | (2006.01) |
| *A61P 5/50* | (2006.01) |

(52) U.S. Cl.
CPC ............ *A61K 38/484* (2013.01); *A61K 38/43* (2013.01); *A61K 38/48* (2013.01); *A61K 45/06* (2013.01); *A61P 3/04* (2018.01); *A61P 3/10* (2018.01); *A61P 5/50* (2018.01); *C12Y 304/21007* (2013.01)

(58) Field of Classification Search
CPC .. A61K 38/484; A61K 38/404; C12N 9/6435; C12Y 304/21007; A61P 3/10
See application file for complete search history.

(56) References Cited

U.S. PATENT DOCUMENTS

| 4,996,050 A | 2/1991 | Tsukada et al. |
| 5,637,299 A | 6/1997 | McDonagh et al. |
| 6,733,750 B1 | 5/2004 | Peyman |
| 11,090,372 B2 | 8/2021 | Li |
| 11,129,880 B2 | 9/2021 | Li |
| 2002/0159992 A1 | 10/2002 | Henkin et al. |
| 2003/0002679 A1 | 2/2003 | Zimmerman et al. |
| 2003/0026798 A1 | 2/2003 | Zimmerman et al. |
| 2003/0113313 A1 | 6/2003 | Peyman |
| 2003/0014787 P1 | 8/2003 | Ni et al. |
| 2003/0147876 A1 | 8/2003 | Ni et al. |
| 2003/0018093 A1 | 9/2003 | Ni et al. |
| 2003/0175263 A1 | 9/2003 | Trese et al. |
| 2003/0180934 A1 | 9/2003 | Ni et al. |
| 2005/0025069 A1 | 11/2005 | Ma |
| 2005/0250694 A1 | 11/2005 | Ma |
| 2006/0234913 A1 | 10/2006 | Arbit et al. |
| 2007/0019635 A1 | 8/2007 | Bartels |
| 2007/0185017 A1 | 8/2007 | Aggarwal et al. |
| 2007/0196350 A1 | 8/2007 | Bartels |
| 2009/0208448 A1 | 8/2009 | Solomon et al. |
| 2013/0273028 A1 | 10/2013 | Zwaal |
| 2018/0369345 A1 | 12/2018 | Li |
| 2019/0015485 A1 | 1/2019 | Li |
| 2019/0307861 A1 | 10/2019 | Li |
| 2019/0314464 A1 | 10/2019 | Li |
| 2019/0314465 A1 | 10/2019 | Li |
| 2021/0154275 A1 | 5/2021 | Li |

FOREIGN PATENT DOCUMENTS

| CA | 2145841 A1 | 10/1995 |
| CA | 3002915 A1 | 5/2017 |
| CN | 1195375 A | 10/1998 |
| CN | 1451746 A | 10/2003 |
| CN | 1543456 A | 11/2004 |
| CN | 1549814 A | 11/2004 |

(Continued)

OTHER PUBLICATIONS

NCBI Blast search resullts for SEQ ID No. 2 1pg, 2021 (Year: 2021).*
Alicic, et al., "Diabetic Kidney Disease Challenges, Progress, and Possibilities", Clin J Am Soc Nephrol 12: 2032-2045 (2017).
Bhattacharya, et al., "Impact of genetic variation on three dimensional structure and function of proteins", PLOS ONE 12(3): 1-22 (2017).
Dyck, et al., "The prevalence by staged severity of various types of diabetic neuropathy, retinopathy, and nephropathy in a population-based cohort:The Rochester Diabetic Neuropathy Study", Neurology 43:817-824 (1993).
Feuerstein, et al., "Cardioprotection and Thrombolysis by Anistreplase in Anesthetized Dogs", Journal of Cardiovascular Pharmacology vol. 25. No. 4. 625-633 (1995).

(Continued)

*Primary Examiner* — Thane Underdahl
(74) *Attorney, Agent, or Firm* — Nelson Mullins Riley & Scarborough LLP; Jill Gorny Sloper, Esq.

(57) ABSTRACT

The present invention relates to a method for restoring a balance between glucagon and insulin to normal, comprising administering an effective amount of plasminogen to a subject; furthermore, the present invention relates to a medicament for restoring a balance between glucagon and insulin to normal.

18 Claims, 13 Drawing Sheets

Specification includes a Sequence Listing.

(56) References Cited

FOREIGN PATENT DOCUMENTS

| | | | |
|---|---|---|---|
| CN | 1585649 A | 2/2005 | |
| CN | 1191856 C | 3/2005 | |
| CN | 1643140 A | 7/2005 | |
| CN | 1768138 A | 5/2006 | |
| CN | 1856319 A | 11/2006 | |
| CN | 1946352 A | 4/2007 | |
| CN | 1961958 A | 5/2007 | |
| CN | 1990871 A | 7/2007 | |
| CN | 101002888 A | 7/2007 | |
| CN | 101039936 A | 9/2007 | |
| CN | 101044136 A | 9/2007 | |
| CN | 101171030 A | 4/2008 | |
| CN | 101227918 A | 7/2008 | |
| CN | 101263115 A | 9/2008 | |
| CN | 101563100 A | 10/2009 | |
| CN | 101573134 A | 11/2009 | |
| CN | 101918548 A | 12/2010 | |
| CN | 102121023 A | 7/2011 | |
| CN | 102154253 A | 8/2011 | |
| CN | 102250210 A | 11/2011 | |
| CN | 102482338 A | 5/2012 | |
| CN | 102872020 A | 1/2013 | |
| CN | 103384722 A | 11/2013 | |
| CN | 103764163 A | 4/2014 | |
| CN | 104789544 A | 7/2015 | |
| CN | 105008323 A | 10/2015 | |
| CN | 105705520 A | 6/2016 | |
| EP | 0307847 A2 | 3/1989 | |
| EP | 0674906 A2 | 10/1995 | |
| EP | 3395359 A1 | 10/2018 | |
| EP | 3395360 A1 | 10/2018 | |
| EP | 3556391 A1 | 10/2019 | |
| JP | 2002510209 A | 4/2002 | |
| JP | 2005525798 A | 9/2005 | |
| JP | 2007533327 A | 11/2007 | |
| JP | 2009196927 A | 9/2009 | |
| JP | 2019500422 A | 1/2019 | |
| JP | 2020502140 A | 1/2020 | |
| JP | 2020502150 A | 1/2020 | |
| JP | 2020502151 A | 1/2020 | |
| JP | 2020510628 A | 4/2020 | |
| TW | 200803890 A | 1/2008 | |
| TW | 201625294 A | 7/2016 | |
| TW | 201822800 A | 7/2018 | |
| TW | 201822801 A | 7/2018 | |
| TW | 201822802 A | 7/2018 | |
| TW | 201822803 A | 7/2018 | |
| TW | 201822804 A | 7/2018 | |
| TW | 201822807 A | 7/2018 | |
| TW | 201822808 A | 7/2018 | |
| WO | 95/12407 A1 | 5/1995 | |
| WO | 9900420 A1 | 1/1999 | |
| WO | 0018436 A1 | 4/2000 | |
| WO | 0044391 A2 | 8/2000 | |
| WO | 03033019 A2 | 4/2003 | |
| WO | 2004052228 A2 | 6/2004 | |
| WO | 2006122249 A2 | 11/2006 | |
| WO | 2007051314 A1 | 5/2007 | |
| WO | 2008026999 A2 | 3/2008 | |
| WO | 2010111271 A1 | 9/2010 | |
| WO | 2010125148 A2 | 11/2010 | |
| WO | 2014070983 A1 | 5/2014 | |
| WO | 2017077380 A1 | 5/2017 | |
| WO | WO-2017077380 A1 * | 5/2017 | ........... C12N 9/6435 |

OTHER PUBLICATIONS

Fowler, "Diabetes Treatment: Insulin and Incretins", Clinical Diabetes, vol. 28 177-182 (2010).

Gao, et al., "Difference in Ischemic Regulation of Vascular Endothelial Growth Factor and Pigment Epithelium-Derived Factor in Brown Norway and Sprague Dawley Rats Contributing to Different Susceptibilities to Retinal Neovascularization", Diabetes, vol. 51 1218-1225 (2002).

Gattinoni, et al., "Adoptive immunotherapy for cancer: building on success", NIH Public Access, Nat Rev Immunol. 6(5): 383-393 (2006).

Izenberg, et al., "Diabetic Neuropathies", Semin Neurol 35: 424-430 (2015).

Ma, et al., "Genetic variants in PLG, LPA, and SIGLEC 14 as well as smoking contribute to plasma plasminogen levels", Blood, vol. 124, No. 20 3155-3164 (2014).

Martin-Femandez, et al., "The Unravelling of the Genetic Architecture of Plasminogen Deficiency and its Relation to Thrombotic Disease", Scientific Reports 6:39255 DOI: 10.1038/srep39255 1-7 (2016).

Mayo Clinic, "Heart attack", https://www.mayoclinic.org/diseases-conditions/heart-attack/symptoms-causes/syc-20373106 4 pages, (1998).

Naito Gen, "The Formulation and Clinical Experience of Plasminogen Activator System", English abstract, Journal of Japan Society of the Blood Transfusion vol. 32. No. 5 590-592.

Pinkney, et al., "Endothelial Dysfunction: Cause of the Insulin Resistance Syndrome", Diabetes, vol. 46 S9-S13 (1997).

Robertson, et al., "Pancreatic islet β-cell and oxidative stress: The importance of glutathione peroxidase", FEBS Letters 581 3743-3748 (2007).

Science Daily, "How Diabetes Drives Atherosclerosis", University of Rochester Medical Center, https://www.sciencedaily.com/releases/2008/03/080313124430.htm, 2 pages (2008).

Williams, Mark E., "Diabetic Nephropathy", Am J Nephrol 25:77-94 (2005).

Zhongming, et al., "Effects of Plasmin Capsules On Antioxidation and Endothelial Function", English abstract, The 41st Hospital of PLA, China Academic Journal Electronic Publishing House: 33-35 (2002).

Zhang, Y. et al., "Fibrinolytic activity and type 2 diabetes mellitus and macroangiopathy thereof" Section of Endocrinology Foreign Medical Sciences?vol. 25, 1 page, Abstract only, (2005).

Zhao Y. et al., "Clinical observation of 36 cases of progressive cerebral infarction treated with plasmin," Journal of Nother Sichuan Medical College, vol. 22(6): 3pages (2007).

Zhou H., et al., "Fibrinolytic Enzyme Assisted Therapy for 62 Cases of Type 2 Diabetes Mellitus," Herald of Medicine, vol. 30:35-36 (2011).

Zou, T. et al., "Exogenous tissue plasminogen activator enhances peripheral nerve regeneration and function recovery after injury in mice," J Neuropathol Exp Neurol, vol. 65(1):78-86 (2006).

U.S. Appl. No. 16/470,120, filed Nov. 18, 2020.

Aisina, R.B. et al., "Structure and function of plasminogen/plasmin system," Russian Journal of Bioorganic Chemistry, vol. 40(6): 590-605 (2014).

Ling X. et al., "Diabetic angiopathy and angiogenic defects," Fibrogenisis & Tissue Repair, Biomed Central Ltd., vol. 5(1): 9 pages (2012).

Sun Yuee et al., "Advancement on thrombolytic characteristic, function and clinical application of different fibrinolytic enzymes," China Journal of Chinese Materia Medica, vol. 35(6):794-798 (2010).

Abe, T. "Progress of Thrombolytic Therapy and its clinical Effect," Blood and Vessel, vol. 12(4):493-550 (1981).

Ajjan, R. et al. "Diabetes is associated with posttranslational modifications in plasminogen resulting in reduced plasmin generation and enzyme-specific activity," Blood, vol. 122(1):134-142 (2013).

Akassoglou, K. et al, "Tissue Plasminogen Activator-mediated Fibrinolysis Protects Against Axonal Degeneration and Demyelination after Sciatic Nerve Injury" J Cell Biol, vol. 149(5):1157-1166 (2000).

Auwerx, J. "Tissue-type plasminogen activator antigen and plasminogen activator inhibitor," Arteriosclerosis, Thrombosis and Vascular Biology, vol. 8: 68-72 (1988).

Brazionis, L. et al., "Plasminogen Activator Inhibitor-1 Activity in Type 2 Diabetes: A Different Relationship With Coronary Heart Disease and Diabetic Retinopathy", Arterioscler Thromb Vase Biol., vol. 28:786-791(2008).

(56) References Cited

OTHER PUBLICATIONS

Butera, D. et al, "Plasminogen isoform 1 precursor", GenBank, NP-000292.1, 8 pages (2015).

Chang, P.C. et al., "Human plasminogen kringle 1-5 reduces atherosclerosis and neointima formation in mice by suppressing the inflammatory signaling pathway," Journal of Thrombosis and Haemostasis, vol. 8(1): 194-201 (2010).

Chen W, "Pilot Production and Pharmacodynamics study of Recombinant Human Microplasminogen" Fudan University?Biochemistry and Molecular Biology, 98 pages (2007).

Chen, Y. et al., "The pathologic mechanism of diabetic retinopathy," International Journal of Ophthalmology, vol. 6 (2):3 pages (2006).

Du, Z. et al., "Changes of Plasma tPA and PAI Activities in Patients with Diabetic Retinopathy," Eye Science. vol. 13 (1):17-20 (1997).

Fisher, E. et al., "Displacement of Tissue Bound Plasminogen by; Glucose: A possible Mechanism m the Pathogenesis of Diabetic Nephropathy," Endocrinology and Metabolism. vol. 4: 371-376 (1997).

Gao, C. et al., "Relationship between Type Diabetic Retinopathy and Plasma Fibrinolysis" Progress in Modern Biomedicine, vol. 7(2): 257-258 (2007).

Gutiérrez-Fernández, A. et al, "Plasminogen Enhances Neuritogenesis on Laminin-1," J Neurosci, vol. 29(40): 12393-12400 (2009).

Hafer-Macko, C. E. et al, "Microvascular tissue plasminogen activator is reduced in diabetic neuropathy", Neurology, vol. 69: 268-274 (2007 ).

Hou X. et al., "Effect of insulin pump therapy on type 2 diabetes mellitus on glucose and lipid metabolism and plasminogen," Journal of Heze Medical College, vol. 24(1):2 pages (2012).

Jin X., et al. "Effect of kallidinogenase in treatment of diabetic nephropathy" Chinese Journal of Coal Industry Medicine, vol. 5(8): 825-826 (2002).

Kanno, Y et al., "Plasminogen/Plasmin Modulates Bone Metabolism by Regulating the Osteoblast and Osteoclast Function," J Biol Chem., vol. 286(11): 8952-60 (2011).

Kenichi, M., et al, "Renal synthesis of urokinase type-plasminogen activator, its receptor, and plasminogen activator inhibitor-1 in diabetic nephropathy in rats: Modulation by angiotensin-converting-enzyme inhibitor," Journal of Laboratory and Clinical Medicine, vol. 144 (2): 69-77 (2004).

Knudsen, B.S. et al. "Binding of Plasminogen to Extracellular Matrix," The Journal of Biological Chemistry, vol. 261 (23):10765-10771 (1986).

Koyoshi, A., et al, "Diabetes And Peripheral Neuropathy", Journal of the Japan Society of Internal Medicine, vol. 98 (2):399-405 (2009).

Lee, H. B. et al., Plasminogen Activator Inhibitor-I and Diabetic Nephropathy Nephrology, vol. 10:SI1-SI3 (2005).

Li, J. et al., "Catabolic Enzymes of Extracellular Matrix and Diatetic Nephropathy," Medical Recapitulate, vol. 14 (17):2610-2613 (2008).

Li, Q. et al, "Research progress on the pathogenesis of diabetic cardiomyopathy," Chinese Journal of General Practice, vol. 9(2): 291-292(2011).

Liu C. et al, "Comparision of the Affect of gumepiride and metformin on fibrinolytic function in patients Newly Diagnosed Type 2 Diabetes Mellitus," Modern Hospital, vol. 12: 2 pages (2012).

Lugea, A. et al., "Pancreas Recovery Following Caerulein-induced Pancreatitis is Impaired in Plasminogen Deficient Mice," Gastroenterology, vol. 131(3):885-899 (2006).

Ma, L.J., et al., "Prevention of obesity and insulin resistance in mice lacking plasminogen activator inhibitor 1", Diabetes, vol. 53(2):336-346 (2004).

Miles, LA. et al, "The Plasminogen Receptor, Plg-RKT, Regulates Metabolic Homeostasis and Promotes Healthy Adipose Function," Circulation, Abstract No. A19088, vol. 134 (Issue Suppl 1): 5 pages (2016).

Mirsky, A. et al. "The destruction of glucagon, adrenocorticotropin and somatotropin by human blood plasma" J . Clin. Invest., vol. 28:14-20 (1959).

Nicholas, SB. et al, "Plasminogen activator inhibitor-1 deficiency retards diabetic nephropathy," Kidney International, vol. 67(4): 1297-1307(2005).

Plow, E.F. et al., "The Functions of Plasminogen in Cardiovascular Disease", Trends Cardiovasc Med., vol. 14 (5): 180-186 (2004).

Polat, S. et al, "Evaluation of Serum Fibrinogen, Plasminogen, alpha2-Anti-Plasmin, and Plasminogen Activator Inhibitor Levels (PAI) and Their Correlation with Presence of Retinopathy in Patients with Type 1 DM ," Journal of Diabetes Research, vol. 2014:Article ID 317292, 6 pages (2014).

Romagnolol, Z. et al. "plasminogen isoform 1 precursor [Homo sapiens]," NCBI Reference Sequence: NP_000292.1, 8 pages, Mar. 24, 1999.

Schott, D. et al., Therapy with A Purified Plasminogen Concentrate in an Infant with Ligneous Conjunctivitis and Homozygous Plasminogen Deficiency, The New England Journal of Medicine, vol. 339(23): 1679-1686 (1998).

Shen, Y. et al., "Plasminogen is a Key Proinflammatory Regulator that Accelerates the Healing of Acute and Diabetic Wounds," Blood., vol. 119 (24):5879-5887 (2012).

Shi, L. et al., "Comparison of Curative Effects of Kallidinogenase between Patients with Early Diabetic Nephropathy and Patients with Clinical Diabetic Nephropathy," Journal of Jilin University (Medicine Edition), vol. 31(6): 934-936 (2005).

Siconolfi, L. B. et al, "Mice Lacking tPA, uPA, or Plasminogen Genes Showed Delayed Functional Recovery after Sciatic Nerve Crush" J Neurosci, vol. 21(12): 4348-4355 (2001).

Sima, J. et al, "The effect of angiostatin on vascular leakage and VEGF expression in rat retina," FEBS Letters, vol. 564: 19-23 (2004).

Singh, R. et al. "Diabetic peripheral neuropathy: Current perspective and future directions." Pharmacological Research , vol. 80:21-35 (2014).

Tsuchida I., et al.,"Effect of urokinase on heart and brain infarctions combined with diabetic patients," Clinical and research , vol. 58(2):659-665 (1981).

Wang, Q. "Rest and Protection of Pancreatic Islet Beta-cell," Chinese Nursing Research, vol. 19(9A): 1706-1708 (2005).

Wang, X., "Medical treatment of painful diabetic neuropathy" Journal of Community Medicine, vol. 12 (6): 82-83 (2014).

Wenku, B. Study on the pathogenesis of diabetic cardiomyopathy (DC), 10 pages, Apr. 26, 2011.

Xu, A. et al. "New progress in the treatment of diabetic neuropathic pain" Chinese Journal of Clinical Research, vol. 27 (2): 227-230 (2014).

Xu, D., "Therapeutic effect of recombinant tissue plasminogen activator on acute cerebral infarction," Prevention and Treatment of Cardio-Cerebral-Vascular Disease, vol. 12 (1): 37-39 (2012).

Yan X. et al, "Beta cell function in relation to plasminogen activator inhibitor-1 and tissue-plasminogen activator in postmenopausal females with different glucose tolerance," Chin J Hypertens, Nov. 30, 2013, vol. 21(11): 4 pages (2013).

Yang L., et al. "Changes of Fibrinolytic Parameters in Coronary Heart Disease" Chinese Journal of Thrombosis and Hemostasis, vol. 10 (1):8-10 (2004).

Yin, G. et al, "Cloning Construction and Purification of Recombinant Human Plasminogen Kringle 5 Gene", Academic Journal of Shanghai Second Medical University, vol. 25 (2): 151-154.

Zhang Y. et al, "Relationship between fibrinolysis change and insulin resistance in type 2 diabetes mellitus with microangiopathy," Clinical Focus, vol. 23 (6):3 pages (2018).

Zhang, S. et al., "Therapeutic Potential of Angiostatin in Diabetic Nephropathy," Journal of the American Society of Nephrology, vol. 17(2):475-486 (2006).

Zhang, S.X., et al., "Plasminogen kringle 5 reduces vascular leakage in the retina in rat models of oxygen-induced retinopathy," Diabetologia, vol. 47(1):124-131 (2004).

U.S. Appl. No. 16/954,159, filed Jun. 15, 2020, Jinan Li.
U.S. Appl. No. 16/062,037, filed Jun. 13, 2018, Jinan Li.
U.S. Appl. No. 16/062,049, filed Jun. 13, 2018, Jinan Li.
U.S. Appl. No. 16/470,120, filed Apr. 15, 2021.
U.S. Appl. No. 16/062,037, filed Jun. 10, 2021.
U.S. Appl. No. 16/062,037, filed Jan. 1, 2021.

(56) References Cited

OTHER PUBLICATIONS

U.S. Appl. No. 16/062,037, filed Sep. 3, 2020.
U.S. Appl. No. 16/062,037, filed Mar. 23, 2020.
U.S. Appl. No. 16/062,037, filed Oct. 4, 2019.
U.S. Appl. No. 16/062,037, filed May 29, 2019.
U.S. Appl. No. 16/062,049, filed Jun. 11, 2021.
U.S. Appl. No. 16/062,049, filed Dec. 30, 2020.
U.S. Appl. No. 16/062,049, filed Sep. 3, 2020.
U.S. Appl. No. 16/062,049, filed Mar. 23, 2020.
U.S. Appl. No. 16/062,049, filed Oct. 4, 2019.
U.S. Appl. No. 16/062,049, filed May 29, 2019.
Borujeni, M. et al., "Molecular aspects of diabetes mellitus: Resistin, microRNA, and exosome," J Cell Biochem., vol. 119:1257-1272(2018).
Dipietro, A. et al., "Angiogenesis and wound repair: when enough is enough," Journal of Leukocyte Biology, vol. 100: 6 pages (2016).
Lingohr, M. et al., "Specific regulation of IRS-2 expression by glucose in rat primary pancreatic islet beta-cells," The Journal of Biological Chemistry, vol. 281(23):15884-15892 (2006).
Ziegler, O. et al., "Hemobiological activity of gliclazide in diabetes mellitus ," Diabetes Research and Clinical Practice, vol. 14: S83-S90 (1991).
Ramzi, A. and Gamlen T., "Diabetes is associated with post-translational modifications in plasminogen resulting in reduced plasmin generation and enzyme-specific activity," Blood, 122(1):134-142 (2013).

\* cited by examiner

METHOD FOR MAKING GLUCAGON AND INSULIN RESTORE NORMAL BALANCE

RELATED APPLICATIONS

This application is a 35 U.S.C. 371 national stage filing of International Application No. PCT/CN2017/089066, filed on Jun. 19, 2017, which claims priority from International Application No. PCT/CN2016/110171, filed on Dec. 15, 2016. The contents of these applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 14, 2019, is named BCLS_006US_SEQ.txt and is 47245 bytes in size.

TECHNICAL FIELD

The present invention relates to a method for restoring a balance between glucagon and insulin to normal, comprising administering an effective amount of plasminogen to a subject; furthermore, the present invention relates to a medicament for restoring a balance between glucagon and insulin to normal.

BACKGROUND ART

Diabetes mellitus (DM) is a common genetically predisposed abnormal glucose metabolism disease with endocrine disorder, and is caused by absolute or relative insufficient insulin secretion. In 2015, there were 415 million patients with diabetes mellitus worldwide, and the number of patients with diabetes mellitus is expected to reach 642 million by 2040[1]. Diabetes mellitus is one of the major diseases that seriously endanger human health.

The main manifestations of diabetes mellitus are abnormal glucose metabolism and metabolic disorders of substances such as fats and proteins; furthermore, long-term hyperglycemia may lead to serious diabetic complications, including microvascular complications, diabetic nephropathy, diabetic cardiomyopathy, diabetic neuropathy, diabetic dermopathy, diabetes mellitus with infections, etc. Among them, diabetic nephropathy and diabetic neuropathy have a great impact on the quality of the life of patients, and are severely harmful.

Clinically common diabetes mellitus can be divided into four types: type 1 diabetes mellitus (T1DM), type 2 diabetes mellitus (T2DM), gestational diabetes mellitus, and special types of diabetes mellitus. Among them, patients with T1DM and T2DM are the most common, while patients with gestational diabetes mellitus and special types of diabetes mellitus are relatively few.

T1DM is believed to be associated with genetic factors, environmental factors (such as viral infections, diabetogenic chemicals, and dietary factors) and autoimmune factors. Studies have shown that there are at least 17 gene loci associated with T1DM, which are located on different chromosomes. In terms of environmental factors, environmental factors that affect the onset of T1DM comprise viral infections, diabetogenic chemicals, and dietary factors, in which viral factors are the most important. By far, mumps, rubella virus, cytomegalovirus and the like have been found to be associated with pathogenesis of T1DM. The mechanism is that the viruses can directly destroy pancreatic islet β cells, and after the viruses damage the pancreatic islet β cells, autoimmune reactions are triggered, which cause further damage to the pancreatic islet β cells. Diabetogenic chemicals such as alloxan, streptozotocin (STZ) and pentamidine act on pancreatic islet β cells, leading to destruction of the pancreatic islet β cells. The autoimmune factors comprise humoral immunity and cellular immunity. Humoral immunity is manifested by the presence of multiple autoantibodies against pancreatic islet β cells in the blood circulation of a patient. The main manifestation of cellular immunity is that abnormal expression of HLA-DA antigen and overexpression of IL-2 receptor and pancreatic islet cell surface HLA class 1 antigens can be observed on surfaces of pancreatic islet inflammatory infiltrating cells and pancreatic islet β cells, and the ratio of CD4+/CD8+ in the peripheral blood and the levels of IL-1, TNF-α, and INF-γ are elevated. The pathological changes caused by these factors focus on the destruction of the pancreatic islet β-cells, resulting in an absolute decrease in the level of insulin in the body, thereby causing T1DM, and therefore T1DM is considered to be an autoimmune disease.

T2DM is a polygenic disease, and is generally considered to be multi-sourced, wherein environmental factors and genetic factors work together to cause insulin resistance; and the manifestation of T2DM is that insulin at a concentration the same as the normal level cannot function normally due to the resistance in the body. Accordingly, in order to achieve the normal blood glucose level, the body will excessively secrete insulin to alleviate the "low-efficiency" state of insulin in service, and if it continues this way, the requirements for the pancreatic islet β cells are getting higher and higher, ultimately causing damage to the pancreatic islet β cells themselves due to "overwork", thus developing into absolute insulin deficiency.

Pathogenesis of DM

The pathogenesis of DM is complex, and is mainly related to family genetic predisposition, ethnic heterogeneity, insulin receptor deficiency, impaired insulin receptor substrate, up-regulation of protein tyrosine phosphatase-related genes, excessive immune inflammatory response, lipotoxicity, oxidative stress, impaired mitochondria etc.[2-3]

1. Free Fatty Acids

Elevated levels of free fatty acids are one of the causes of insulin resistance and also one of the important characteristics of insulin resistance. Under the influence of genetic factors or environmental factors, the level of free fatty acids in the blood increases, and when it exceeds the storage capacity of adipose tissues, insulin resistance occurs. Studies have shown that long-term high-fat diets lead to pancreatic islet β cell dysfunction, because high-fat diets not only trigger peripheral insulin resistance, but also increase the abdominal fat content and reduce the capacity of insulin to inhibit lipolysis, thereby promoting an increase in the content of free fatty acids, which in turn inhibits the phosphorylation of tyrosine sites in the insulin receptor and the insulin receptor substrates IRS-1 and IRS-2, thereby inhibiting the activity of P13K, which results in the insulin signal transduction pathway being hindered, thereby forming insulin resistance.

2. Inflammatory Response

1) Inflammation and Insulin Resistance

T2DM is a mild, non-specific inflammatory disease. Studies of recent years have shown that the main mechanism of inflammation leading to insulin resistance is that there is a cross-effect between inflammatory factors and the signal transduction of insulin receptor substrates: on the one hand, an inflammatory factor resulting from non-specific inflammation hinders the IRS/PI3K signaling pathway, and on the other hand, a series of kinases activated by the inflammatory factor induce phosphorylation of serine and threonine sites in IRS, which hinders normal tyrosine phosphorylation, ultimately resulting in the insulin signal transduction capacity being decreased and insulin resistance being induced[2-3].

In a target cell, the binding of insulin to a receptor thereof can activate the receptor, then the signal transduction pathway in the cell results in a series of intracellular transduction molecules and enzymatic cascade reactions to complete the stepwise transmission and amplification of the signal in the cell, and finally, the signal is passed to a target organ to produce a series of biological effects. There are two main signal transduction pathways, one being IRS-1-PI3K-PKB/AKT pathway and the other being mitogen-activated protein kinase (Shc/Raf/MAPK) pathway. In the first pathway, firstly insulin binds to a receptor thereof under the stimulation of exogenous insulin and/or glucose, thereby activating an endogenous tyrosine kinase of the receptor. The activated tyrosine kinase induces tyrosine site phosphorylation in the insulin receptor substrate IRS while achieving phosphorylation of the tyrosine kinase itself. The activated IRS migrates to the cell membrane, phosphotyrosine is anchored to the IRS tyrosine kinase via a phosphotyrosine binding domain (PTB), and the tyrosine-phosphorylated IRS recruits regulatory subunit P85 of PI3K via an SH2 domain. P85 binds to a phosphoinositol 3-phosphate molecule and converts phosphatidylinositol monophosphate (PIP) to phosphatidylinositol diphosphate (PIP2) and phosphatidylinositol triphosphate (PIP3), both of which are second messengers of insulin and other growth factors, and are anchor sites for downstream signaling molecules phosphoinositide-dependent protein kinase-1 (PDK1) and/or some subtypes of protein kinase c (PKC). PDK1 can activate protein kinase B (PKB, also known as Akt) and an atypical PKC subtype. The activated PKB on the one hand inactivates glycogen synthase kinase-3 (GSK3) by means of serine/threonine phosphorylation and on the other hand activates the mammalian target of rapamycin (mTOR) protein kinase, thereby inducing phosphorylation activation of 70ku-S6 kinase (p70S6K) downstream. The mTOR protein kinase can act as an "ATP receptor" and activates p70s6K without $Ca_2^+$/cAMP, thereby achieving controlled protein synthesis, enhanced gene transcription, and facilitation of pancreatic islet β cell hypertrophy, as well as other biological effects. PKB can directly induce the phosphorylation of serine/threonine in certain transcription factors to promote the occurrence of cell mitosis[4-5]. In the second pathway, the activation of Ras may be achieved via two pathways. 1) Activated insulin receptor activates IRS-2 protein, and the IRS-2 protein can transmit the signal to the adaptor protein growth factor receptor binding protein 2 (Grb2), which in turn interacts with a signaling protein GDP/GTP exchange factor (mSOS), and can in turn activate inactivated Ras-GDP into Ras-GT to achieve the activation of Ras. The direct action of the insulin receptor phosphorylates tyrosine in signaling protein Shc, and then Shc binds to Grb2 to activate Ras via the mSOS pathway. Activated Ras-GTP recruits Raf serine kinase, which sequentially phosphorylates MAPK kinase and MAPK. The activated MAPK may activate other protein kinases to participate in processes such as inducing gene transcription, and regulating apoptosis[6].

By far, it has been confirmed that the serine residue of IRS-1 may be phosphorylated by various inflammatory kinases such as c-Jun N-terminal kinase (JNK), IκB kinase β (IκKβ) and protein kinase C (PKC)-θ. Radio immunoassay shows that serine site 307 is the major site for the phosphorylation of IRS-1 by JNK, and its mutation causes JNK-induced IRS-1 phosphorylation and the inhibitory effect of TNF on insulin-induced IRS-1 tyrosine phosphorylation to disappear. JNK reduces the phosphorylation of tyrosine in the insulin receptor substrate by phosphorylating serine 307 of IRS-1, thereby inhibiting insulin signal transduction[7]. Hiorsumi et al. found that the activity of JNK was significantly increased in the liver, muscle, and adipose tissues of diet-induced obese mice and ob/ob mice. Gene knockout (JNK1−/−) can attenuate insulin resistance in the diet-induced obese mice and alleviate obesity, hyperglycemia, and hyperinsulinemia in the ob/ob mice. The level of phosphorylation of serine site 307 of IRS-1 in the liver tissue of the obese mice was higher than that of lean mice; however, no increase was found in the knockout (JNK1−/−) obese mice; it can be seen that the serine site 307 of IRS-1 was the target at which the JNK acts in vivo[8]. Studies have shown that in a model of TNFα stimulation-induced hepatocyte insulin resistance, JNK inhibitors can completely block the phosphorylation of serine 307. IκKβ can affect insulin signal transduction via at least two pathways, i.e., by directly inducing the phosphorylation of Ser307 of IRS-1 or by the phosphorylation of IκB, thereby activating NF-κB, which indirectly induces insulin resistance by stimulating the expression of various inflammatory factors.

Inflammatory responses are defensive responses of the human immune system against infections, tissue damages and stress responses after these injuries occur, and are also involved in etiology or pathogenesis of diabetes mellitus, cardiovascular diseases and tumors.

As early as in 1993, Hotmamisligil et al.[9] demonstrated through animal experiments that insulin-resistant obese rats had high levels of pro-inflammatory cytokines and TNF-α in adipose tissues. Since then, many researchers have begun to explore the relationship between inflammation and obesity and the relationship between inflammation and insulin resistance, and explore the molecular pathogenesis. In 2006, Hotmamisligil[10] first proposed a new medical definition, i.e. metabolic inflammation, to emphasize that this low-grade, chronic systemic inflammation is mainly caused by excess nutrients and metabolites. Metabolic inflammation may have molecular and signal transduction pathways similar to those for typical inflammations; unlike typical inflammations that we have known in the past, metabolic inflammation does not have the symptoms of redness, swelling, heat, pain, and dysfunction. Under normal circumstances, the internal environment of the body is in a steady state, and inflammations and metabolisms maintain dynamic equilibrium states respectively or therebetween. In case of metabolic disorders in an body, such an equilibrium in the body is broken, causing imbalance of the immune system, triggering an inflammatory signal transduction pathway, thereby prompting the body to release a series of inflammatory factors. Some of the inflammatory factors even amplify antoinflammatory responses to form an inflammatory waterfall effect, which further develops insulin resistance in the body, thus leading to the occurrence of metabolic syndrome.

Studies have shown that TNF-α is closely related to metabolic syndrome. TNFs, also known as dyscrasia, are mainly produced by activated macrophages, natural killer (NK) cells and T lymphocytes, wherein the TNF secreted by macrophages is called TNF-α, and lymphotoxin secreted by T lymphocytes is called TNF-β. The biological activity of TNF-α accounts for 70%-95% of the overall activity of TNFs, and therefore, usually reference to TNF at present is mostly reference to TNF-α. After years of research and discussion, it has been confirmed that TNF-α is associated with various diseases such as insulin resistance, autoimmune diseases, tumors, and chronic hepatitis B. TNF-α plays a crucial role in onset and development of insulin resistance. Swaroop et al.[11] concluded by detecting the level of serum TNF-α in 50 patients with T2DM that the TNF-α levels are elevated in the patients with T2DM and are significantly associated with BMI, fasting insulin level, and homeostatic model assessment insulin resistance index (HOMA-IR), suggesting that TNF-α plays an important role in pathogenesis of T2DM. It has also been pointed out in additional studies that TNF-α can inhibit the phosphorylation of the insulin receptor, and when the phosphorylation of the insulin receptor is inhibited, the expression of the gene of glucose transporter can be reduced, thereby reducing the activity of lipoprotein lipase, ultimately leading to lipolysis[12].

2) Inflammation and Pancreatic Islet β Cell Apoptosis

A chronic, low-grade inflammatory response is closely related to pancreatic islet β cell dysfunction. Pancreatic islet β cell dysfunction caused by a decrease in the number of β cells is another important cause of the pathogenesis of T2DM, and β cell apoptosis is the most important cause of the decrease in the number of the β cells. Due to genetic or dietary reasons, patients with T2DM are susceptible to insulin resistance; furthermore, in case of patients with elevated blood glucose, hyperglycemia can promote production of IL-6 which can not only reduce expression of GLUT4, reduce transport of glucose by fat cells, hinder glycogen synthesis, and reduce insulin sensitivity, but can also promote secretion of IL-6 by pancreatic islet cells, causing a vicious circle. Hyperglycemia induces the production of a large amount of IL-1β, which results in pancreatic islet cell apoptosis by activating pathways such as NF-κB, MAPK, Fas and NO, and there are cross-facilitations of various inflammatory pathways to aggravate the apoptosis of pancreatic islet cells, which eventually leads to pancreatic islet function failure[13]. In addition, IL-1β can also mediate interactions of leukocytes, and mutually interact and restrict with other cytokines such as IFN-γ and TNF-α, and play an important role in the process of a β cell injury. Dyslipidemia in T2DM causes an increase in the level of hormonal substances such as leptin and that of IL-6. Leptin can increase the release of IL-1β to induce β cell apoptosis, and can also negatively regulate insulin secretion[14]. In addition to causing insulin resistance, ROS also has an effect on the injury of pancreatic islet β cells, and under oxidative stress, the expression of insulin gene transcription factors, and insulin binding sites are remarkably reduced, thereby affecting the production and secretion of insulin. Other adipocytokines such as TNF-α and leptin may also reduce the function of the β cells[15]. The combined action of these cytokines causes more remarkable damage to the function of the pancreatic islet β cells. In addition, some inflammatory factors may also act on the key part of insulin receptor substrate 2 to phosphorylate serine/threonine, which results in accelerated degradation of insulin receptor substrate 2 and promotes apoptosis of pancreatic islet β cells.

3. Oxidative Stress

Studies have shown that oxidative stress is an important factor in the onset and development of T2DM. Oxidative stress refers to the imbalance between the production of reactive oxygen species (ROS) and reactive nitrogen species (RNS) and the elimination thereof by the antioxidant defense system in the body, resulting in excessive production of ROS and RNS, thereby causing damages to histocytes and biological macromolecules, such as proteins and nucleic acids, in the body[13]. Hyperglycemia is the main cause of oxidative stress, and increases the content of ROS and RNS in the body via pathways such as a mitochondrial electron transport chain[14], glucose autooxidation and a polyol pathway[15], wherein the mitochondrial electron transport chain is the predominant pathway of producing ROS. The mitochondrial electron transport chain mainly involves enzyme complexes I-IV, cytochrome c and coenzyme Q, wherein a small amount of superoxide products, comprising superoxide anion, hydrogen peroxide and hydroxyl radicals, are continuously produced in enzyme complexes I and III, while superoxide dismutase, catalase and glutathione peroxidase catalyze the conversion of superoxide products to oxygen gas and water. However, under obesity or hyperglycemia conditions, the superoxide products are greatly increased, and oxidative stress is generated when the rate of production of the superoxide products exceeds the rate of elimination thereof.

A number of studies[16-18] have shown that ROS can directly damage the β cells, especially destroy cell mitochondrial structure and promote β cell apoptosis; ROS may also indirectly inhibit the function of the β cells by affecting the insulin signal transduction pathway, for example, by activating the nuclear transcription factor κB (NF-κB) signal pathway to cause a β-cell inflammatory response, inhibiting the nucleo-cytoplasmic translocation of pancreatic and duodenal homeobox 1 (PDX-1), inhibiting mitochondrial energy metabolism, reducing insulin synthesis and secretion, etc. Oxidative stress causes a β cell injury via the NF-κB pathway, wherein NF-κB is a dimer composed of two subunits, p50 and RelA, and in a resting cell, it binds to inhibitory protein IκB to exist as an inactive trimer in the cytoplasm, which is mainly involved in the response of the cell to stimulations such as stress, cytokines, free radicals, bacteria and viruses, and in the transient regulation of gene expression, etc.[19] Studies have shown that hyperglycemia-induced ROS activates NF-κB by disrupting intracellular signal transduction and induces β cell injuries[20]. Mariappan et al.[21] inhibited the expression of NF-κB in obese db/db mice by using pyrrolidine dithiocarbamate (PDTC), and found that the degree of damage caused by oxidative stress to mitochondria of β cells in the mice was remarkably reduced; Hofmann et al.[22] treated diabetic patients with anti-oxidant drug α-lipoic acid and found that the activity of NF-κB was significantly reduced in the bodies of the patients, and the condition of the patients was also improved; and Eldor et al.[23] specifically inhibited the expression of NF-κB in mice by using a transgenic technique, which remarkably reduced the incidence of diabetes mellitus in the mice induced by STZ.

As a multi-directional nuclear transcription factor, NF-κB is involved in various gene regulations after being activated, such as cell proliferation, apoptosis, inflammation and immunity[24]. In a body with diabetes mellitus, NF-κB causes leukocytosis of pancreatic islet by regulating the expression of genes of cytokines and chemokines, such as IL-1 (interleukin-1) and MCP-1 (monocyte/macrophage chemoattractant protein-1) factors, thereby causing a 13 cells injury[25]. In addition, many gene products regulated by NF-κB, such as tumor necrosis factor α (TNF-α), further activate NF-κB, which aggravates the β cell injury[26].

Studies by Mahadev et al.[27] showed that ROS has a regulatory effect on insulin signal transduction, and this effect is versatile. Under insulin stimulation, the body rapidly produces a trace amount of ROS by means of a Nox (NADPH oxidase)-dependent mechanism; the ROS acts as a second messenger, which mainly inhibits the activity of PTP1B by means of oxidation to promote an insulin cascade reaction[28]; furthermore, after Nox is inhibited using DPI (diphenyleneiodonium), the phosphorylation of insulin-stimulated insulin receptor (InsR) and insulin receptor substrate (IRS) is decreased by 48%[29]. Studies by Loh et al.[30] showed that physiological ROS can promote the sensitivity of the body to insulin. Although in a physiological state, a trace amount of ROS produced by insulin stimulation promotes the action of insulin, long-term hyperglycemia causes the body to produce a large amount of ROS via the mitochondrial pathway[31], causing insulin resistance.

InsR and IRS are important signaling elements in the insulin signal transduction pathway: the former is an initiating element for insulin signal transduction, and the IRS is a bridge between the former and a downstream element in the pathway. Numerous studies have shown that oxidative stress may interfere with the phosphorylation of InsR and IRS via multiple pathways to hinder the insulin signal transduction. IKK is an activator for inhibitory subunit IκB of NF-κB, and under ROS stimulation, IKK may act as a kinase for the phosphorylation of serine/threonine of InsR and IRS, which promotes serine phosphorylation in InsR and IRS, causing normal tyrosine phosphorylation to be inhibited, thereby hindering the insulin signal transduction[32]. Studies by Brownlee[33] showed that IKK can directly phosphorylate a serine residue at site 307 of IRS, resulting in the normal tyrosine phosphorylation of IRS to be reduced, which hinders the binding of InsR to IRS, thereby causing insulin resistance.

In addition to IKK, several members of the MAPK family also have an effect on InsR and IRS. JNK, extracellular regulated protein kinases (ERK) and p38 mitogen-activated protein kinase (p38 MAPK) are members of the MAPK family, have serine/threonine protein kinase activities, and can be activated under the actions of oxidative stress, cytokines, G-protein coupled receptor agonists, etc. Multiple studies have shown that the activation of JNK, ERK and p38 MAPK aggravates the degree of phosphorylation of serine/threonine in InsR and IRS, and the protein binding capacity between InsR and IRS and the ability of IRS to activate a downstream signaling molecules containing an SH-2 domain are reduced[34-36].

Oxidative stress caused by a diabetic high glucose condition is one of the key causes of the formation of various chronic complications, and is also an important factor in inducing DNA damage[37]. In case of diabetes mellitus, the extracellular fluid has continuous high glucose. In this state, electrons generated by the mitochondrial electron transport chain are remarkably increased, resulting in excessive ROS, causing damages to the intracellular environment and biological macromolecules such as lipids, proteins, and DNA. Reactive oxygen produced by the body in the aerobic metabolic pathway acts as a mutation-inducing agent to oxidize guanine on the DNA strand to 8-hydroxy-2'-deoxyguanosine (8-OHdG). During DNA replication, 8-OHdG is prone to mismatch with adenine, resulting in a G:C to T:A transversion mutation that forms DNA damage. In addition, ROS may further cause other forms of DNA damage, comprising DNA strand breaks, DNA site mutations, DNA double-strand aberrations, protooncogene and tumor suppressor gene mutations, and the like. Furthermore, the DNA damage may also aggravate ROS and oxidative stress processes, for example, the DNA damage may induce ROS production by means of H2AX-reduced coenzyme II oxidase 1 (Nox1)/Rac 1 pathway. ROS further promotes the entry of a large amount of $Ca^{2+}$ into mitochondria, causing cell necrosis and apoptosis, or directly damaging mitochondria to cause mitochondrial dysfunction, thereby impairing pancreatic islet β cells and aggravating the pathological process of diabetes mellitus[38].

In addition to causing insulin resistance, ROS also has an effect on the injury of pancreatic islet β cells, and under oxidative stress, the expression of insulin gene transcription factors, and insulin binding sites are remarkably reduced, thereby affecting the production and secretion of insulin. Other adipocytokines such as TNF-α may also reduce the function of the β cells[15]. The combined action of these cytokines causes more remarkable damage to the function of the pancreatic islet β cells. In addition, some inflammatory factors may also act on the key part of insulin receptor substrate 2 to phosphorylate serine/threonine, which results in accelerated degradation of insulin receptor substrate 2 and promotes apoptosis of pancreatic islet β cells.

It can be seen from the above that the role of oxidative stress in the occurrence and development of diabetes mellitus is very complicated. In addition to directly impairing islet β cells, ROS can also act as a signaling molecule to activate some stress-sensitive pathways, thereby regulating the expression of related factors, causing apoptosis or necrosis of β cells, inhibiting insulin secretion, inducing insulin resistance, and ultimately causing or aggravating diabetes mellitus.

Treatment of DM

Diabetes mellitus is usually treated by means of medications, and traditional medications comprise insulin-based drugs and oral hypoglycemic drugs.

In the early days, insulin was mainly extracted from the pancreas of animals such as pigs and cattle, and after application to human, remarkable allergic reactions occurred. With increased maturity in the 1990s, insulin analogues were gradually applied, and such insulin can remarkably change the pharmacokinetics of traditional insulin, and has the advantages of a low incidence of hypoglycemia, fast onset, long-lasting effect, etc. At present, with the deepening of the exploration of insulin preparations, some oral insulin preparations have entered a testing stage; however, due to technical difficulties, no effective oral preparations have been applied yet clinically.

There are many traditional oral hypoglycemic drugs, among which the following types are common: (1) biguanides such as metformin. Metformin has a good cardiovascular protective effect and also a good hypoglycemic effect, and it has been used as a first-line drug for treating T2DM in many countries. (2) Sulfonylureas: sulfonylureas are insulin secretagogues that stimulate pancreatic islet β cells to secrete insulin, thus achieving an effect of improving the blood glucose level. At present, such insulins that are allowed to be marketed in China mainly comprise glimepiride, glibenclamide, glipizide, gliclazide, gliquidone, etc.; however, some studies have shown that if such drugs are taken for a long term, failed hypoglycemic effect may be caused, which easily results in complications such as hypoglycemia and increased body mass. (3) Thiazolidinedione compounds (TZD): In 1999, the FDA approved the use of rosiglitazone and pioglitazone for T2DM, wherein the former may aggravate the risk of heart diseases and for this reason, it was later restricted to be used as a second-line treatment drug and prohibited for use in heart failure conditions. In June 2013, the FDA re-examined rosiglitazone, stated that this drug can continue to be used clinically, and even relaxed or completely unbanned the prohibition of the use of this drug and compound preparations thereof. (4) α-glycosidase inhibitors: Such insulins inhibit glycosidase in small intestinal mucosal epithelial cells, thereby alleviating the absorption of carbohydrates and leading to a decrease in the postprandial blood glucose level. Commonly used such drugs comprise voglibose, acarbose, miglitol etc.

At the present stage, drugs for treating diabetes mellitus mainly comprise traditional antidiabetic drugs, comprising sulfonylureas, glinides, biguanides, thiazolidinediones (TZDs), α-glucosidase inhibitors, insulin, etc.; however, these drugs all have different degrees of adverse reactions, such as triggering hypoglycemia, gastrointestinal discomfort, and obesity. With the deepening of the study on the basic theory of diabetes mellitus, people are actively looking for new therapeutic targets for diabetes mellitus in order to avoid the side effects of traditional hypoglycemic drugs and protect the pancreatic islet β cells. Targets currently found to be associated with the pathogenesis of diabetes mellitus mainly comprise glucagon-like peptide-1 (GLP-1), and dipeptidyl peptidase-4 (DPP-4), sodium-glucose cotransporter-2 (SGLT-2), glycogen synthase kinase-3 (GSK-3), protein tyrosine phosphatase (PTP), glucokinase (GK), etc. Among them, glucagon regulation-based drugs such as glucagon-like peptide-1 (GLP-1) analogues, GLP-1 receptor agonists, and dipeptidyl peptidase-4 (DPP-4) inhibitors are considered to be effective in maintaining blood glucose homeostasis, improving β cell functions, delaying the progression of diabetes mellitus, and even reversing the course of diabetes mellitus.

Currently, there is no effective drug or means for completely curing diabetes mellitus, and current medications focus on reducing and delaying the occurrence of complications by controlling blood glucose within a certain range. With a deeper and more comprehensive understanding of the pathogenesis of diabetes, the study of therapeutic drugs for diabetes mellitus has also been shifted from the study of drugs with traditional mechanisms to the study of drugs with new targets and new mechanisms of action, wherein some of them have already been on the market, for example, GLP-1 receptor agonists, DPP-4 inhibitors and SGLT-2 inhibitors, and there are also some drugs in the clinical or preclinical study stage, e.g. GPR119 receptor agonists, 11β-HSD1 inhibitors, PTP1B inhibitors and GK agonists, with the efficacy and safety having yet to be further clinically verified. Although the emergence of new target-based antidiabetic drugs in recent years has provided more options for DM treatment, since the pathogenesis of diabetes mellitus is complex, and a large number of hormones, enzymes and receptors are involved, there are still problems, e.g. single-target drugs having a narrow range of action, a weak hypoglycemic effect and causing adverse reactions after acting on the systemic system, in the research field of new drugs, and all of these need to be further studied. Therefore, people need to find more effective therapeutic drugs that can act on many aspects of the pathogenesis of diabetes mellitus.

The present invention discovers that plasminogen can alleviate the pancreatic tissue injury, control inflammation, reduce pancreatic islet β cell apoptosis, repair pancreatic tissue, restore the secretion function of pancreatic islet β-cells, and reducing blood glucose in diabetic experimental mice, and is expected to become a brand new drug that comprehensively addresses many aspects of the pathogenesis of diabetes mellitus.

BRIEF DESCRIPTION OF THE INVENTION

The present invention comprises the following items:

1. A method for reducing secretion of glucagon in a diabetic subject, comprising administering an effective amount of plasminogen to the subject.

2. The method of item 1, wherein the plasminogen further reduces expression of glucagon in the diabetic subject.

3. The method of item 1 or 2, wherein the diabetes mellitus is T1DM or T2DM.

4. The method of any one of items 1 to 3, wherein the plasminogen reduces secretion of glucagon in the diabetic subject after eating.

5. The method of any one of items 1 to 4, wherein the plasminogen reduces secretion of glucagon in the diabetic subject in a fasted state.

6. The method of any one of items 1 to 5, wherein the plasminogen returns blood glucose to a normal or nearly normal level by reducing secretion of glucagon in the diabetic subject in an elevated blood glucose state.

7. The method of any one of items 1 to 6, wherein the plasminogen promotes expression and/or secretion of insulin while reducing the expression and/or secretion of glucagon in the subject.

8. The method of item 7, wherein the plasminogen achieves a return to a normal or nearly normal level of blood glucose in the subject by promoting the expression and/or secretion of insulin while reducing expression and/or secretion of glucagon in the subject.

9. The method of any of items 1 to 8, wherein the plasminogen promotes expression of insulin receptor substrate 2 (IRS-2).

10. A method for promoting secretion of insulin in a diabetic subject, comprising administering an effective amount of plasminogen to the subject.

11. The method of item 10, wherein the plasminogen further promotes expression of insulin in the diabetic subject.

12. The method of item 10 or 11, wherein the diabetes mellitus is T1DM or T2DM.

13. The method of any one of items 10 to 12, wherein the plasminogen promotes secretion of insulin in the diabetic subject after eating.

14. The method of any one of items 10 to 12, wherein the plasminogen promotes secretion of insulin in the diabetic subject in a fasted state.

15. The method of any one of items 10 to 14, wherein the plasminogen returns blood glucose to a normal or nearly normal level by promoting secretion of insulin in response to a stimulation of elevated blood glucose in the diabetic subject.

16. The method of any one of items 10 to 15, wherein the plasminogen reduces expression and/or secretion of glucagon in the subject while promoting the expression and/or secretion of insulin.

17. The method of any one of item 16, wherein the plasminogen achieves a return to a normal or nearly normal level of blood glucose in the subject by reducing expression and/or secretion of glucagon in the subject while promoting the expression and/or secretion of insulin.

18. A method for reducing blood glucose in a diabetic subject, comprising administering an effective amount of plasminogen to the subject.

19. The method of item 18, wherein the blood glucose is selected from one or more of: a serum glucose level, a serum fructosamine level, and a serum glycated hemoglobin level.

20. The method of item 19, wherein the blood glucose is a serum glucose level.

21. The method of any one of items 18 to 20, wherein the diabetes mellitus is T1DM or T2DM.

22. A method for improving the glucose tolerance in a diabetic subject, comprising administering an effective amount of plasminogen to the subject.

23. The method of item 22, wherein the diabetes mellitus is T2DM.

24. A method for promoting postprandial blood glucose drop in a diabetic subject, comprising administering an effective amount of plasminogen to the subject.

25. The method of item 24, wherein the plasminogen is administered 30 minutes to 1.5 hour before the subject has a meal.

26. The method of item 25, wherein the plasminogen is administered 30 minutes to 1 hour before the subject has a meal.

27. A method for promoting the utilization of glucose in a diabetic subject, comprising administering an effective amount of plasminogen to the subject.

28. The method of any one of items 1 to 27, wherein the plasminogen is administered in combination with one or more other drugs or therapies.

29. The method of item 28, wherein the plasminogen is administered in combination with one or more drugs selected from anti-diabetic drugs, drugs against cardiovascular and cerebrovascular diseases, anti-thrombotic drugs, anti-hypertensive drugs, antilipemic drugs, anticoagulant drugs, and anti-infective drugs.

30. The method of any one of items 1 to 29, wherein the plasminogen has at least 75%, 80%, 85%, 90%, 95%, 96%, 97%, 98% or 99% sequence identity with SEQ ID No. 2, 6, 8, 10 or 12, and still has the plasminogen activity.

31. The method of any one of items 1 to 30, wherein the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the plasminogen activity.

32. The method of any one of items 1 to 31, wherein the plasminogen is a protein that comprises a plasminogen active fragment and still has the plasminogen activity.

33. The method of any one of items 1 to 32, wherein the plasminogen is selected from Glu-plasminogen, Lys-plasminogen, mini-plasminogen, micro-plasminogen, delta-plasminogen or their variants that retain the plasminogen activity.

34. The method of any one of items 1 to 33, wherein the plasminogen is a natural or synthetic human plasminogen, or a variant or fragment thereof that still retains the plasminogen activity.

35. The method of any one of items 1 to 33, wherein the plasminogen is an ortholog of human plasminogen from a primate or a rodent, or a variant or fragment thereof that still retains the plasminogen activity.

36. The method of any one of items 1 to 35, wherein the amino acids of the plasminogen are as shown in SEQ ID No. 2, 6, 8, 10 or 12.

37. The method of any one of items 1 to 36, wherein the plasminogen is a natural human plasminogen.

38. The method of any one of items 1 to 37, wherein the subject is a human.

39. The method of any one of items 1 to 38, wherein the subject has a lack or deficiency of plasminogen.

40. The method of any one of items 1 to 39, wherein the lack or deficiency is congenital, secondary and/or local.

41. A plasminogen for use in the method of any one of items 1 to 40.

42. A pharmaceutical composition, comprising a pharmaceutically acceptable carrier and the plasminogen for use in the method of any one of items 1 to 40.

43. A preventive or therapeutic kit comprising: (i) the plasminogen for use in the method of any one of items 1 to 40, and (ii) a means for delivering the plasminogen to the subject.

44. The kit of item 43, wherein the means is a syringe or a vial.

45. The kit of item 43 or 44, further comprising a label or an instruction for use indicating the administration of the plasminogen to the subject to implement the method of any one of items 1 to 40.

46. An article of manufacture, comprising:
a container comprising a label; and
(i) the plasminogen for use in the method of any one of items 1 to 40 or a pharmaceutical composition comprising the plasminogen, wherein the label indicates the administration of the plasminogen or the composition to the subject to implement the method of any one of items 1 to 40.

47. The kit of any one of items 43 to 45 or the article of manufacture of item 46, further comprising one or more additional means or containers containing other drugs.

48. The kit or the article of manufacture of item 47, wherein the other drugs are selected from the group of anti-diabetic drugs, drugs against cardiovascular and cerebrovascular diseases, anti-thrombotic drugs, anti-hypertensive drugs, antilipemic drugs, anticoagulant drugs, and anti-infective drugs.

In one aspect, the present invention relates to a method for preventing and/or treating diabetes mellitus, comprising administering a therapeutically effective amount of plasminogen or plasmin to a subject.

In another aspect, the present invention relates to a method for reducing blood glucose in a diabetic subject, comprising administering an effective amount of plasminogen to the subject. The present invention further relates to the use of plasminogen for reducing blood glucose in a diabetic subject. The present invention further relates to the use of plasminogen in the preparation of a medicament for reducing blood glucose in a diabetic subject. In addition, the present invention further relates to a plasminogen for reducing blood glucose in a diabetic subject. In some embodiments, the blood glucose is selected from one or more of: a serum glucose level, a serum fructosamine level, and a serum glycated hemoglobin level. In some other embodiments, the blood glucose is a serum glucose level. In the above-mentioned embodiments, the diabetes mellitus is T1DM or T2DM.

In another aspect, the present invention relates to a method for improving the glucose tolerance in a diabetic subject, comprising administering an effective amount of plasminogen to the subject. The present invention further relates to the use of plasminogen for increasing glucose tolerance in a diabetic subject. The present invention further relates to the use of plasminogen in the preparation of a medicament for increasing glucose tolerance in a diabetic subject. In addition, the present invention further relates to a plasminogen for increasing glucose tolerance in a diabetic subject. In some embodiments, the diabetes mellitus is T2DM.

In one aspect, the present invention relates to a method for promoting postprandial blood glucose drop in a diabetic subject, comprising administering an effective amount of plasminogen to the subject. The present invention further relates to the use of plasminogen for promoting postprandial blood glucose drop in a diabetic subject. The present invention further relates to the use of plasminogen in the preparation of a medicament for promoting postprandial blood glucose drop in a diabetic subject. In addition, the present invention further relates to a plasminogen for promoting postprandial blood glucose drop in a diabetic subject. In some embodiments, the plasminogen is administered 30 minutes to 1.5 hours before the subject has a meal. In some other embodiments, the plasminogen is administered 30 minutes to 1 hour before the subject has a meal.

In one aspect, the present invention relates to a method for promoting the utilization of glucose in a diabetic subject, comprising administering an effective amount of plasminogen to the subject. The present invention further relates to the use of plasminogen for promoting the utilization of glucose in a diabetic subject. The present invention further relates to the use of plasminogen in the preparation of a medicament for promoting the utilization of glucose in a diabetic subject. In addition, the present invention further relates to a plasminogen for promoting the utilization of glucose in a diabetic subject. In another aspect, the present invention relates to a method for promoting secretion of insulin in a diabetic subject, comprising administering an effective amount of plasminogen to the subject. In other embodiments, the plasminogen further promotes the expression of insulin in a diabetic subject. In the above-mentioned embodiments, the diabetes mellitus is T1DM or T2DM. In some embodiments, the plasminogen promotes secretion of insulin in the diabetic subject after eating. In some other embodiments, the plasminogen promotes secretion of insulin in the diabetic subject in a fasted state. In some embodiments, the plasminogen returns blood glucose to a normal or nearly normal level by promoting secretion of insulin in response to an elevated blood glucose stimulation in the diabetic subject. In some other embodiments, the plasminogen reduces expression and/or secretion of glucagon in the subject while promoting the expression and/or secretion of insulin; in particular, the plasminogen achieves a return to a normal or nearly normal level of blood glucose in the subject by reducing expression and/or secretion of glucagon in the subject while promoting the expression and/or secretion of insulin.

In one aspect, the present invention relates to a method for reducing secretion of glucagon in a diabetic subject, comprising administering an effective amount of plasminogen to the subject. The present invention further relates to the use of plasminogen for reducing secretion of glucagon in a diabetic subject. The present invention further relates to the use of plasminogen in the preparation of a medicament for reducing secretion of glucagon in a diabetic subject. In addition, the present invention further relates to a plasminogen for reducing secretion of glucagon in a diabetic subject. In some embodiments, the plasminogen further reduces expression of glucagon in the diabetic subject. In the above-mentioned embodiments, the diabetes mellitus is T1DM or T2DM. In some embodiments, the plasminogen reduces secretion of glucagon in the diabetic subject after eating. In some other embodiments, the plasminogen reduces secretion of glucagon in the diabetic subject in a fasted state. In some embodiments, the plasminogen returns blood glucose to a normal or nearly normal level by reducing secretion of glucagon in the diabetic subject in an elevated blood glucose state. In some embodiments, the plasminogen returns blood glucose to a normal or nearly normal level by reducing secretion of glucagon in the diabetic subject in an elevated blood glucose state. In some other embodiments, the plasminogen promotes expression and/or secretion of insulin while reducing the expression and/or secretion of glucagon in the subject; in particular, the plasminogen achieves a return to a normal or nearly normal level of blood glucose in the subject by promoting the expression and/or secretion of insulin while reducing expression and/or secretion of glucagon in the subject. In the above-mentioned embodiments, the plasminogen promotes expression of insulin receptor substrate 2 (IRS-2).

In one aspect, the present invention relates to a method for promoting repair of a pancreatic islet cell injury in a diabetic subject, comprising administering an effective amount of plasminogen to the subject. The present invention further relates to the use of plasminogen for promoting repair of a pancreatic islet cell injury in a diabetic subject. The present invention further relates to the use of plasminogen in the preparation of a medicament for promoting repair of a pancreatic islet cell injury in a diabetic subject. In addition, the present invention further relates to a plasminogen for promoting repair of a pancreatic islet cell injury in a diabetic subject. In some embodiments, the plasminogen promotes expression of insulin receptor substrate 2 (IRS-2). In some other embodiments, the plasminogen promotes expression of cytokine TNF-α. In some other embodiments, the plasminogen promotes expression of multi-directional nuclear transcription factor NF-κB in the subject. In some embodiments, the pancreatic islet cell injury is one or more selected from: an injured insulin synthesis and secretion function of pancreatic islet β cells, an injured pancreatic islet tissue structure, collagen deposition in the pancreatic islet, pancreatic islet fibrosis, pancreatic islet cell apoptosis, a disordered balance between the secretion of glucagon and of insulin in the pancreatic islet, and failed adaptation of levels of glucagon and insulin secreted by the pancreatic islet to a blood glucose level in a subject. In some embodiments, the plasminogen reduces secretion of glucagon and increases secretion of insulin in the diabetic subject; in particular, the normal balance between the secretion of glucagon and of insulin in the pancreatic islet is repaired.

In another aspect, the present invention relates to a method for protecting the pancreatic islet of a subject, comprising administering an effective amount of plasminogen to the subject. The present invention further relates to the use of plasminogen for protecting the pancreatic islet of a subject. The present invention further relates to the use of plasminogen in the preparation of a medicament for protecting the pancreatic islet of a subject. In addition, the present invention further relates to a plasminogen for protecting the pancreatic islet of a subject. In some embodiments, the plasminogen reduces collagen deposition in the pancreatic islet. In some other embodiments, the plasminogen reduces pancreatic islet fibrosis. In some other embodiments, the plasminogen reduces pancreatic islet cell apoptosis. In some other embodiments, the plasminogen promotes expression of insulin receptor substrate 2 (IRS-2) in the pancreatic islet. In some embodiments, the plasminogen promotes repair of an inflammation in the pancreatic islet. In some other embodiments, the plasminogen promotes expression of cytokine TNF-α. In some other embodiments, the plasminogen promotes expression of multi-directional nuclear transcription factor NF-κB in the subject. In the above-mentioned embodiments, the subject is a diabetic patient; in particular, the diabetic patient has T1DM or T2DM. In some embodiments, the subject with T1DM is a subject with normal PLG activity or impaired PLG activity.

In one aspect, the present invention relates to a method for promoting repair of an inflammation in the pancreatic islet, comprising administering an effective amount of plasminogen to the subject. The present invention further relates to the use of plasminogen for promoting repair of an inflammation in the pancreatic islet of a diabetic subject. The present invention further relates to the use of plasminogen in the preparation of a medicament for promoting repair of an inflammation in the pancreatic islet of a diabetic subject. In addition, the present invention further relates to a plasminogen for promoting repair of an inflammation in the pancreatic islet of a diabetic subject. In some embodiments, the plasminogen promotes expression of cytokine TNF-α. In some other embodiments, the plasminogen promotes expression of multi-directional nuclear transcription factor NF-κB in the subject. In some other embodiments, the plasminogen reduces collagen deposition in the pancreatic islet. In some other embodiments, the plasminogen reduces pancreatic islet fibrosis. In some other embodiments, the plasminogen inhibits pancreatic islet cell apoptosis. In the above-mentioned embodiments, the diabetic patient has T1DM or T2DM; in particular, the subject with T1DM is a subject with normal PLG activity or impaired PLG activity.

In one aspect, the present invention relates to a method for promoting expression of cytokine TNF-α in a diabetic subject, comprising administering an effective amount of plasminogen to the subject. The present invention further relates to the use of plasminogen for promoting expression of cytokine TNF-α in a diabetic subject. The present invention further relates to the use of plasminogen in the preparation of a medicament for promoting expression of cytokine TNF-α in a diabetic subject. In addition, the present invention further relates to a plasminogen for promoting expression of cytokine TNF-α in a diabetic subject.

In another aspect, the present invention relates to a method for promoting expression of multi-directional nuclear transcription factor NF-κB in a diabetic subject, comprising administering an effective amount of plasminogen to the subject. The present invention further relates to the use of plasminogen for promoting expression of multi-directional nuclear transcription factor NF-κB in a diabetic subject. The present invention further relates to the use of plasminogen in the preparation of a medicament for promoting expression of multi-directional nuclear transcription factor NF-κB in a diabetic subject.

In another aspect, the present invention relates to a method for promoting expression of insulin receptor substrate 2 (IRS-2) by the pancreatic islet, comprising administering an effective amount of plasminogen to the subject. The present invention further relates to the use of plasminogen for promoting expression of insulin receptor substrate 2 (IRS-2) in the pancreatic islet. The present invention further relates to the use of plasminogen in the preparation of a medicament for promoting expression of insulin receptor substrate 2 (IRS-2) in the pancreatic islet. In addition, the present invention further relates to a plasminogen for promoting expression of insulin receptor substrate 2 (IRS-2) in the pancreatic islet.

In another aspect, the present invention relates to a method for promoting secretion of insulin in a diabetic subject, comprising administering an effective amount of plasminogen to the subject to promote expression of insulin receptor substrate 2 (IRS-2). The present invention further relates to the use of plasminogen for promoting secretion of insulin in a diabetic subject. The present invention further relates to the use of plasminogen in the preparation of a medicament for promoting secretion of insulin in a diabetic subject. In addition, the present invention further relates to a plasminogen for promoting secretion of insulin in a diabetic subject.

In another aspect, the present invention relates to a method for promoting an increase in the number of pancreatic islet β cells in a diabetic subject, comprising administering an effective amount of plasminogen to the subject.

The present invention further relates to the use of plasminogen for promoting an increase in the number of pancreatic islet β cells in a diabetic subject. The present invention further relates to the use of plasminogen in the preparation of a medicament for promoting an increase in the number of pancreatic islet β cells in a diabetic subject. In addition, the present invention further relates to a plasminogen for promoting an increase in the number of pancreatic islet β cells in a diabetic subject. In some embodiments, the plasminogen promotes expression of insulin receptor substrate 2 (IRS-2).

In one aspect, the present invention relates to a method for reducing pancreatic islet β cell apoptosis, comprising administering an effective amount of plasminogen to a subject. The present invention further relates to the use of plasminogen for reducing pancreatic islet β cell apoptosis. The present invention further relates to the use of plasminogen in the preparation of a medicament for reducing pancreatic islet β cell apoptosis. In addition, the present invention further relates to a plasminogen for reducing pancreatic islet β cell apoptosis. In some embodiments, the plasminogen promotes expression of insulin receptor substrate 2 (IRS-2).

In another aspect, the present invention relates to a method for promoting repair of a pancreatic islet β cell injury, comprising administering an effective amount of plasminogen to a subject. The present invention further relates to the use of plasminogen for promoting repair of a pancreatic islet β cell injury. The present invention further relates to the use of plasminogen in the preparation of a medicament for promoting repair of a pancreatic islet β cell injury. The present invention further relates to a plasminogen for promoting repair of a pancreatic islet β cell injury. In some embodiments, the plasminogen promotes expression of insulin receptor substrate 2 (IRS-2).

In another aspect, the present invention relates to a method for promoting recovery of pancreatic islet β cell function, comprising administering an effective amount of plasminogen to a subject. The present invention further relates to the use of plasminogen for promoting recovery of pancreatic islet β cell function. The present invention further relates to the use of plasminogen in the preparation of a medicament for promoting recovery of pancreatic islet β cell function. In addition, the present invention further relates to a plasminogen for promoting recovery of pancreatic islet β cell function. In some embodiments, the plasminogen promotes expression of insulin receptor substrate 2 (IRS-2).

In the above-mentioned embodiments, the plasminogen is administered in combination with one or more other drugs or therapies. In particular, the plasminogen may be administered in combination with one or more drugs selected from anti-diabetic drugs, drugs against cardiovascular and cerebrovascular diseases, anti-thrombotic drugs, anti-hypertensive drugs, antilipemic drugs, anticoagulant drugs, and anti-infective drugs.

In the above-mentioned embodiments, the plasminogen has at least 75%, 80%, 85%, 90%, 95%, 96%, 97%, 98% or 99% sequence identity with SEQ ID No. 2, 6, 8, 10 or 12, and still has the activity of plasminogen.

In the above-mentioned embodiments, the amino acids of the plasminogen are as shown in SEQ ID No. 2, 6, 8, 10 or 12. In some embodiments, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the activity of plasminogen.

In the above-mentioned embodiments, the plasminogen is a protein that comprises a plasminogen active fragment and still has the activity of plasminogen. Specifically, the plasminogen is selected from Glu-plasminogen, Lys-plasminogen, mini-plasminogen, micro-plasminogen, delta-plasminogen or their variants that retain the plasminogen activity.

In the above-mentioned embodiments, the plasminogen is a natural or synthetic human plasminogen, or a variant or fragment thereof that still retains the plasminogen activity. In some embodiments, the plasminogen is an ortholog of human plasminogen from a primate or a rodent, or a variant or fragment thereof that still retains the plasminogen activity. For example, the plasminogen is an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No. 2, 6, 8, 10 or 12.

In the above-mentioned embodiments, the subject is a human. In some embodiments, the subject has a lack or deficiency of plasminogen. Specifically, the lack or deficiency is congenital, secondary and/or local.

In one embodiment, the plasminogen is administered by systemic or topical route, preferably by the following routes: topical, intravenous, intramuscular, subcutaneous, inhalation, intraspinal, local injection, intraarticular injection or rectal route. In one embodiment, the topical administration is performed by direct administration to osteoporotic areas, for example through a means such as a dressing and a catheter.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances. In one aspect, the present invention relates to a pharmaceutical composition, comprising a pharmaceutically acceptable carrier and the plasminogen for use in the method of the present invention.

In another aspect, the present invention relates to a preventive or therapeutic kit comprising: (i) the plasminogen for use in the method of the present invention, and (ii) a means for delivering the plasminogen to the subject, in particular, the means is a syringe or a vial. In some embodiments, the kit further comprises a label or an instruction for use indicating the administration of the plasminogen to the subject to implement the methods of the present invention.

In another aspect, the present invention further relates to an article of manufacture comprising: a container comprising a label; and (i) the plasminogen for use in the methods of the present invention or a pharmaceutical composition comprising the plasminogen, wherein the label indicates the administration of the plasminogen or the composition to the subject to implement the methods of the present invention.

In the above-mentioned embodiments, the kit or the article of manufacture further comprises one or more additional means or containers containing other drugs. In some embodiments, the other drugs are selected from the group of anti-diabetic drugs, drugs against cardiovascular and cerebrovascular diseases, anti-thrombotic drugs, anti-hypertensive drugs, antilipemic drugs, anticoagulant drugs, and anti-infective drugs.

DETAILED DESCRIPTION OF EMBODIMENTS

"Diabetes mellitus" is a series of dysmetabolic syndromes of carbohydrates, proteins, fats, water, electrolytes and the like that are caused by islet hypofunction, insulin resistance and the like resulting from the effects of genetic factors, immune dysfunction, microbial infections and toxins thereof, free radical toxins, mental factors and other various pathogenic factors on the body, and is mainly characterized by hyperglycemia clinically.

"Diabetic complications" are damages to or dysfunctions of other organs or tissues of the body caused by poor blood glucose control during diabetes mellitus, including damages to or dysfunctions of the liver, kidneys, heart, retina, nervous system damage and the like. According to statistics of the World Health Organization, there are up to more than 100 diabetic complications, and diabetes mellitus is a disease currently known to have the most complications.

"Insulin resistance" refers to a decrease in the efficiency of insulin in promoting glucose uptake and utilization for various reasons, resulting in compensatory secretion of excess insulin in the body, which causes hyperinsulinemia to maintain blood glucose stability.

"Plasmin" is a very important enzyme that exists in the blood and is capable of degrading fibrin multimers.

"Plasminogen (plg)" is the zymogen form of plasmin, which is a glycoprotein composed of 810 amino acids calculated based on the amino acid sequence (SEQ ID No. 4) of the natural human plasminogen containing a signal peptide according to the sequence in the swiss prot, having a molecular weight of about 90 kD, being synthesized mainly in the liver and being capable of circulating in the blood, with the cDNA sequence that encodes this amino acid sequence is as shown in SEQ ID No. 3. Full-length PLG contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No. 1; and the amino acid sequence is as shown in SEQ ID No. 2. In vivo, Lys-plasminogen, which is formed by hydrolysis of amino acids at positions 76-77 of Glu-plasminogen, is also present, as shown in SEQ ID No. 6; and the cDNA sequence encoding this amino acid sequence is as shown in SEQ ID No. 5. δ-plasminogen is a fragment of full-length plasminogen that lacks the structure of Kringle 2-Kringle 5 and contains only Kringle 1 and the serine protease domain[39,40]. The amino acid sequence (SEQ ID No. 8) of δ-plasminogen has been reported in the literature[40], and the cDNA sequence encoding this amino acid sequence is as shown in SEQ ID No. 7. Mini-plasminogen is composed of Kringle 5 and the serine protease domain, and has been reported in the literature to comprise residues Val443-Asn791 (with the Glu residue of the Glu-plg sequence that does not contain a signal peptide as the starting amino acid)[41]; the amino acid sequence is as shown in SEQ ID No. 10; and the cDNA sequence encoding this amino acid sequence is as shown in SEQ ID No. 9. In addition, micro-plasminogen comprises only the serine protease domain, the amino acid sequence of which has been reported in the literature to comprise residues Ala543-Asn791 (with the Glu residue of the Glu-plg sequence that does not contain a signal peptide as the starting amino acid)[42], and the sequence of which has been also reported in patent CN 102154253 A to comprise residues Lys531-Asn791 (with the Glu residue of the Glu-plg sequence that does not contain a signal peptide as the starting amino acid) (the sequence in this patent application refers to the patent CN 102154253 A); the amino acid sequence is as shown in SEQ ID No. 12; and the cDNA sequence encoding this amino acid sequence is as shown in SEQ ID No. 11.

In the present invention, "plasmin" is used interchangeably with "fibrinolysin" and "fibrinoclase", and the terms have the same meaning; and "plasminogen" is used interchangeably with "profibrinolysin" and "fibrinoclase zymogen", and the terms have the same meaning.

In the present application, the meaning of "lack" in plasminogen is that the content or activity of plasminogen in the body of a subject is lower than that of a normal person, which is low enough to affect the normal physiological function of the subject; and the meaning of "deficiency" in plasminogen is that the content or activity of plasminogen in the body of a subject is significantly lower than that of a normal person, or even the activity or expression is extremely small, and only through exogenous supply can the normal physiological function be maintained.

Those skilled in the art can understand that all the technical solutions of the plasminogen of the present invention are suitable for plasmin. Therefore, the technical solutions described in the present invention cover plasminogen and plasmin.

In the embodiments of the present invention, "aging" and "premature aging" are used interchangeably to mean the same meaning.

In the course of circulation, plasminogen is in a closed, inactive conformation, but when bound to thrombi or cell surfaces, it is converted into an active PLM in an open conformation under the mediation of a PLG activator (plasminogen activator, PA). The active PLM can further hydrolyze the fibrin clots to fibrin degradation products and D-dimers, thereby dissolving the thrombi. The PAp domain of PLG comprises an important determinant that maintains plasminogen in an inactive, closed conformation, and the KR domain is capable of binding to lysine residues present on receptors and substrates. A variety of enzymes that can serve as PLG activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID No. 14, or an amino acid sequence having an amino acid sequence identity of at least 80%, 90%, 95%, 96%, 97%, 98% or 99% with SEQ ID No. 14. Therefore, plasminogen of the present invention comprises a protein containing the plasminogen active fragment and still having the plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the PLG in the test plasma is converted into PLM by the action of SK, PLM acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity, hydrophobicity, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowry method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining. Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues); and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction X/Y×100 wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "prevention" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

2. Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus*, for example, *Bacillus subtilis* and other species of enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (e.g., mammalian cells cultured in cell culture in vitro) may also be used to express the plasminogen of the present invention. See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the subject antibody and the like.

3. Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or non-ionic surfactants, such as TWEEN™, PLURONICS™ or polyethylene glycol (PEG). Preferred lyophilized anti-VEGF antibody formulations are described in WO 97/04801, which is incorporated herein by reference.

The formulations of the invention may also comprise one or more active compounds required for the particular condition to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and γ ethyl-L-glutamic acid (Sidman et al. Biopolymers 22:547(1983)), non-degradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(−)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulfhydryl residues, lyophilizing from acidic solutions, controlling moisture content, using appropriate additives, and developing specific polymer matrix compositions.

4. Administration and Dosage

The pharmaceutical composition of the present invention is administered in different ways, for example by intravenous, intraperitoneal, subcutaneous, intracranial, intrathecal, intraarterial (e.g., via carotid), intramuscular, intranasal, topical or intradermal administration or spinal cord or brain delivery. An aerosol preparation, such as a nasal spray preparation, comprises purified aqueous or other solutions of the active agent along with a preservative and isotonic agent. Such preparations are adjusted to a pH and isotonic state compatible with the nasal mucosa.

In some cases, the plasminogen pharmaceutical composition of the present invention may be modified or formulated in such a manner to provide its ability to cross the blood-brain barrier.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

In some embodiments, the plasminogen of the invention is formulated with an agent that promotes the plasminogen to cross the blood-brain barrier. In some cases, the plasminogen of the present invention is fused directly or via a linker to a carrier molecule, peptide or protein that promotes the fusion to cross the blood brain barrier. In some embodiments, the plasminogen of the present invention is fused to a polypeptide that binds to an endogenous blood-brain barrier (BBB) receptor. The polypeptide that is linked to plasminogen and binds to an endogenous BBB receptor promotes the fusion to cross the BBB. Suitable polypeptides that bind to endogenous BBB receptors include antibodies (e.g., monoclonal antibodies) or antigen-binding fragments thereof that specifically bind to endogenous BBB receptors. Suitable endogenous BBB receptors include, but are not limited to, insulin receptors. In some cases, antibodies are encapsulated in liposomes. See, for example, US Patent Publication No. 2009/0156498.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, such as about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety of thrombosis and a thrombosis-related disease are required to be assessed real-timely and regularly.

5. Treatment Efficacy and Treatment Safety

One embodiment of the present invention relates to the judgment of treatment efficacy and treatment safety after treating a subject with plasminogen. Common monitoring and assessment contents of therapeutic effect for osteoporosis comprise follow-up survey (adverse reactions, standardized medication, basic measures, re-assessment of fracture risk factors, etc.), new fracture assessment (clinical fracture, body height reduction, and imageological examination), bone mineral density (BMD) measurement, and detection of bone turnover markers (BTM), comprehensive re-assessment based on these data, etc. Among them, BMD is currently the most widely used method for monitoring and assessing the therapeutic effect. For example, BMD can be measured by means of dual energy X-ray absorptiometry (DXA), quantitative computed tomography (QCT), single photon absorption measurement (SPA), or ultrasonometry. BMD can be detected once a year after the start of treatment, and after the BMD has stabilized, the interval may be appropriately extended, for example, to once every 2 years. For BTM, among serological indicators, serum procollagen type 1 N-terminal propeptide (PINP) is relatively frequently used at present as a bone formation indicator, and serum type 1 procollagen C-terminal peptide (serum C-terminal telopeptide, S-CTX) serves as a bone resorption indicator. According to the research progress, more reasonable detection indicators are adjusted where appropriate. Baseline values should be measured prior to the start of treatment, and detections are carried out 3 months after the application of a formation-promoting drug therapy, and 3 to 6 months after the application of a resorption inhibitor drug therapy. BTM can provide dynamic information of bones, is independent of BMD in effect and function, and is also a monitoring means complementary to BMD. The combination of the two has a higher clinical value. In general, if BMD rises or stabilizes after treatment, BTM has an expected change, and no fracture occurs during the treatment, the treatment response can be considered to be good. In addition, the present invention also relates to the judgment of the safety of the therapeutic regimen during and after treating a subject with plasminogen and its variants, including, but not limited to, statistics of the serum half-life, half-life of treatment, median toxic dose (TD50) and median lethal dose (LD50) of the drug in the body of the subject, or observing various adverse events such as sensitization that occur during or after treatment.

6. Articles of Manufacture or Kits

One embodiment of the present invention relates to an article of manufacture or a kit comprising the plasminogen of the present invention. The article preferably includes a container, label or package insert. Suitable containers include bottles, vials, syringes and the like. The container can be made of various materials, such as glass or plastic. The container contains a composition that is effective to treat the disease or condition of the present invention and has a sterile access (for example, the container may be an intravenous solution bag or vial containing a plug that can be pierced by a hypodermic injection needle). At least one active agent in the composition is plasminogen. The label on or attached to the container indicates that the composition is used for treating the aging or aging-related conditions according to the present invention. The article may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article comprises a package insert with instructions for use, including, for example, instructions to direct a user of the composition to administer to a patient the plasminogen composition and other drugs for treating an accompanying disease.

EXAMPLES

Example 1. Plasminogen Reduces Proliferation of Pancreatic Islet α Cells in 24- to 25-Week-Old Diabetic Mice, Restores Normal Distribution of Pancreatic Islet α Cells and Reduces Secretion of Glucagon Eleven male db/db mice and five male db/m mice, 24-25 weeks old, were weighed and the db/db mice were weighed and then randomly divided into two groups, a group of 5 mice administered with plasminogen and a control group of 6 mice administered with vehicle PBS, on the day the experiment started that was recorded as day 0; in addition, the db/m mice were used as a normal control group. Starting from day 1, plasminogen or PBS was administered. The mice in the group administered with plasminogen were injected with human plasminogen at a dose of 2 mg/0.2 mL/mouse/day via the tail vein, and the mice in the control group administered with vehicle PBS was injected with an equal volume of PBS via the tail vein or without any liquid, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum (Vector laboratories, Inc., USA) for 30 minutes, and after the time was up, the goat serum liquid was discarded. Rabbit anti-mouse glucagon antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Pancreatic islet α cells synthesize and secrete glucagon, which is mainly distributed in the peripheral region of the pancreatic islet.

Figure 1:
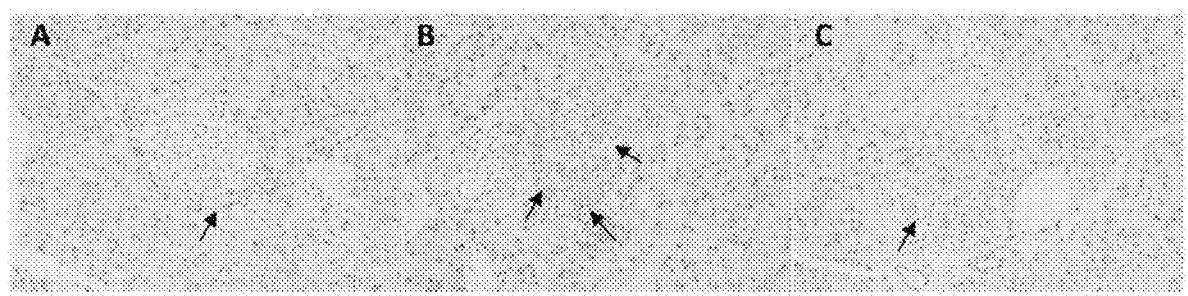
FIG. 1 shows the observed immunohistochemical results for glucagon of the pancreatic islets after administration of plasminogen to 24- to 25-week-old diabetic mice for 35 days. A represents a normal control group, B represents a control group administered with vehicle PBS, and C represents a group administered with plasminogen. The results show that glucagon is expressed in the α-cell region at the periphery of the pancreatic islet in normal control mice. Compared with the group administered with plasminogen, glucagon-positive cells (indicated by arrow) in the control group administered with vehicle PBS are remarkably increased, and the positive cells infiltrate into the central region of the pancreatic islet; and glucagon-positive cells in the group administered with plasminogen are dispersed at the periphery of the pancreatic islet, and compared with the PBS group, the morphology of the pancreatic islet in the group administered with plasminogen is closer to that of normal mice. This indicates that plasminogen can significantly inhibit proliferation of pancreatic islet α cells and secretion of glucagon, and correct the disordered distribution of pancreatic islet α cells, thus promoting repair of impaired pancreatic islet.

The results show that compared with the group administered with plasminogen (FIG. 1C), glucagon-positive cells (indicated by arrow) in the control group administered with vehicle PBS (FIG. 1B) are remarkably increased, and the positive cells infiltrate into the central region of the pancreatic islet; and glucagon-positive cells in the group administered with plasminogen are dispersed at the periphery of the pancreatic islet, and compared with the group administered with vehicle PBS, the morphology of the pancreatic islet in the group administered with plasminogen is closer to that in the normal control group (FIG. 1A). This indicates that plasminogen can significantly inhibit proliferation of pancreatic islet α cells and secretion of glucagon in 24- to 25-week-old diabetic mice, and correct the disordered distribution of pancreatic islet α cells, suggesting that plasminogen promotes repair of impaired pancreatic islet.

Example 2. Plasminogen Inhibits Proliferation of Pancreatic Islet α Cells In 26-Week-Old Diabetic Mice, Restores Normal Distribution of Pancreatic Islet α Cells and Reduces Secretion of Glucagon Nine male db/db mice and three male db/m mice, 26 weeks old, were weighed and the db/db mice were weighed and then randomly divided into two groups, a group of 4 mice administered with plasminogen and a control group of 5 mice administered with vehicle PBS, on the day the experiment started that was recorded as day 0; in addition, the db/m mice were used as a normal control group. Starting from day 1, plasminogen or PBS was administered. The mice in the group administered with plasminogen were injected with human plasminogen at a dose of 2 mg/0.2 mL/mouse/day via the tail vein, and the mice in the control group administered with vehicle PBS were injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse glucagon antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Pancreatic islet α cells synthesize and secrete glucagon, which is mainly distributed in the peripheral region of the pancreatic islet.

Figure 2:
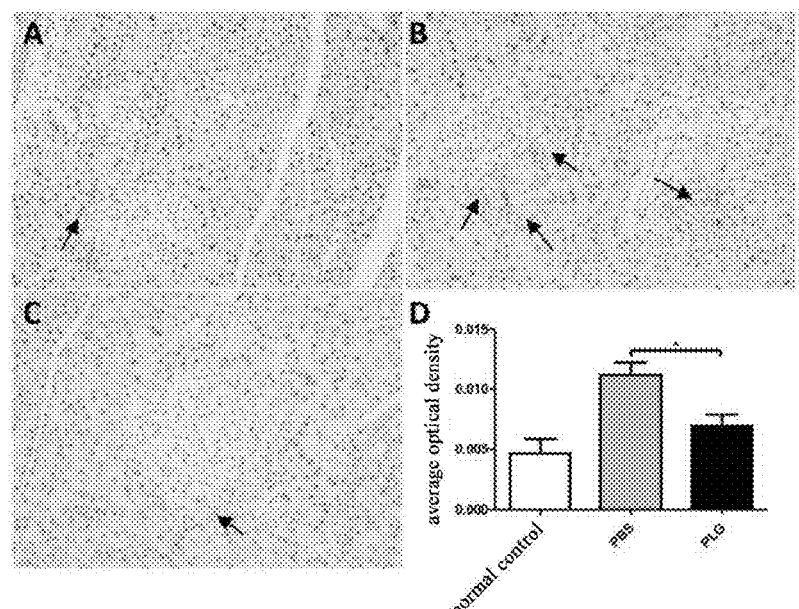
FIG. 2 shows the observed immunohistochemical results for glucagon of the pancreatic islets after administration of plasminogen to 26-week-old diabetic mice for 35 days. A represents a normal control group, B represents the control group administered with vehicle PBS, C represents the group administered with plasminogen, and D represents the quantitative analysis results. The results show that glucagon is expressed in the α-cell region at the periphery of the pancreatic islet in normal control mice. Compared with the group administered with plasminogen, positive cells (indicated by arrow) in the control group administered with vehicle PBS are remarkably increased, the glucagon-positive cells infiltrate into the central region of the pancreatic islet, and the mean optical density quantitative analysis results show a statistical difference (* indicates P<0.05); and glucagon-positive cells in the group administered with plasminogen are dispersed at the periphery of the pancreatic islet, and compared with the PBS group, the morphology of the pancreatic islet in the group administered with plasminogen is closer to that of normal mice. This indicates that plasminogen can significantly inhibit proliferation of pancreatic islet α cells and secretion of glucagon, and correct the disordered distribution of pancreatic islet α cells, thus promoting repair of impaired pancreatic islet.

The results show that compared with the group administered with plasminogen (FIG. 2C), glucagon-positive cells (indicated by arrow) in the control group administered with vehicle PBS (FIG. 2B) are remarkably increased, the positive cells infiltrate into the central region of the pancreatic islet, and the mean optical density quantitative analysis results show a statistical difference (** indicates P<0.01) (FIG. 2D); and glucagon-positive cells in the group administered with plasminogen are dispersed at the periphery of the pancreatic islet, and compared with the group administered with vehicle PBS, the morphology of the pancreatic islet in the group administered with plasminogen is closer to that in the normal control group (FIG. 2A). This indicates that plasminogen can significantly inhibit proliferation of pancreatic islet α cells and secretion of glucagon in 26-week-old diabetic mice, and correct the disordered distribution of pancreatic islet α cells, suggesting that plasminogen promotes repair of impaired pancreatic islet.

Example 3. Plasminogen Reduces Secretion of Glucagon in Mice with Normal PLG Activity in T1DM Model Fifteen 9- to 10-week-old male db/db mice with normal PLG activity were randomly divided into three groups, a blank control group, a control group administered with vehicle PBS and a group administered with plasminogen, with 5 mice in each group. The mice in the group administered with vehicle PBS and the group administered with plasminogen were fasted for 4 hours and then intraperitoneally injected with 200 mg/kg STZ (Sigma, Cat #S0130), in a single dose, to induce the T1DM model[43], while the blank group was not treated. 12 days after the injection, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse glucagon antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Pancreatic islet α cells synthesize and secrete glucagon, which is mainly distributed in the peripheral region of the pancreatic islet.

Figure 3:
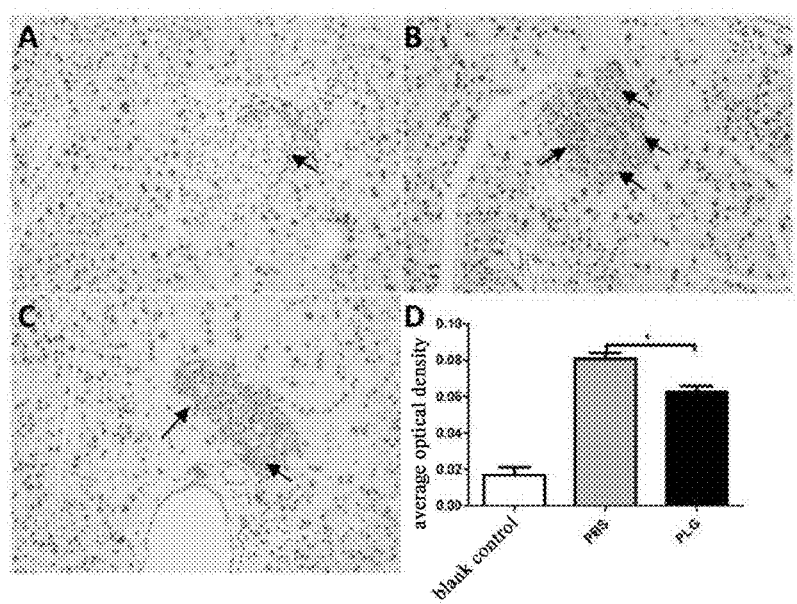
FIG. 3 shows the observed immunohistochemical results for glucagon of the pancreatic islet after administration of plasminogen to mice with normal PLG activity in a T1DM model for 28 days. A represents the blank control group, B represents the control group administered with vehicle PBS, C represents the group administered with plasminogen, and D represents the quantitative analysis results. The results show that the positive expression of glucagon in the control group administered with vehicle PBS is remarkably higher than that in the group administered with plasminogen, and the mean optical density quantitative analysis results show that the statistical difference is significant (* indicates P<0.05). This indicates that plasminogen can significantly reduce the secretion of glucagon from pancreatic islet α cells in diabetic mice and promote repair of impaired pancreatic islet.

The results show that the positive expression of glucagon in the control group administered with vehicle PBS (FIG. 3B) is remarkably higher than that in the group administered with plasminogen (FIG. 3C), and the mean optical density quantitative analysis results show that the statistical difference is significant (FIG. 3D); in addition, the result of the group administered with plasminogen is closer to that of the blank control group than that of the group administered with vehicle PBS (FIG. 3A). This indicates that plasminogen can significantly reduce secretion of glucagon from pancreatic islet α cells in STZ-induced diabetic mice.

Example 4. Plasminogen Lowers Blood Glucose in Diabetic Mice

Eight 24- to 25-week-old male db/db mice were randomly divided into two groups, a group of 5 mice administered with plasminogen, and a control group of 3 mice administered with vehicle PBS. The mice were weighed and grouped on the day when the experiment began, i.e. day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. After fasting for 16 hours on days 10 and 31, blood glucose testing was carried out using a blood glucose test paper (Roche, Mannheim, Germany).

Figure 4:
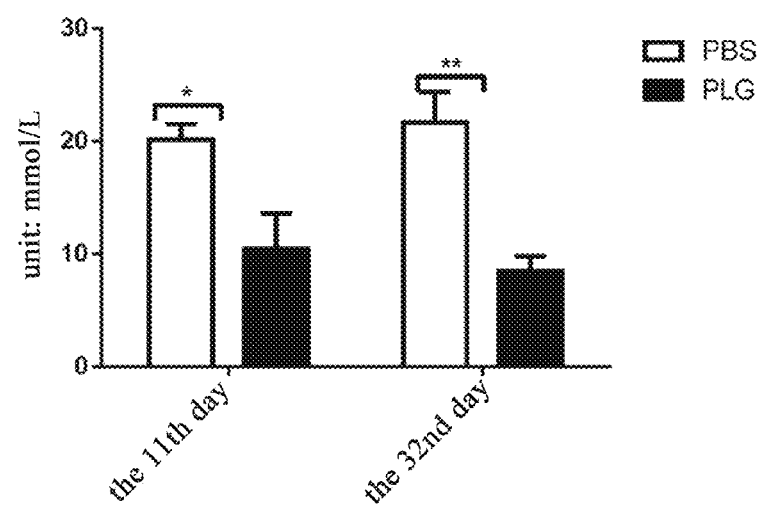
FIG. 4 shows detection results of blood glucose after administration of plasminogen to 24- to 25-week-old diabetic mice for 10 days and 31 days. The results show that the blood glucose level in mice in the group administered with plasminogen was remarkably lower than that in the control group administered with vehicle PBS, and the statistical difference was significant (* indicates P<0.05, and ** indicates P<0.01). In addition, with the prolongation of the administration time, the blood glucose level of the mice in the control group administered with vehicle PBS has a tendency to rise, while the blood glucose level of the group administered with plasminogen gradually decreases. This indicates that plasminogen has a hypoglycemic effect.

The results show that the blood glucose level in mice in the group administered with plasminogen was remarkably lower than that in the control group administered with vehicle PBS, and the statistical difference was significant (* indicates P<0.05, and ** indicates P<0.01). In addition, with the prolongation of the administration time, the blood glucose level of the mice in the control group administered with vehicle PBS has a tendency to rise, whereas the blood glucose level of the group administered with plasminogen gradually decreases (FIG. 4). This indicates that plasminogen has an effect of reducing blood glucose in diabetic animals.

Example 5. Plasminogen Lowers Fructosamine Level in Diabetic Mice

For five 24- to 25-week-old male db/db mice, 50 μl of blood was collected from venous plexus in the eyeballs of each mouse one day before administration, recorded as day 0, for detecting a concentration of serum fructosamine; and starting from day 1, plasminogen is administered for 31 consecutive days. On day 32, blood was taken from the removed eyeballs to detect the concentration of serum fructosamine. The concentration of fructosamine was measured using a fructosamine detection kit (A037-2, Nanjing Jiancheng).

Figure 5:
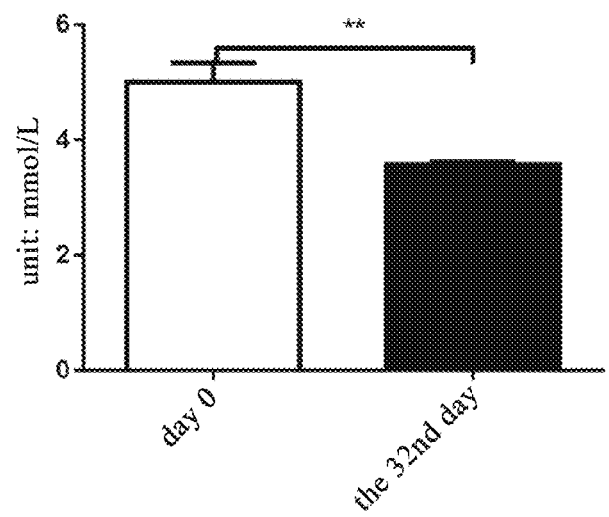
FIG. 5 shows the effect of administration of plasminogen on the concentration of serum fructosamine in diabetic mice. The detection results show that the concentration of serum fructosamine is remarkably decreased after administration of plasminogen, and as compared with that before administration, the statistical difference is extremely significant (** indicates P<0.01). This indicates that plasminogen can significantly reduce blood glucose in diabetic mice.

The concentration of fructosamine reflects the average level of blood glucose within 1 to 3 weeks. The results show that the concentration of serum fructosamine is remarkably decreased after administration of plasminogen, and as compared with that before administration, the statistical difference is extremely significant (FIG. 5). This indicates that plasminogen can effectively reduce blood glucose in diabetic animals.

Example 6. Plasminogen Lowers Serum Fructosamine Level in 26-Week-Old Diabetic Mice Nine 26-week-old male db/db mice were weighed and randomly divided, according to body weight, into two groups, a group of 4 mice administered with plasminogen and a control group of 5 mice administered with vehicle PBS, on the day the experiment started that was recorded as day 0. The mice in the group administered with plasminogen were injected with human plasminogen at a dose of 2 mg/0.2 mL/mouse/day via the tail vein, and the mice in the control group administered with vehicle PBS was injected with an equal volume of PBS via the tail vein. Plasminogen or PBS was administered to the mice from Day 1 for 35 consecutive days. On day 36, the mice were sacrificed to detect the concentration of serum fructosamine. The concentration of fructosamine was measured using a fructosamine detection kit (A037-2, Nanjing Jiancheng).

Figure 6:
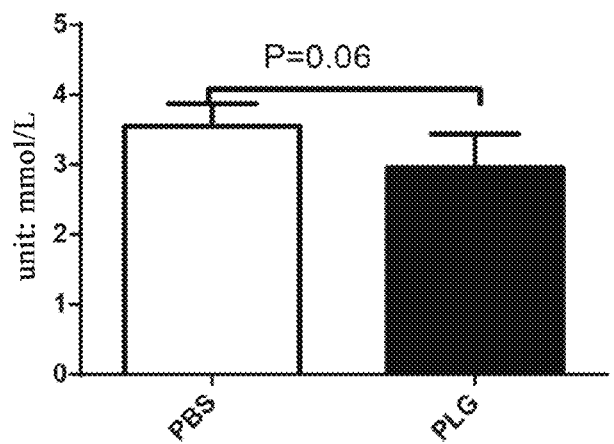
FIG. 6 shows detection results of serum fructosamine after administration of plasminogen to 26-week-old diabetic mice for 35 days. The detection results show that the concentration of serum fructosamine in the group administered with plasminogen is remarkably lower than that in the control group administered with vehicle PBS, and the statistical difference is nearly significant (P=0.06). This indicates that plasminogen can significantly reduce the blood glucose level in diabetic mice.

The detection results show that the concentration of serum fructosamine in the group administered with plasminogen is remarkably lower than that in the control group administered with vehicle PBS, and the statistical difference is nearly significant (P=0.06) (FIG. 6). This indicates that plasminogen can reduce blood glucose glycosamine in 26-week-old diabetic mice.

Example 7. Plasminogen Lowers Glycated Hemoglobin Level in Diabetic Mice

Nine 26-week-old male db/db mice were weighed and then randomly divided, according to body weight, into two groups, a group of 4 mice administered with plasminogen and a control group of 5 mice administered with vehicle PBS, on the day the experiment started. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 35, the mice were fasted for 16 hours, and on day 36, the blood was taken from removed eyeballs for detecting the concentration of plasma glycated hemoglobin.

Figure 7:
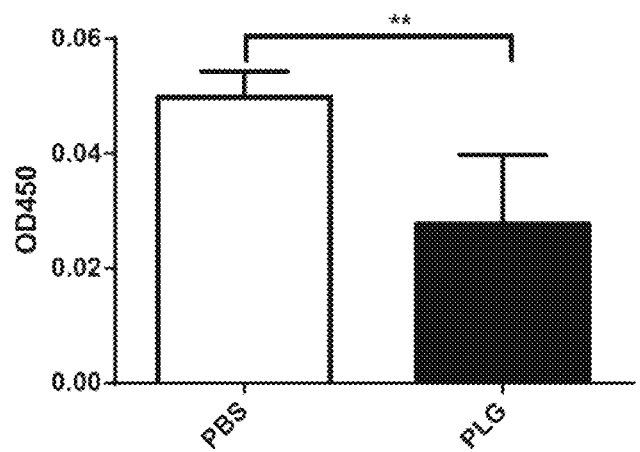
FIG. 7 shows detection results of plasma glycated hemoglobin after administration of plasminogen to 26-week-old diabetic mice for 35 days. The results show that the OD value of glycated hemoglobin in the mice in the group administered with plasminogen is remarkably lower than that in the control group administered with vehicle PBS, and the statistical difference is extremely significant (** indicates P<0.01). This indicates that plasminogen has an effect of reducing blood glucose in diabetic mice.

The content of glycated hemoglobin can generally reflect the control of blood glucose in a patient within recent 8 to 12 weeks. The results show that the concentration of glycated hemoglobin in the mice in the group administered with plasminogen is remarkably lower than that in the control group administered with vehicle PBS, and the statistical difference is significant (FIG. 7). This indicates that plasminogen can effectively reduce the blood glucose level in diabetic animals.

Example 8. Plasminogen Improves Glucose Tolerance of Diabetic Mice

Nine 26-week-old male db/db mice and three db/m mice were involved. On the day the experiment started, the db/db mice were weighed and then randomly divided, according to body weight, into two groups, a group of 4 mice administered with plasminogen and a control group of 5 mice administered with vehicle PBS, and the db/m mice were used as a normal control group. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 10 consecutive days. On day 11, after the mice were fasted for 16 hours, each mouse was intraperitoneally injected with 5% glucose solution at 5 g/kg body weight, and the concentration of blood glucose was detected 0, 30, 60, 90, 120, and 180 minutes using a blood glucose test paper (Roche, Mannheim, Germany).

An intraperitoneal glucose tolerance test (IPGTT) can detect the tolerance of a body to glucose. It is known in the prior art that the glucose tolerance of a diabetic patient is decreased.

Figure 8:
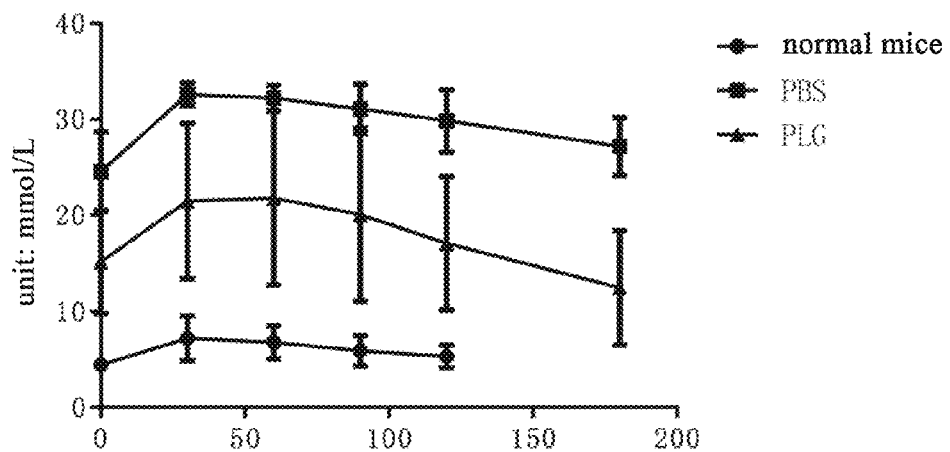
FIG. 8 shows detection results of IPGTT after administration of plasminogen to 26-week-old diabetic mice for 10 days. The results show that after intraperitoneal injection of glucose, the blood glucose level of the mice in the group administered with plasminogen is lower than that in the control group administered with vehicle PBS, and compared with the control group administered with vehicle PBS, the glucose tolerance curve of the group administered with plasminogen is closer to that of the normal mice group. This indicates that plasminogen can remarkably improve the glucose tolerance of diabetic mice.

The experimental results show that after intraperitoneal injection of glucose, the blood glucose level of the mice in the group administered with plasminogen is lower than that in the control group administered with vehicle PBS, and compared with the control group administered with vehicle PBS, the glucose tolerance curve of the group administered with plasminogen is closer to that of the normal mice group (FIG. 8). This indicates that plasminogen can remarkably improve the glucose tolerance of diabetic mice.

Example 9. Plasminogen Lowers Blood Glucose Level in Mice with Normal PLG Activity in T1DM Model Ten 9- to 10-week-old male db/db mice with normal PLG activity were randomly divided into two groups, a control group administered with vehicle PBS and a group administered with plasminogen, with 5 mice in each group. The two groups of mice were fasted for 4 hours and intraperitoneally injected with 200 mg/kg streptozotocin (STZ) (Sigma S0130), in a single dose, to induce T1DM[43]. 12 days after the injection of STZ, administration was carried out and this day was recorded as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 10 consecutive days. On day 11, after the mice were fasted for 6 hours, blood glucose testing was carried out using a blood glucose test paper (Roche, Mannheim, Germany).

Figure 9:
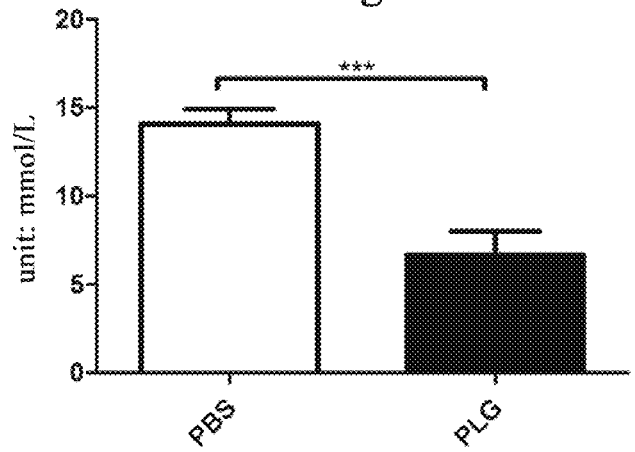
FIG. 9 shows detection results of post-fasting blood glucose after administration of plasminogen to mice with normal PLG activity in a T1DM model for 10 days. The results show that the blood glucose level of the mice in the control group administered with vehicle PBS is remarkably higher than that in the group administered with plasminogen, and the statistical difference is extremely significant (*** indicates P<0.001). This indicates that plasminogen can significantly reduce the blood glucose level in mice with normal PLG activity in the T1DM model.

The results show that the blood glucose level of the mice in the control group administered with vehicle PBS is remarkably higher than that of the mice in the group administered with plasminogen, and the statistical difference is extremely significant (FIG. 9). This indicates that plasminogen can significantly reduce the blood glucose level in mice with normal PLG activity in the T1DM model.

Example 10. Plasminogen Improves Glucose Tolerance of T1DM Model Mice

Fifteen 9- to 10-week-old male db/db mice with normal PLG activity were randomly divided into three groups, a blank control group, a control group administered with vehicle PBS and a group administered with plasminogen, with 5 mice in each group. The mice in the group administered with vehicle PBS and the group administered with plasminogen were fasted for 4 hours and then intraperitoneally injected with 200 mg/kg STZ (Sigma S0130), in a single dose, to induce T1DM[43], while the blank group was not treated. 12 days after the injection of STZ, administration was carried out and this day was recorded as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 28, after the mice were fasted for 6 hours, 5% glucose solution was intraperitoneally injected at 5 g/kg body weight, and the concentration of blood glucose was detected 0, 15, 30, 60, and 90 minutes after the injection using a blood glucose test paper (Roche, Mannheim, Germany).

An intraperitoneal glucose tolerance test (IPGTT) can detect the tolerance of a body to glucose. It is known in the prior art that the glucose tolerance of a diabetic patient is decreased.

Figure 10:
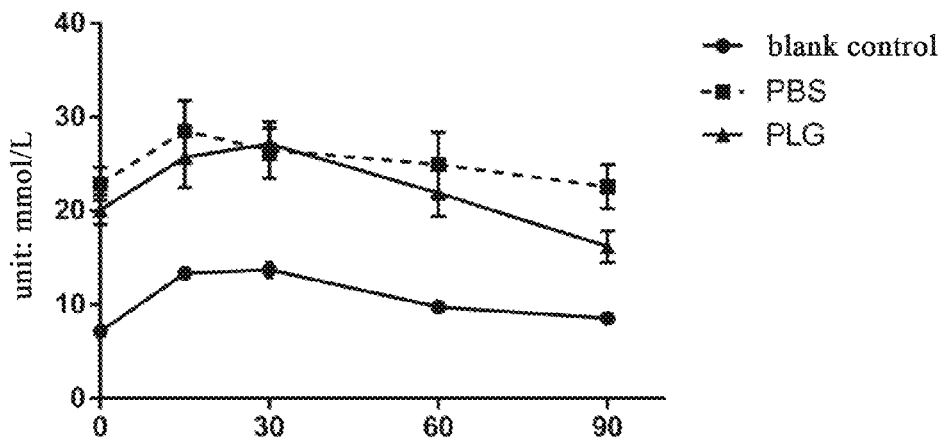
FIG. 10 shows detection results of IPGTT after administration of plasminogen to mice with normal PLG activity in a T1DM model for 28 days. The results show that after injection of glucose, the blood glucose concentration of the mice in the control group administered with vehicle PBS is remarkably higher than that in the group administered with plasminogen, and compared with the control group administered with vehicle PBS, the glucose tolerance curve of the group administered with plasminogen is closer to that of normal mice. This indicates that plasminogen can increase the glucose tolerance of mice with normal PLG activity in the T1DM model.

The results show that after injection of glucose, the blood glucose concentration of the mice in the control group administered with vehicle PBS is remarkably higher than that in the group administered with plasminogen, and compared with the control group administered with vehicle PBS, the glucose tolerance curve of the group administered with plasminogen is closer to that of normal mice (FIG. 10). This indicates that plasminogen can increase the glucose tolerance of mice with normal PLG activity in the T1DM model.

Example 11. Plasminogen Enhances Glucose Decomposing Ability of T1DM Model Mice

Eight 9- to 10-week-old male C57 mice were randomly divided into two groups, a control group administered with vehicle PBS and a group administered with plasminogen, with 4 mice in each group. The mice in the group administered with vehicle PBS and the group administered with plasminogen were fasted for 4 hours and then intraperitoneally injected with 200 mg/kg streptozotocin (STZ) (Sigma S0130), in a single dose, to induce T1DM[43]. 12 days after the injection of STZ, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein. Administration was carried out for 19 consecutive days. On day 20, after the mice were fasted for 6 hours, 20% glucose was intragastrically administered at 2 g/kg body weight, and after 60 minutes, blood was collected from the orbital venous plexus and centrifuged to obtain a supernatant, which was detected for blood glucose by means of a glucose assay kit (Rongsheng, Shanghai, 361500).

Figure 11:
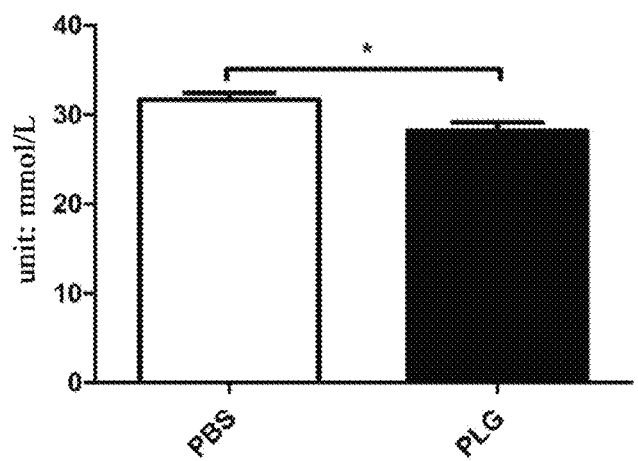
FIG. 11 shows detection results of blood glucose after administration of plasminogen to mice in a T1DM model for 20 days. The results show that the blood glucose level of the mice in the control group administered with vehicle PBS is remarkably higher than that of the mice in the group administered with plasminogen, and the statistical difference is significant (P=0.04). This indicates that plasminogen can promote the glucose decomposing ability of T1DM mice, thereby lowering blood glucose.

The results show that the blood glucose level of the mice in the control group administered with vehicle PBS is remarkably higher than that of the mice in the group administered with plasminogen, and the statistical difference is significant (P=0.04) (FIG. 11). This indicates that plasminogen can enhance the glucose decomposing ability of T1DM mice, thereby lowering blood glucose.

Example 12. Plasminogen Promotes Insulin Secretion Function of Diabetic Mice

Nine 26-week-old male db/db mice were weighed and randomly divided, according to body weight, into two groups, a group of 4 mice administered with plasminogen and a control group of 5 mice administered with vehicle PBS, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 35, the mice were fasted for 16 hours; and on day 36, the blood was taken from removed eyeballs, and centrifuged to obtain a supernatant, and the serum insulin level was detected using an insulin detection kit (Mercodia AB) according to operating instructions.

Figure 12:
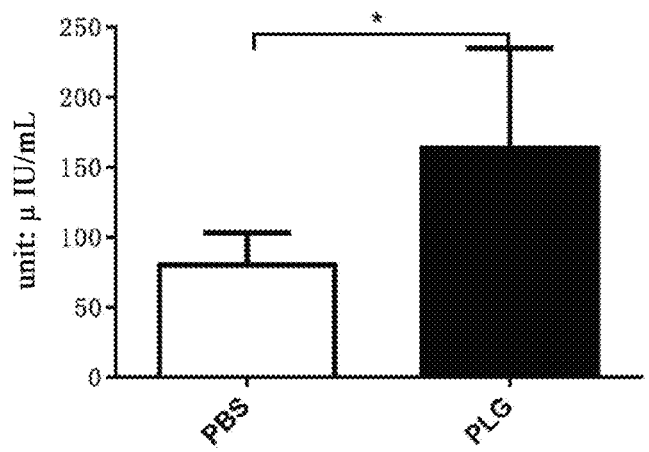
FIG. 12 shows detection results of serum insulin after administration of plasminogen to 26-week-old diabetic mice for 35 days. The results show that the serum insulin level in the group administered with plasminogen is remarkably higher than that in the control group administered with vehicle PBS, and the statistical difference is significant (* indicates P<0.05). This indicates that plasminogen can effectively promote secretion of insulin.

The detection results show that the serum insulin level in the group administered with plasminogen is remarkably higher than that in the control group administered with vehicle PBS, and the statistical difference is significant (FIG. 12). This indicates that plasminogen can significantly increase secretion of insulin in diabetic mice.

Example 13. Protective Effect of Plasminogen on Pancreas of Diabetic Mice

Seven 24- to 25-week-old male db/db mice were weighed and randomly divided, according to body weight, into two groups, a group of 4 mice administered with plasminogen and a control group of 3 mice administered with vehicle PBS, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The tissue sections were 3 μm thick. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient, and observed under an optical microscope at 200× and 400×.

Figure 13:
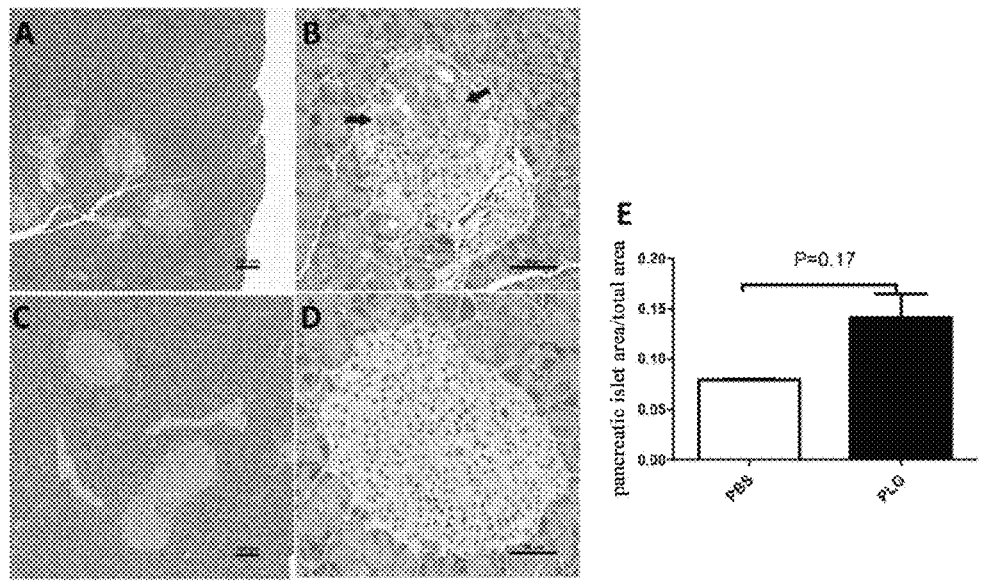
FIG. 13 shows HE-stained images of the pancreas and the pancreatic islet area ratios after administration of plasminogen to 24- to 25-week-old diabetic mice for 31 days. A and B represent control groups administered with vehicle PBS, C and D represent groups administered with plasminogen, and E represents the quantitative analysis results of pancreatic islet area. The results show that most of the pancreatic islets in the control groups administered with vehicle PBS are atrophied, the atrophied pancreatic islet cells are replaced by acini (indicated by ↓), and there is acinar hyperplasia at the edge of the pancreatic islets, causing the boundary between pancreatic islet and acini to be unclear; in the groups administered with plasminogen, most of the pancreatic islets are larger than those in the control groups, there is no acinar hyperplasia in the pancreatic islets, only a small number of acini remain in a few pancreatic islets, and the boundary between pancreatic islet and acini is clear. Comparing the groups administered with plasminogen with the control groups in terms of the area ratio of pancreatic islet to pancreas, it is found that the area ratio in the administration groups are almost twice as large as that in the control groups. This indicates that plasminogen can promote repair of impaired pancreatic islet in 24- to 25-week-old diabetic mice, by which diabetes mellitus is treated by repairing impaired pancreatic islet.

The results show that most of the pancreatic islets in the control groups administered with vehicle PBS (FIGS. 13A and 13B) are atrophied, the atrophied pancreatic islet cells are replaced by acini (indicated by arrow), and there is acinar hyperplasia at the edge of the pancreatic islets, causing the boundary between pancreatic islet and acini to be unclear; in the groups administered with plasminogen (FIGS. 13C and 13D), most of the pancreatic islets are larger than those in the control groups, there is no acinar hyperplasia in the pancreatic islets, only a small number of acini remain in a few pancreatic islets, and the boundary between pancreatic islet and acini is clear. Comparing the administration groups with the control groups in terms of the area ratio of pancreatic islet to pancreas, it is found that the area ratio in the administration groups are almost twice as large as that in the control groups (FIG. 13E). This indicates that plasminogen can promote repair of impaired pancreatic islet in diabetic mice, suggesting that plasminogen may fundamentally cure diabetes mellitus by promoting repair of impaired pancreatic islet.

Example 14. Plasminogen Reduces Collagen Deposition in the Pancreatic Islet of Diabetic Mice Sixteen 24- to 25-week-old male db/db mice were weighed and randomly divided, according to body weight, into two groups, a group of 10 mice administered with plasminogen and a control group of 6 mice administered with vehicle PBS, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The tissue sections was 3 μm thick. The sections were dewaxed and rehydrated and washed with water once. After stained with 0.1% Sirius red for 60 min, the sections were flushed with running water. After stained with hematoxylin for 1 min, the sections were flushed with running water, differentiated with 1% hydrochloric acid in alcohol and returned to blue with ammonia water, flushed with running water, dried and sealed. The sections were observed under an optical microscope at 200×.

Sirius red staining allows for long-lasting staining of collagen. As a special staining method for pathological sections, Sirius red staining can show the collagen tissue specifically.

Figure 14:
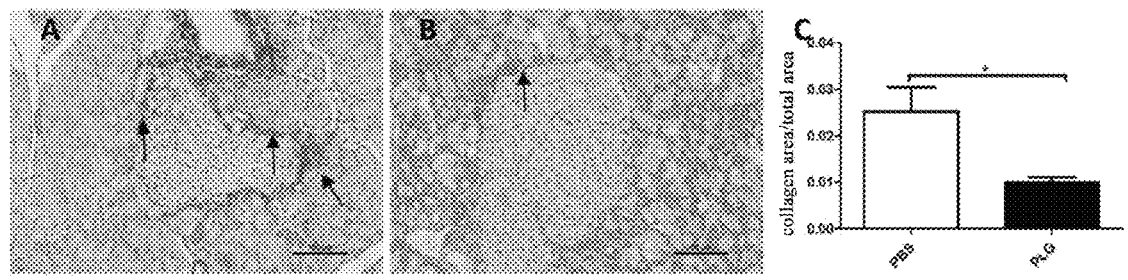
FIG. 14 shows the observed results of Sirius red-staining for pancreatic islets after administration of plasminogen to 24- to 25-week-old diabetic mice for 31 days. A represents the control group administered with vehicle PBS, B represents the group administered with plasminogen, and C represents the quantitative analysis results. The results showed that the collagen deposition (indicated by arrow) in the pancreatic islet of mice in the group administered with plasminogen was remarkably less than that in the control group administered with vehicle PBS, and the statistical difference was significant (* indicates P<0.05). This indicates that plasminogen can ameliorate pancreatic islet fibrosis in diabetic animals.

The staining results show that the collagen deposition (indicated by arrow) in the pancreatic islet of the mice in the group administered with plasminogen (FIG. 14B) was remarkably lower than that in the control group administered with vehicle PBS (FIG. 14A), and the statistical difference was significant (FIG. 14C). This indicates that plasminogen can reduce pancreatic islet fibrosis in diabetic animals.

Example 15. Plasminogen Reduces Pancreatic Islet Cell Apoptosis in Diabetic Mice Six 24- to 25-week-old male db/db mice were weighed and randomly divided, according to body weight, into two groups, a group of 4 mice administered with plasminogen and a control group of 2 mice administered with vehicle PBS, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum liquid (Vector laboratories, Inc., USA) for 1 hour, and thereafter, the goat serum liquid was discarded, and the tissues were circled with a PAP pen. The sections were incubated with rabbit anti-mouse Caspase-3 (Abcam) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with a gradient, permeabilization and sealing, the sections were observed under an optical microscope at 200×.

Caspase-3 is the most important terminal cleavage enzyme in the process of cell apoptosis, and the more the expression thereof, the more the cells in an apoptotic state[44].

Figure 15:
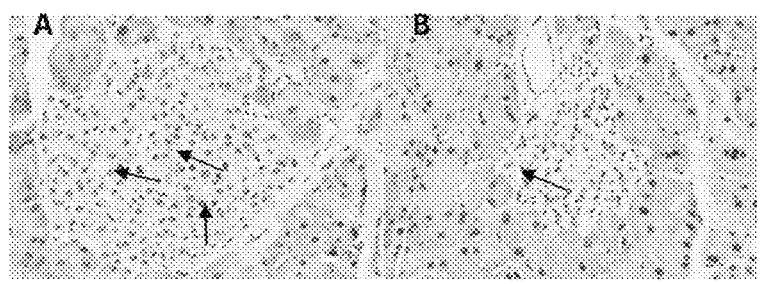
FIG. 15 shows the observed results of immunohistochemical staining for Caspase-3 of the pancreatic islets after administration of plasminogen to 24- to 25-week-old diabetic mice for 31 days. A represents the control group administered with vehicle PBS, and B represents the group administered with plasminogen. The results show that the expression of Caspase-3 (indicated by arrow) in the group administered with plasminogen is remarkably lower than that in the control group administered with vehicle PBS. This indicates that plasminogen can reduce the apoptosis of pancreatic islet cells and protect the pancreatic tissue of diabetic mice.

The results of the experiment of the present invention show that the expression of Caspase-3 (indicated by arrow) in the group administered with plasminogen (FIG. 15B) is remarkably lower than that in the control group administered with vehicle PBS (FIG. 15A). This indicates that plasminogen can reduce the apoptosis of pancreatic islet cells.

Example 16. Plasminogen Promotes Expression and Secretion of Insulin in 18-Week-Old Diabetic Mice Eight 18-week-old male db/db mice were weighed and randomly divided, according to body weight, into two groups, a group administered with plasminogen and a control group administered with vehicle PBS, with 4 mice in each group, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum liquid (Vector laboratories, Inc., USA) for 1 hour, and thereafter, the goat serum liquid was discarded, and the tissues were circled with a PAP pen. The sections were incubated with rabbit anti-mouse insulin antibody (Abcam) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After gradient dehydration, permeabilization and sealing, the sections were observed under a microscope at 200×.

Figure 16:
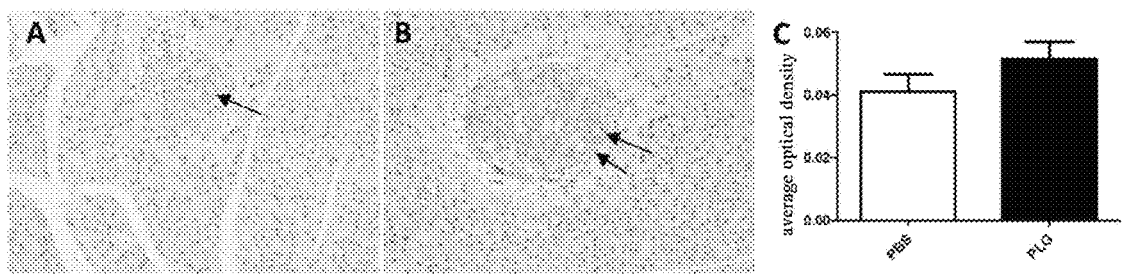
FIG. 16 shows the results of immunohistochemical staining for insulin of the pancreatic islets after administration of plasminogen to 18-week-old diabetic mice for 35 days. A represents the control group administered with vehicle PBS, B represents the group administered with plasminogen, and C represents the quantitative analysis results. The results show that the expression of insulin (indicated by arrow) in the group administered with plasminogen is remarkably higher than that in the control group administered with vehicle PBS, and the statistical difference is nearly significant (P=0.15). This indicates that plasminogen can promote repair of pancreatic islet function and promote production and secretion of insulin.

The results show that the expression of insulin (indicated by arrow) in the group administered with plasminogen (FIG. 16B) is remarkably higher than that in the control group administered with vehicle PBS (FIG. 16A), and the statistical difference is nearly significant (P=0.15) (FIG. 16C). This indicates that plasminogen can promote repair of pancreatic islet function and promote expression and secretion of insulin.

Example 17. Plasminogen Promotes Expression and Secretion of Insulin in 24- to 25-Week-Old Diabetic Mice Eight 24- to 25-week-old male db/db mice were weighed and randomly divided, according to body weight, into two groups, a group of 5 mice administered with plasminogen and a control group of 3 mice administered with vehicle PBS, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum liquid (Vector laboratories, Inc., USA) for 1 hour, and thereafter, the goat serum liquid was discarded, and the tissues were circled with a PAP pen. The sections were incubated with rabbit anti-mouse insulin antibody (Abcam) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After gradient dehydration, permeabilization and sealing, the sections were observed under a microscope at 200×.

Figure 17:
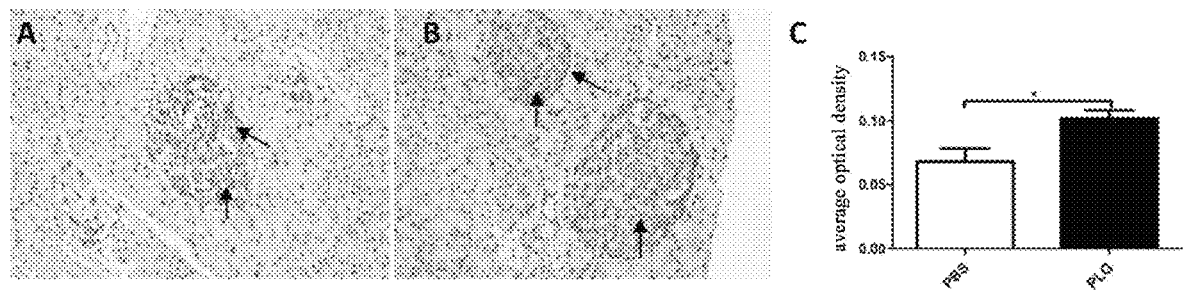
FIG. 17 shows the observed results of immunohistochemical staining for insulin of the pancreatic islets after administration of plasminogen to 24- to 25-week-old diabetic mice for 35 days. A represents the control group administered with vehicle PBS, B represents the group administered with plasminogen, and C represents the quantitative analysis results. The results show that the expression of insulin (indicated by arrow) in the group administered with plasminogen is remarkably higher than that in the control group administered with vehicle PBS, and the statistical difference is significant (* indicates P<0.05). This indicates that plasminogen can promote repair of pancreatic islet function and promote production and secretion of insulin.

The results show that the expression of insulin (indicated by arrow) in the group administered with plasminogen is remarkably higher than that in the control group administered with vehicle PBS, and the statistical difference is significant (P=0.02) (FIG. 17). This indicates that plasminogen can effectively repair the pancreatic islet function and promote expression and secretion of insulin.

Example 18. Plasminogen Promotes Repair of Insulin Synthesis and Secretion Function of Diabetic Mice Nine 26-week-old male db/db mice were weighed and randomly divided, according to body weight, into two groups, a group of 4 mice administered with plasminogen and a control group of 5 mice administered with vehicle PBS, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 35, the mice were fasted for 16 hours; and on day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum liquid (Vector laboratories, Inc., USA) for 1 hour, and thereafter, the goat serum liquid was discarded, and the tissues were circled with a PAP pen. The sections were incubated with rabbit anti-mouse insulin antibody (Abcam) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After gradient dehydration, permeabilization and sealing, the sections were observed under a microscope at 200×.

Figure 18:
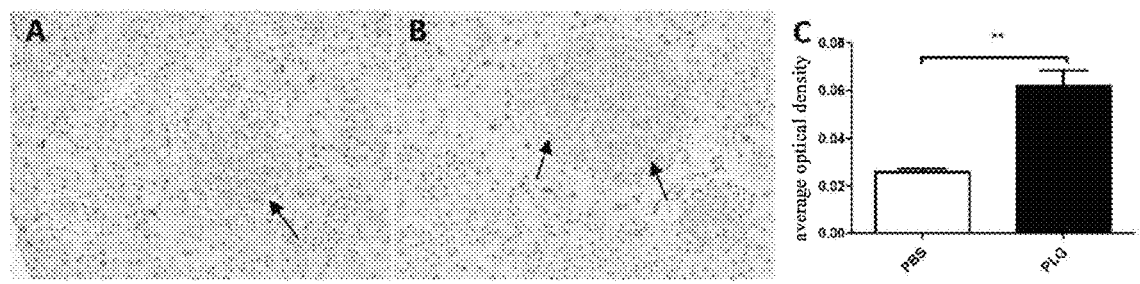
FIG. 18 shows the results of immunohistochemical staining for insulin of the pancreatic islets after administration of plasminogen to 26-week-old diabetic mice for 35 days. A represents the control group administered with vehicle PBS, B represents the group administered with plasminogen, and C represents the quantitative analysis results. The results show that the expression of insulin (indicated by arrow) in the group administered with plasminogen is remarkably higher than that in the control group administered with vehicle PBS, and the statistical difference is extremely significant (** indicates P<0.01). This indicates that plasminogen can effectively promote repair of pancreatic islet function and promote production and secretion of insulin.

The results show that the expression of insulin (indicated by arrow) in the group administered with plasminogen is remarkably higher than that in the control group administered with vehicle PBS, and the statistical difference is extremely significant (P=0.005) (FIG. 18). This indicates that plasminogen can effectively repair the pancreatic islet function of diabetic mice and improve expression and secretion of insulin.

Example 19. Plasminogen Promotes Expression of Multi-Directional Nuclear Transcription Factor NF-κB in Pancreatic Islet of 24- to 25-Week-Old Diabetic Mice Ten 24- to 25-week-old male db/db mice were weighed and randomly divided, according to body weight, into two groups, a group of 4 mice administered with plasminogen and a control group of 6 mice administered with vehicle PBS, on the day the experiment started that was recorded as day 0; in addition, four additional db/m mice were used as a normal control group and this normal control group was not treated. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum liquid (Vector laboratories, Inc., USA) for 1 hour, and thereafter, the goat serum liquid was discarded, and the tissues were circled with a PAP pen. The sections were incubated with rabbit anti-mouse NF-κB (Abcam) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After gradient dehydration, permeabilization and sealing, the sections were observed under a microscope at 200×.

NF-κB is a member of the transcription factor protein family and plays an important role in the process of repairing an inflammation[45].

Figure 19:
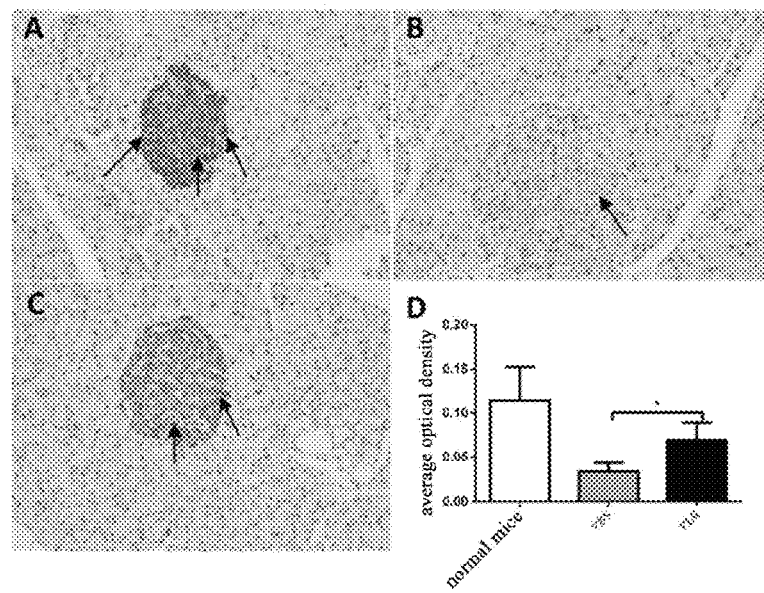
FIG. 19 shows the observed results of immunohistochemical staining for NF-κB of the pancreatic tissues after administration of plasminogen to 24- to 25-week-old diabetic mice for 31 days. A represents a normal control group, B represents the control group administered with vehicle PBS, C represents the group administered with plasminogen, and D represents the quantitative analysis results. The results show that the expression of NF-κB (indicated by arrow) in the group administered with plasminogen is remarkably higher than that in the control group administered with vehicle PBS, and the statistical difference is significant (* indicates P<0.05). This indicates that plasminogen can promote expression of multi-directional nuclear transcription factor NF-κB, thereby promoting repair of an inflammation in the pancreatic islet of 24- to 25-week-old diabetic mice.

The results of the experiment of the present invention show that the expression of NF-κB (indicated by arrow) in the group administered with plasminogen is remarkably higher than that in the control group administered with vehicle PBS, and the statistical difference is significant (FIG. 19). This indicates that plasminogen can promote expression of multi-directional nuclear transcription factor NF-κB.

Example 20. Plasminogen Reduces Proliferation of Pancreatic Islet α Cells in 18-Week-Old Diabetic Mice, Restores Normal Distribution of Pancreatic Islet α Cells and Reduces Secretion of Glucagon Eight male db/db mice and three male db/m mice, 18 weeks old, were weighed and the db/db mice were randomly divided, according to body weight, into two groups, a group administered with plasminogen and a control group administered with vehicle PBS, with 4 mice in each group, on the day the experiment started that was recorded as day 0; in addition, the db/m mice were used as a normal control group. Starting from day 1, plasminogen or PBS was administered. The mice in the group administered with plasminogen were injected with human plasminogen at a dose of 2 mg/0.2 mL/mouse/day via the tail vein, and the mice in the control group administered with vehicle PBS were injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse glucagon antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Pancreatic islet α cells synthesize and secrete glucagon, which is mainly distributed in the peripheral region of the pancreatic islet.

Figure 20:
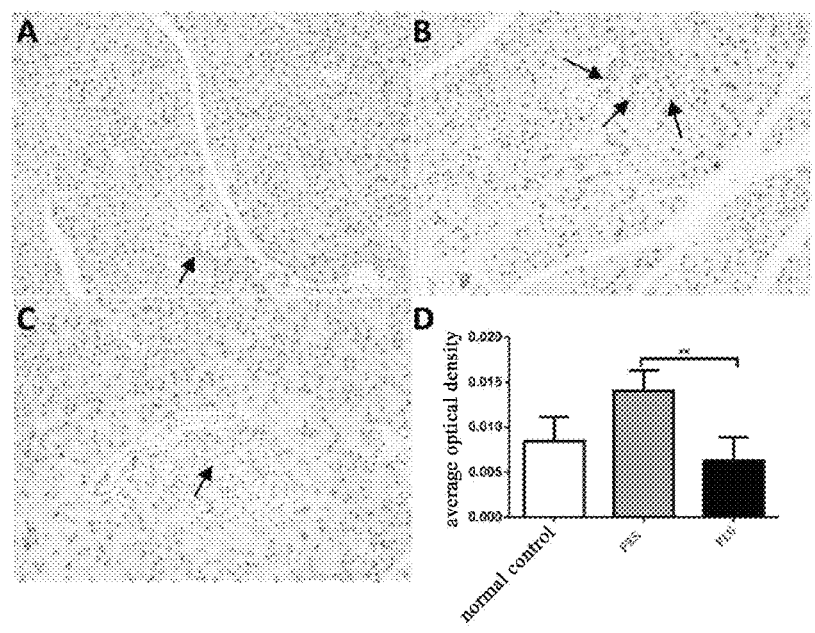
FIG. 20 shows the observed immunohistochemiscal results for glucagon of the pancreatic islets after administration of plasminogen to 18-week-old diabetic mice for 35 days. A represents a normal control group, B represents the control group administered with vehicle PBS, C represents the group administered with plasminogen, and D represents the quantitative analysis results. The results show that glucagon is expressed in the α-cell region at the periphery of the pancreatic islet in normal control mice. Compared with the group administered with plasminogen, glucagon-positive cells (indicated by arrow) in the control group administered with vehicle PBS are remarkably increased, the glucagon-positive cells infiltrate into the central region of the pancreatic islet, and the mean optical density quantitative analysis results show that the statistical difference is extremely significant (** indicates P<0.01); and glucagon-positive cells in the group administered with plasminogen are dispersed at the periphery of the pancreatic islet, and compared with the PBS group, the morphology of the pancreatic islet in the group administered with plasminogen is closer to that of normal mice. This indicates that plasminogen can significantly inhibit proliferation of pancreatic islet α cells and secretion of glucagon, and correct the disordered distribution of pancreatic islet α cells, thus promoting repair of impaired pancreatic islet.

The results show that compared with the group administered with plasminogen (FIG. 20C), glucagon-positive cells (indicated by arrow) in the control group administered with vehicle PBS (FIG. 20B) are remarkably increased, the positive cells infiltrate into the central region of the pancreatic islet, and the mean optical density quantitative analysis results show a statistical difference (** indicates P<0.01) (FIG. 20D); and glucagon-positive cells in the group administered with plasminogen are dispersed at the periphery of the pancreatic islet, and compared with the group administered with vehicle PBS, the morphology of the pancreatic islet in the group administered with plasminogen is closer to that in the normal control group (FIG. 20A). This indicates that plasminogen can significantly inhibit proliferation of pancreatic islet α cells and secretion of glucagon in 18-week-old diabetic mice, and correct the disordered distribution of pancreatic islet α cells, suggesting that plasminogen promotes repair of impaired pancreatic islet.

Example 21. Plasminogen Promotes Expression of Insulin Receptor Substrate 2 (IRS-2) in Pancreatic Islet of 18-Week-Old Diabetic Mice Seven male db/db mice and three male db/m mice, 18 weeks old, were weighed and the db/db mice were randomly divided, according to body weight, into two groups, a group of 3 mice administered with plasminogen and a control group of 4 mice administered with vehicle PBS, on the day the experiment started that was recorded as day 0; in addition, the db/m mice were used as a normal control group. Starting from day 1, plasminogen or PBS was administered. The mice in the group administered with plasminogen were injected with human plasminogen at a dose of 2 mg/0.2 mL/mouse/day via the tail vein, and the mice in the control group administered with vehicle PBS were injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse IRS-2 antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Insulin receptor substrate-2 (IRS-2) is a substrate on which an activated insulin receptor tyrosine kinase can act, is an important molecule in the insulin signal transduction pathway, and is very important for the survival of pancreatic islet β cells. IRS-2 has a protective effect on pancreatic islet β cells when the expression thereof increases and is crucial for the maintenance of functional pancreatic islet β cells[46,47].

Figure 21:
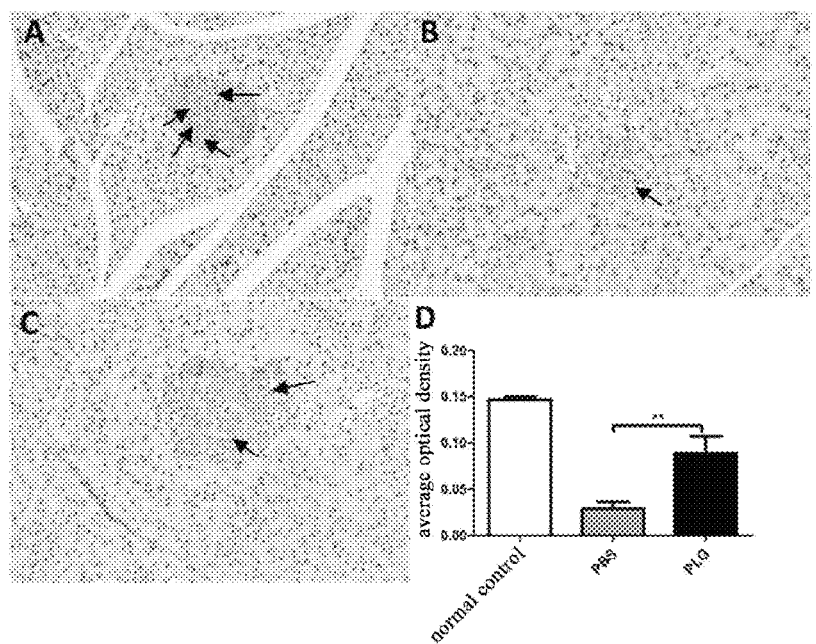
FIG. 21 shows the observed immunohistochemical results for IRS-2 of the pancreatic islet after administration of plasminogen to 18-week-old diabetic mice for 35 days. A represents a normal control group, B represents the control group administered with vehicle PBS, C represents the group administered with plasminogen, and D represents the quantitative analysis results. The results show that the positive expression of IRS-2 (indicated by arrow) in the pancreatic islets of mice in the control group administered with vehicle PBS is remarkably less than that in the group administered with plasminogen, and the statistical difference is extremely significant (** indicates P<0.01); and the expression level of IRS-2 in the group administered with plasminogen is closer to that of mice in the normal control group than that in the group administered with vehicle PBS. This indicates that plasminogen can effectively increase expression of IRS-2 in pancreatic islet cells, improve insulin signal transduction, and reduce the pancreatic islet β cell injury in diabetic mice.

The immunohistochemical results of IRS-2 show that the positive expression of IRS-2 (indicated by arrow) in the pancreatic islets of mice in the control group administered with vehicle PBS (FIG. 21B) is remarkably lower than that in the group administered with plasminogen (FIG. 21C), and the statistical difference is extremely significant (FIG. 21D); in addition, the result of the group administered with plasminogen is closer to that of the blank control group than that of the group administered with vehicle PBS (FIG. 21A).

This indicates that plasminogen can effectively increase expression of IRS-2 in pancreatic islet cells in 18-week-old diabetic mice.

Example 22. Plasminogen Promotes Expression of IRS-2 in Pancreatic Islet of 24- to 25-Week-Old Diabetic Mice Eleven male db/db mice and five male db/m mice, 24-25 weeks old, were weighed and the db/db mice were randomly divided, according to body weight, into two groups, a group of 5 mice administered with plasminogen and a control group of 6 mice administered with vehicle PBS, on the day the experiment started that was recorded as day 0; in addition, the db/m mice were used as a normal control group. Starting from day 1, plasminogen or PBS was administered. The mice in the group administered with plasminogen were injected with human plasminogen at a dose of 2 mg/0.2 mL/mouse/day via the tail vein, and the mice in the control group administered with vehicle PBS was injected with an equal volume of PBS via the tail vein or without any liquid, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse IRS-2 antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Figure 22:
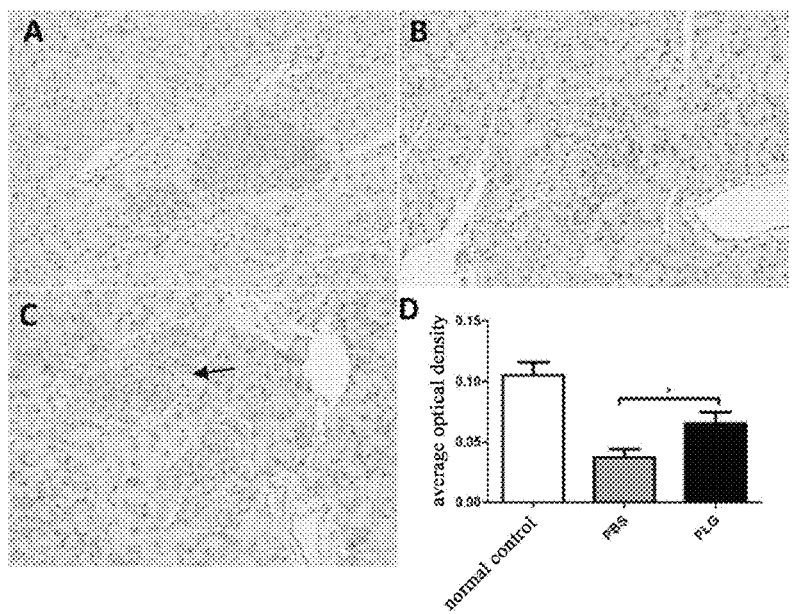
FIG. 22 shows the observed immunohistochemical results for IRS-2 of the pancreatic islets after administration of plasminogen to 24- to 25-week-old diabetic mice for 31 days. A represents a normal control group, B represents the control group administered with vehicle PBS, C represents the group administered with plasminogen, and D represents the quantitative analysis results. The results show that the positive expression of IRS-2 (indicated by arrow) in the pancreatic islets of mice in the control group administered with vehicle PBS is remarkably less than that in the group administered with plasminogen, and the statistical difference is significant (* indicates P<0.05); and the expression level of IRS-2 in the group administered with plasminogen is closer to that of mice in the normal control group than that in the group administered with vehicle PBS. This indicates that plasminogen can effectively increase expression of IRS-2 in pancreatic islet cells, improve insulin signal transduction, and reduce the pancreatic islet β cell injury in diabetic mice.

The immunohistochemical results of IRS-2 show that the positive expression of IRS-2 (indicated by arrow) in the pancreatic islets of mice in the control group administered with vehicle PBS (FIG. 22B) is remarkably lower than that in the group administered with plasminogen (FIG. 22C), and the statistical difference is significant (FIG. 22D); in addition, the result of the group administered with plasminogen is closer to that of the normal control group than that of the group administered with vehicle PBS (FIG. 22A). This indicates that plasminogen can effectively increase expression of IRS-2 in pancreatic islet cells in 24- to 25-week-old diabetic mice.

Example 23. Plasminogen Promotes Expression of IRS-2 in Pancreatic Islet of 26-Week-Old Diabetic Mice Nine male db/db mice and three male db/m mice, 26 weeks old, were weighed and the db/db mice were randomly divided, according to body weight, into two groups, a group of 4 mice administered with plasminogen and a control group of 5 mice administered with vehicle PBS, on the day the experiment started, i.e. day 0; in addition, the db/m mice were used as a normal control group. Starting from day 1, plasminogen or PBS was administered. The mice in the group administered with plasminogen were injected with human plasminogen at a dose of 2 mg/0.2 mL/mouse/day via the tail vein, and the mice in the control group administered with vehicle PBS were injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse IRS-2 antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Figure 23:
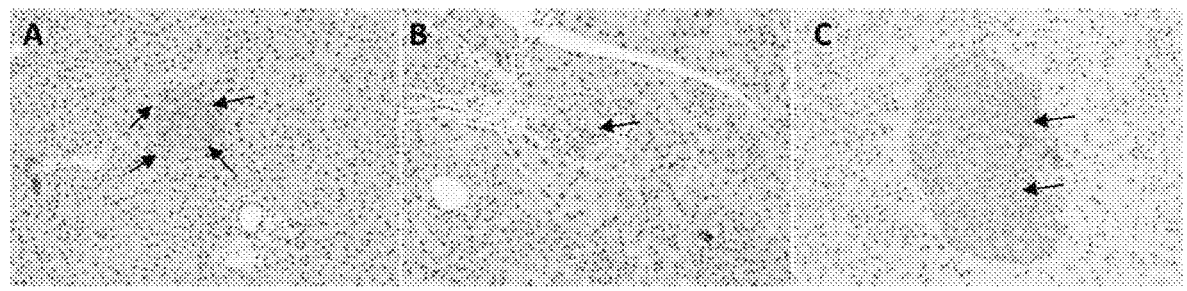
FIG. 23 shows the observed immunohistochemical results for IRS-2 of the pancreatic islet after administration of plasminogen to 26-week-old diabetic mice for 35 days. A represents a normal control group, B represents the control group administered with vehicle PBS, C represents the group administered with plasminogen, and D represents the quantitative analysis results. The results show that the positive expression of IRS-2 (indicated by arrow) in the pancreatic islets of mice in the control group administered with vehicle PBS is remarkably lower than that in the group administered with plasminogen, and the expression level of IRS-2 in the group administered with plasminogen is closer to that of mice in the normal control group than that in the group administered with vehicle PBS. This indicates that plasminogen can effectively increase expression of IRS-2 in pancreatic islet cells, improve insulin signal transduction, and reduce the pancreatic islet β cell injury in diabetic mice.

The immunohistochemical results of IRS-2 show that the positive expression of IRS-2 (indicated by arrow) in the pancreatic islets of mice in the control group administered with vehicle PBS (FIG. 23B) is remarkably lower than that in the group administered with plasminogen (FIG. 23C); and The expression level of IRS-2 in the group administered with plasminogen is closer to that of the mice in the normal control group (FIG. 23A). This indicates that plasminogen can effectively increase expression of IRS-2 in pancreatic islet cells in 26-week-old diabetic mice.

Example 24. Plasminogen Promotes Expression of IRS-2 in Pancreatic Islet of T1DM Mice with Normal PLG Activity Fifteen 9- to 10-week-old male db/db mice with normal PLG activity were randomly divided into three groups, a blank control group, a control group administered with vehicle PBS and a group administered with plasminogen, with 5 mice in each group. The mice in the group administered with vehicle PBS and the group administered with plasminogen were fasted for 4 hours and then intraperitoneally injected with 200 mg/kg STZ (Sigma, Cat #S0130), in a single dose, to induce type I diabetes mellitus[43], while the blank group was not treated. 12 days after the injection, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde.

The fixed pancreas tissues were paraffin-embedded after dehydration with alcohol gradient and permeabilization with xylene. The thickness of the tissue sections was 3 µm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse IRS-2 antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Figure 24:
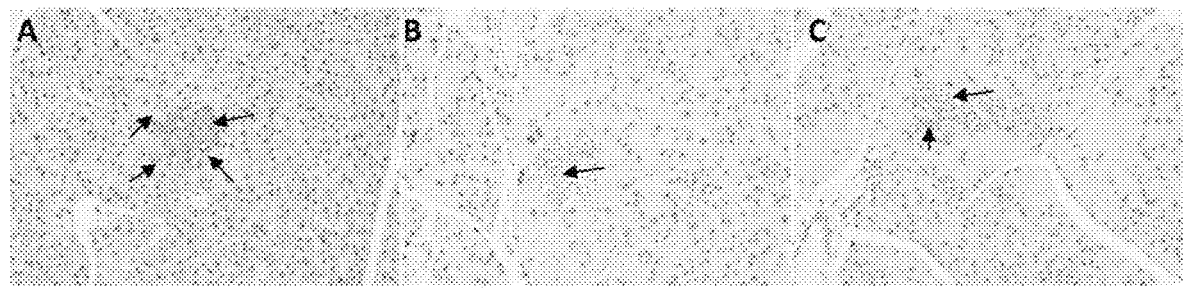
FIG. 24 shows the observed immunohistochemical results for IRS-2 of the pancreatic islet of T1DM mice with normal PLG activity after administration of plasminogen for 28 days. A represents a normal control group, B represents a control group administered with vehicle PBS, and C represents a group administered with plasminogen. The results show that the positive expression of IRS-2 (indicated by arrow) in the pancreatic islets of mice in the control group administered with vehicle PBS is remarkably lower than that in the group administered with plasminogen, and the expression level of IRS-2 in the group administered with plasminogen is closer to that of mice in the normal control group than that in the group administered with vehicle PBS. This indicates that plasminogen can effectively increase expression of IRS-2 in pancreatic islet cells, improve insulin signal transduction, and reduce the pancreatic islet β cell injury in T1DM mice with normal PLG activity.

The immunohistochemical results of IRS-2 show that the positive expression of IRS-2 (indicated by arrow) in the pancreatic islets of mice in the control group administered with vehicle PBS (FIG. 24B) is remarkably lower than that in the group administered with plasminogen (FIG. 24C), and the result of the group administered with plasminogen is closer to that of the blank control group than that of the group administered with vehicle PBS (FIG. 24A). This indicates that plasminogen can effectively increase expression of IRS-2 in pancreatic islet cells in 9- to 10-week-old mice with normal PLG activity.

Example 25. Plasminogen Reduces Infiltration of Pancreatic Islet Neutrophils in 24- to 26-Week-Old Diabetic Mice Nine male db/db mice and three male db/m mice, 24-26 weeks old, were included, wherein the db/db mice were randomly divided into two groups, a group of 4 mice administered with plasminogen and a control group of 5 mice administered with vehicle PBS, and the db/m mice were used as a normal control group. The day when the experiment began was recorded on Day 0, and the mice were weighed and grouped. From the second day of the experiment, plasminogen or PBS was administered to the mice, and the day was recorded as Day 1. The mice in the group administered with plasminogen were injected with human plasminogen at a dose of 2 mg/0.2 mL/mouse/day via the tail vein, and the mice in the control group administered with vehicle PBS were injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 µm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse neutrophil antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Neutrophils are an important member of the non-specific cellular immune system, and when inflammation occurs, they are attracted to the site of inflammation by chemotactic substances.

Figure 25:
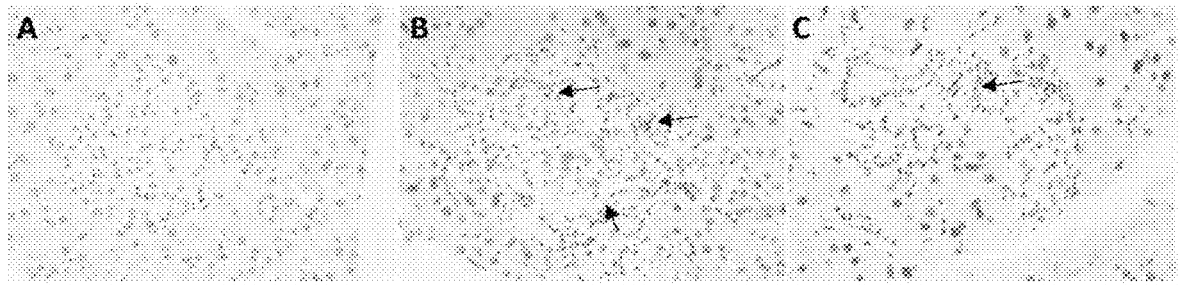
FIG. 25 shows the observed immunohistochemical results for neutrophils of the pancreatic islets after administration of plasminogen to 26-week-old diabetic mice for 35 days. A represents a normal control group, B represents a control group administered with vehicle PBS, and C represents a group administered with plasminogen. The results show that positive expression cells (indicated by arrow) in the group administered with plasminogen are less than those in the control group administered with vehicle PBS, and the result of the group administered with plasminogen is closer to that of the normal control group than that of the group administered with vehicle PBS. This indicates that plasminogen can reduce infiltration of neutrophils.

The immunohistochemical results of neutrophils show that positive expression cells in the group administered with plasminogen (FIG. 25C) are less than those in the control group administered with vehicle PBS (FIG. 25B), and the result of the group administered with plasminogen is closer to that of the normal control group (FIG. 25A) than that of the group administered with vehicle PBS.

Example 26. Plasminogen Reduces Infiltration of Pancreatic Islet Neutrophils in Mice with Impaired PLG Activity in T1DM Model Ten 9- to 10-week-old male mice with impaired PLG activity were randomly divided into three groups, a blank control group of 3 mice, a control group of 3 mice administered with PBS and a group of 4 mice administered with plasminogen. The mice in the group administered with vehicle PBS and the group administered with plasminogen were fasted for 4 hours and then intraperitoneally injected with 200 mg/kg STZ (Sigma S0130), in a single dose, to induce type I diabetes mellitus[43], while the blank group was not treated. 12 days after the injection, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 µm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse neutrophil antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 400×.

Figure 26:
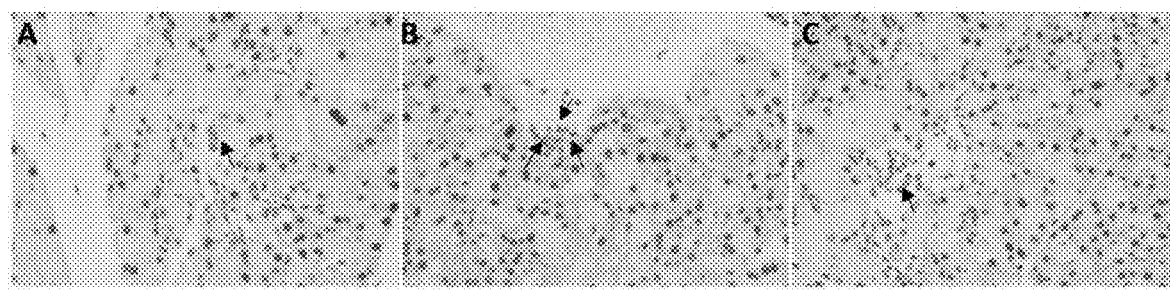
FIG. 26 shows the observed immunohistochemical results for neutrophils of the pancreatic islets after administration of plasminogen to mice with impaired PLG activity in a T1DM model for 28 days. A represents a blank control group, B represents a control group administered with vehicle PBS, and C represents a group administered with plasminogen. The results show that positive expression cells (indicated by arrow) in the group administered with plasminogen are less than those in the control group administered with vehicle PBS, and the result of the group administered with plasminogen is closer to that of the blank control group than that of the group administered with vehicle PBS. This indicates that plasminogen can reduce infiltration of pancreatic islet neutrophils in mice with impaired PLG activity in a T1DM model.

The immunohistochemical results of neutrophils show that the positive expression cells (indicated by arrow) in the group administered with plasminogen (FIG. 26C) are less than those in the control group administered with vehicle PBS (FIG. 26B), and the result of the group administered with plasminogen is closer to that of the blank control group (FIG. 26A) than that of the group administered with vehicle PBS.

Example 27. Plasminogen Reduces Infiltration of Pancreatic Islet Neutrophils in Mice with Normal PLG Activity in T1DM Model Eleven 9- to 10-week-old male mice with normal PLG activity, were randomly divided into three groups, a blank control group of 3 mice, a control group of 4 mice administered with vehicle PBS and a group of 4 mice administered with plasminogen. The mice in the group administered with vehicle PBS and the group administered with plasminogen were fasted for 4 hours and then intraperitoneally injected with 200 mg/kg STZ (Sigma S0130), in a single dose, to induce type I diabetes mellitus[43], while the blank group was not treated. 12 days after the injection, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse neutrophil antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 400×.

Figure 27:
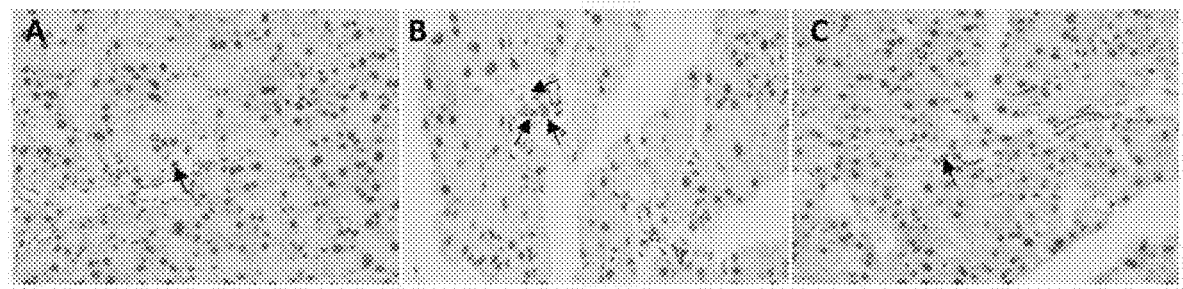
FIG. 27 shows the observed immunohistochemical results for neutrophils of the pancreatic islets after administration of plasminogen to mice with normal PLG activity in a T1DM model for 28 days. A represents a blank control group, B represents a control group administered with vehicle PBS, and C represents a group administered with plasminogen. The results show that positive expression cells (indicated by arrow) in the group administered with plasminogen are less than those in the control group administered with vehicle PBS, and the result of the group administered with plasminogen is closer to that of the blank control group than that of the group administered with vehicle PBS. This indicates that plasminogen can promote infiltration of pancreatic islet neutrophils in mice with normal PLG activity in a T1DM model.

The immunohistochemical results of neutrophils show that the positive expression cells (indicated by arrow) in the group administered with plasminogen (FIG. 27C) are less than those in the control group administered with vehicle PBS (FIG. 27B), and the result of the group administered with plasminogen is closer to that of the blank control group (FIG. 27A) than that of the group administered with vehicle PBS.

Example 28. Plasminogen Promotes Synthesis and Secretion of Insulin in Mice with Impaired PLG Activity in T1DM Model Ten 9- to 10-week-old male mice with impaired PLG activity, were randomly divided into three groups, a blank control group of 3 mice, a control group of 3 mice administered with PBS and a group of 4 mice administered with plasminogen. The mice in the group administered with vehicle PBS and the group administered with plasminogen were fasted for 4 hours and then intraperitoneally injected with 200 mg/kg STZ (Sigma S0130), in a single dose, to induce type I diabetes mellitus[43], while the blank group was not treated. 12 days after the injection, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse insulin antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Figure 28:
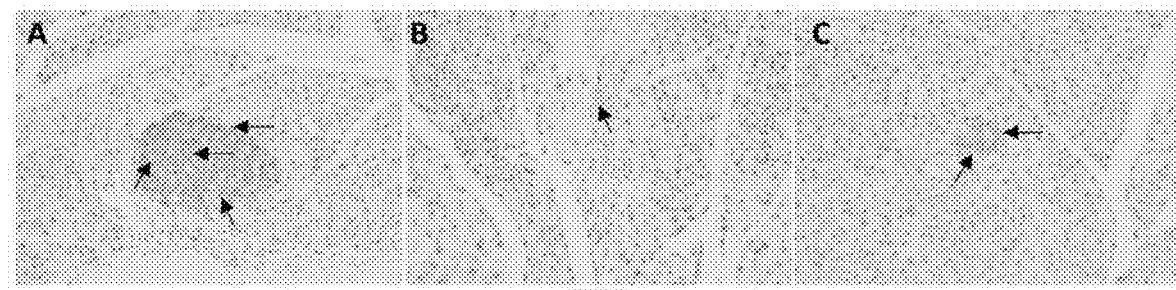
FIG. 28 shows the observed immunohistochemical results for insulin of the pancreatic islets after administration of plasminogen to mice with impaired PLG activity in a T1DM model for 28 days. A represents a blank control group, B represents a control group administered with vehicle PBS, and C represents a group administered with plasminogen. The immunohistochemical results show that the positive expression of insulin (indicated by arrow) in the group administered with plasminogen is remarkably higher than that in the control group administered with vehicle PBS, and the result of the group administered with plasminogen is closer to that of the blank control group than that of the group administered with vehicle PBS. This indicates that plasminogen can promote synthesis and secretion of insulin in mice with impaired PLG activity in a T1DM model.

The immunohistochemical results show that the positive expression of insulin (indicated by arrow) in the group administered with plasminogen (FIG. 28C) is remarkably higher than that in the control group administered with vehicle PBS (FIG. 28B), and the result of the group administered with plasminogen is closer to that of the blank control group (FIG. 28A) than that of the group administered with vehicle PBS. This indicates that plasminogen can promote synthesis and secretion of insulin in mice with impaired PLG activity in a T1DM model.

Example 29. Plasminogen Promotes Synthesis and Expression of Insulin in Mice with Normal PLG Activity in T1DM Model Eleven 9- to 10-week-old male mice with normal PLG activity, were randomly divided into three groups, a blank control group of 3 mice, a control group of 4 mice administered with vehicle PBS and a group of 4 mice administered with plasminogen. The mice in the group administered with vehicle PBS and the group administered with plasminogen were fasted for 4 hours and then intraperitoneally injected with 200 mg/kg STZ (Sigma S0130), in a single dose, to induce type I diabetes mellitus[43], while the blank group was not treated. 12 days after the injection, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse insulin antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Figure 29:
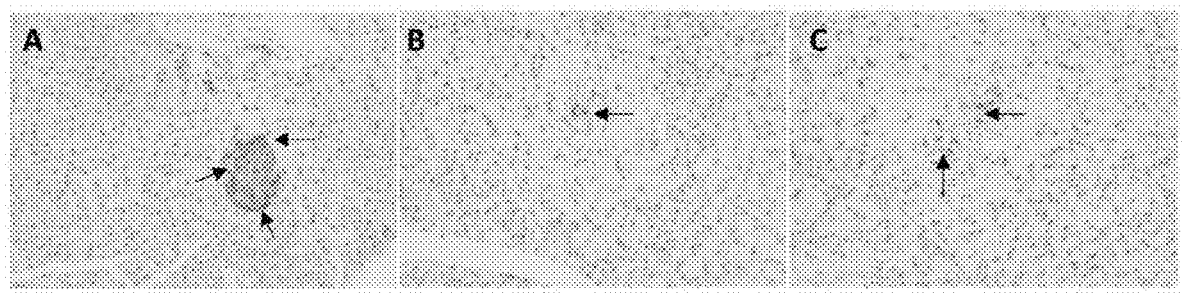
FIG. 29 shows the observed immunohistochemical results for insulin of the pancreatic islets after administration of plasminogen to mice with normal PLG activity in a T1DM model for 28 days. A represents a blank control group, B represents a control group administered with vehicle PBS, and C represents a group administered with plasminogen. The immunohistochemical results show that the positive expression of insulin (indicated by arrow) in the group administered with plasminogen is remarkably higher than that in the control group administered with vehicle PBS, and the result of the group administered with plasminogen is closer to that of the blank control group than that of the group administered with vehicle PBS. This indicates that plasminogen can promote synthesis and expression of insulin in mice with normal PLG activity in a T1DM model.

The immunohistochemical results show that the positive expression of insulin (indicated by arrow) in the group administered with plasminogen (FIG. 29C) is remarkably higher than that in the control group administered with vehicle PBS (FIG. 29B), and the result of the group administered with plasminogen is closer to that of the blank control group (FIG. 29A) than that of the group administered with vehicle PBS. This indicates that plasminogen can promote synthesis and expression of insulin in mice with normal PLG activity in a T1DM model.

Example 30. Plasminogen Promotes Expression of Multi-Directional Nuclear Transcription Factor NF-κB in Pancreatic Islet of Mice with Impaired PLG Activity in T1DM Model Ten 9- to 10-week-old male mice with impaired PLG activity, were randomly divided into three groups, a blank control group of 3 mice, a control group of 3 mice administered with PBS and a group of 4 mice administered with plasminogen. The mice in the group administered with vehicle PBS and the group administered with plasminogen were fasted for 4 hours and then intraperitoneally injected with 200 mg/kg STZ (Sigma S0130), in a single dose, to induce type I diabetes mellitus[43], while the blank group was not treated. 12 days after the injection, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse NF-κB antibody (Cell Signal) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

As a multi-directional nuclear transcription factor, NF-κB is involved in various gene regulations after being activated, such as cell proliferation, apoptosis, inflammation and immunity[24].

Figure 30:
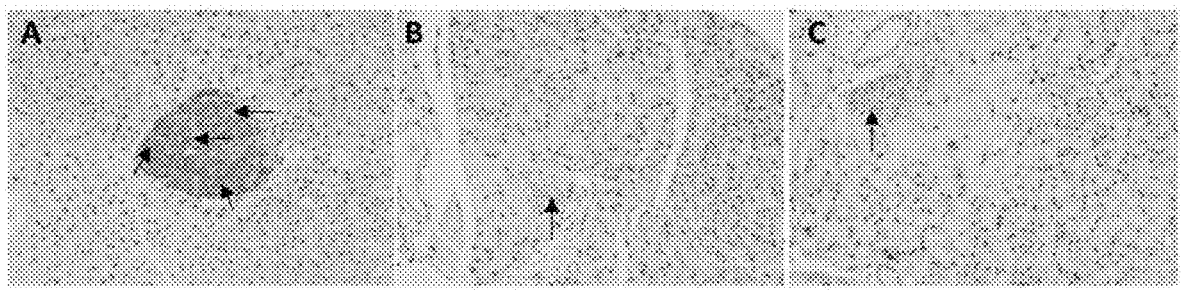
FIG. 30 shows the observed immunohistochemical results for NF-κB of the pancreatic islets after administration of plasminogen to mice with impaired PLG activity in a T1DM model for 28 days. A represents a blank control group, B represents a control group administered with vehicle PBS, and C represents a group administered with plasminogen. The results show that the expression of NF-κB (indicated by arrow) in the group administered with plasminogen is remarkably higher than that in the control group administered with vehicle PBS. This indicates that plasminogen can promote expression of inflammation repair factor NF-κB, thereby promoting repair of an inflammation in the pancreatic islet.

The experimental results show that the expression of NF-κB (indicated by arrow) in the group administered with plasminogen (FIG. 30C) is remarkably higher than that in the control group administered with vehicle PBS (FIG. 30B). This indicates that plasminogen can promote expression of multi-directional nuclear transcription factor NF-κB.

Example 31. Plasminogen Promotes Expression of Multi-Directional Nuclear Transcription Factor NF-κB in Pancreatic Islet of 18-Week-Old Diabetic Mice Seven 18-week-old male db/db mice were weighed and randomly divided, according to body weight, into two groups, a group of 3 mice administered with plasminogen and a control group of 4 mice administered with vehicle PBS, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse NF-κB antibody (Cell Signal) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Figure 31:
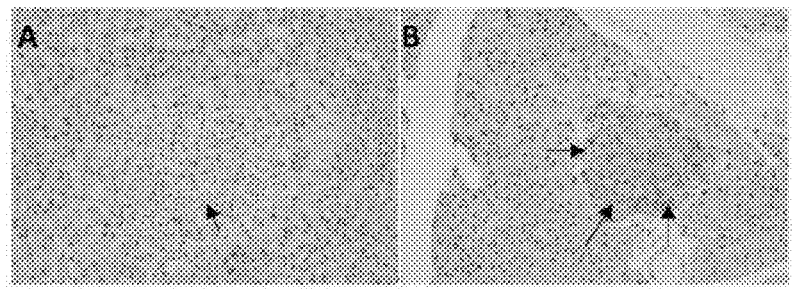
FIG. 31 shows the observed immunohistochemical results for NF-κB of the pancreatic islet after administration of plasminogen to 18-week-old diabetic mice for 35 days. A represents the control group administered with vehicle PBS, and B represents the group administered with plasminogen. The experimental results show that the expression of NF-κB (indicated by arrow) in the group administered with plasminogen is remarkably higher than that in the control group administered with vehicle PBS. This indicates that plasminogen can promote expression of multi-directional nuclear transcription factor NF-κB, thereby promoting repair of an inflammation in the pancreatic islet of relatively young (18-week-old) diabetic mice.

The results of the experiment of the present invention show that the expression of NF-κB (indicated by arrow) in the group administered with plasminogen (FIG. 31B) is remarkably higher than that in the control group administered with vehicle PBS (FIG. 31A). This indicates that plasminogen can promote expression of multi-directional nuclear transcription factor NF-κB.

Example 32. Plasminogen Inhibits Expression of Multi-Directional Nuclear Transcription Factor NF-κB in 26-Week-Old Diabetic Mice Nine male db/db mice and three male db/m mice, 26 weeks old, were weighed and the db/db mice were randomly divided, according to body weight, into two groups, a group of 4 mice administered with plasminogen and a control group of 5 mice administered with vehicle PBS, on the day the experiment started, i.e. day 0; in addition, the db/m mice were used as a normal control group. Starting from the 1st day, plasminogen or PBS was administered and this day was recorded as day 1. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse NF-κB antibody (Cell Signal) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Figure 32:
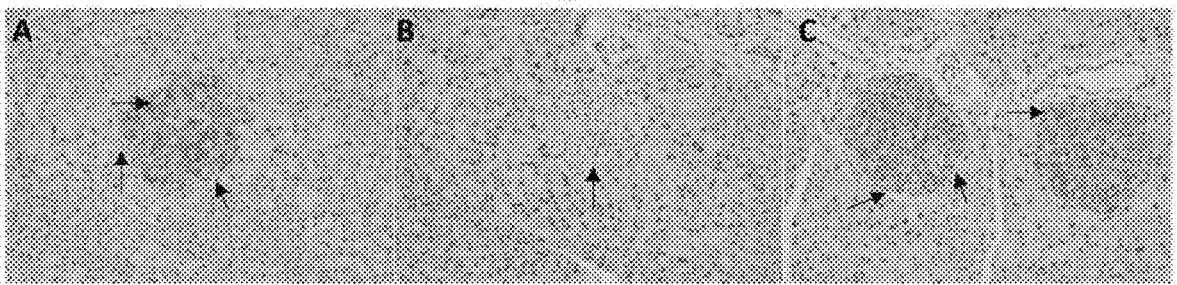
FIG. 32 shows the observed immunohistochemical results for NF-κB of the pancreatic islet after administration of plasminogen to 26-week-old diabetic mice for 35 days. A represents a normal control group, B represents a control group administered with vehicle PBS, and C represents a group administered with plasminogen. The results of the experiment of the present invention show that the expression of NF-κB (indicated by arrow) in the group administered with plasminogen is remarkably higher than that in the control group administered with vehicle PBS. This indicates that plasminogen can promote expression of multi-directional nuclear transcription factor NF-κB, thereby promoting repair of an inflammation in the pancreatic islet of relatively old (26-week-old) diabetic mice.

The experimental results show that the expression of NF-κB (indicated by arrow) in the group administered with plasminogen (FIG. 32C) is remarkably higher than that in the control group administered with vehicle PBS (FIG. 32B), and the result of the group administered with plasminogen is closer to that of the normal control group (FIG. 32A) than that of the group administered with vehicle PBS. This indicates that plasminogen can promote expression of multi-directional nuclear transcription factor NF-κB in relatively old (26-week-old) diabetic mice.

Example 33. Plasminogen Promotes Expression of TNF-α in Pancreatic Islet of 24- to 25-Week-Old Diabetic Mice Eleven male db/db mice and five male db/m mice, 24-25 weeks old, were weighed and the db/db mice were randomly divided, according to body weight, into two groups, a group of 5 mice administered with plasminogen and a control group of 6 mice administered with vehicle PBS, on the day the experiment started that was recorded as day 0; in addition, the db/m mice were used as a normal control group. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein or without any liquid, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse TNF-α antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Tumor necrosis factor-α (TNF-α) is mainly produced by activated monocytes/macrophages and is an important pro-inflammatory factor[48].

Figure 33:
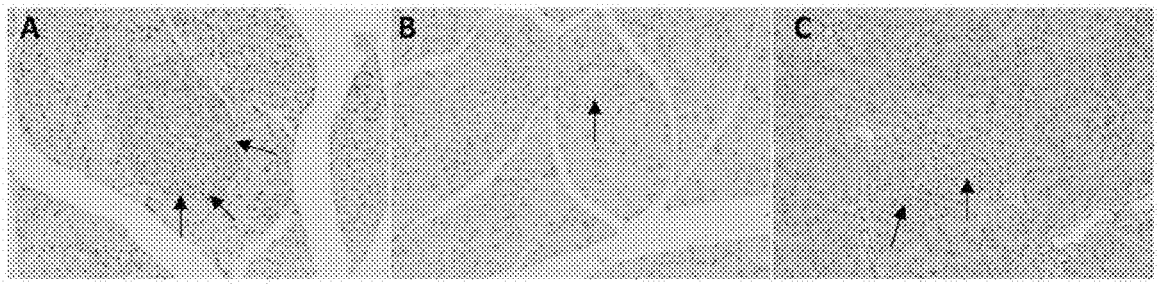
FIG. 33 shows the observed immunohistochemical results for TNF-α of the pancreatic islets after administration of plasminogen to 24- to 25-week-old diabetic mice for 31 days. A represents a normal control group, B represents a control group administered with vehicle PBS, and C represents a group administered with plasminogen. The research results show that the positive expression of TNF-α (indicated by arrow) in the group administered with plasminogen are remarkably higher than that in the control group administered with vehicle PBS, and the result of the group administered with plasminogen is closer to that of the normal control group than that of the group administered with vehicle PBS. This indicates that plasminogen can promote expression of TNF-α, thereby promoting repair of impaired pancreatic islet in 24- to 25-week-old diabetic mice.

The research results of this experiment show that the positive expression of TNF-α in the group administered with plasminogen (FIG. 33C) are remarkably higher than that in the control group administered with vehicle PBS (FIG. 33B), and the result of the group administered with plasminogen is closer to that of the normal control group (FIG. 33A) than that of the group administered with vehicle PBS. This indicates that plasminogen can promote expression of TNF-α in 24- to 25-week-old diabetic mice.

Example 34. Plasminogen Inhibits Expression of TNF-α in Pancreatic Islet of 26-Week-Old Diabetic Mice Nine male db/db mice and three male db/m mice, 26 weeks old, were weighed and the db/db mice were randomly divided, according to body weight, into two groups, a group of 4 mice administered with plasminogen and a control group of 5 mice administered with vehicle PBS, on the day the experiment started, i.e. day 0; in addition, the db/m mice were used as a normal control group. Starting from day 1, plasminogen or PBS was administered. The mice in the group administered with plasminogen were injected with human plasminogen at a dose of 2 mg/0.2 mL/mouse/day via the tail vein, and the mice in the control group administered with vehicle PBS was injected with an equal volume of PBS via the tail vein or without any liquid, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse TNF-α antibody (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Figure 34:
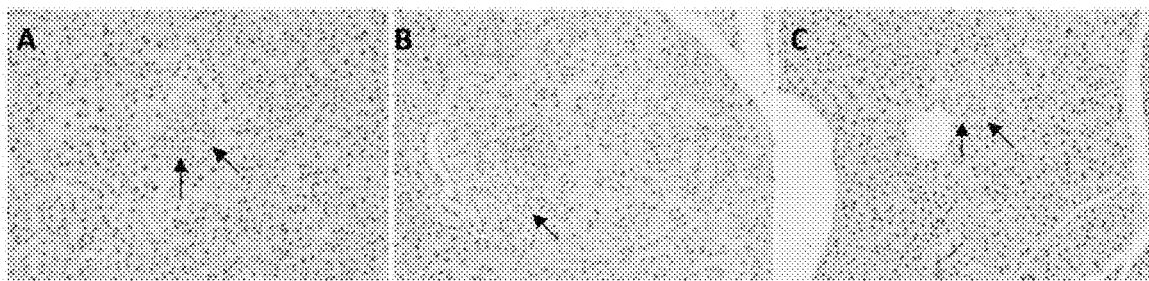
FIG. 34 shows the observed immunohistochemical results for TNF-α of the pancreatic islets after administration of plasminogen to 26-week-old diabetic mice for 31 days. A represents a normal control group, B represents a control group administered with vehicle PBS, and C represents a group administered with plasminogen. The research results show that the positive expression of TNF-α (indicated by arrow) in the group administered with plasminogen are remarkably higher than that in the control group administered with vehicle PBS, and the result of the group administered with plasminogen is closer to that of the normal control group than that of the group administered with vehicle PBS. This indicates that plasminogen can promote expression of TNF-α, thereby promoting repair of impaired pancreatic islet in 26-week-old diabetic mice.

The research results show that the positive expression of TNF-α in the group administered with plasminogen (FIG. 34C) are remarkably higher than that in the control group administered with vehicle PBS (FIG. 34B), and the result of the group administered with plasminogen is closer to that of the normal control group (FIG. 34A) than that of the group administered with vehicle PBS. This indicates that plasminogen can promote expression of TNF-α in 26-week-old diabetic mice.

Example 35. Plasminogen Promotes Expression of TNF-α in Pancreatic Islet of Mice with Impaired PLG Activity in T1DM Model Seven 9- to 10-week-old male mice with impaired PLG activity were randomly divided into two groups, a control group of 3 mice administered with PBS and a group of 4 mice administered with plasminogen. The two groups of mice were fasted for 4 hours and intraperitoneally injected with 200 mg/kg STZ (Sigma S0130), in a single dose, to induce type I diabetes mellitus[43]. 12 days after the injection, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Rabbit anti-mouse antibody TNF-α (Abcam) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Figure 35:
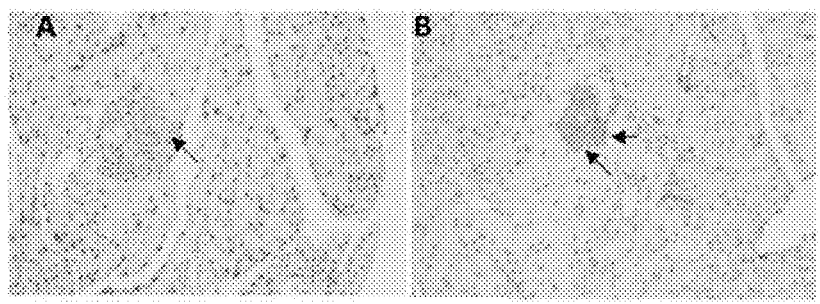
FIG. 35 shows the observed immunohistochemical results for TNF-α of the pancreatic islets after administration of plasminogen to mice with impaired PLG activity in a T1DM model for 28 days. A represents the control group administered with vehicle PBS, and B represents the group administered with plasminogen. The research results show that the positive expression of TNF-α (indicated by arrow) in the group administered with plasminogen is remarkably higher than that in the control group administered with vehicle PBS. This indicates that plasminogen can promote expression of TNF-α, thereby promoting repair of impaired pancreatic islet in mice with impaired PLG activity in a T1DM model.

The research results of this experiment show that the positive expression of TNF-α in the group administered with plasminogen (FIG. 35B) is remarkably higher than that in the control group administered with vehicle PBS (FIG. 35A).

This indicates that plasminogen can promote expression of TNF-α in mice with impaired PLG activity in a T1DM model.

Example 36. Plasminogen Alleviates Impaired Pancreatic Islet in Mice with Impaired PLG Activity in T1DM Model Ten 9- to 10-week-old male mice with impaired PLG activity, were randomly divided into three groups, a blank control group of 3 mice, a control group of 3 mice administered with PBS and a group of 4 mice administered with plasminogen. The mice in the group administered with vehicle PBS and the group administered with plasminogen were fasted for 4 hours and then intraperitoneally injected with 200 mg/kg STZ (Sigma S0130), in a single dose, to induce type I diabetes mellitus[43], while the blank group was not treated. 12 days after the injection, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Goat anti-mouse IgM (HRP) antibody (Abcam) was added to the sections dropwise, incubated for 1 hour at room temperature and washed with 0.01 M PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

IgM antibodies play an important role during the clearance of apoptotic and necrotic cells, and the local level of IgM antibodies at the injury site in tissues and organs are positively correlated with the degree of injury[49,50]. Therefore, detection of local level of IgM antibodies in tissues and organs can reflect the injury of the tissues and organs.

Figure 36:
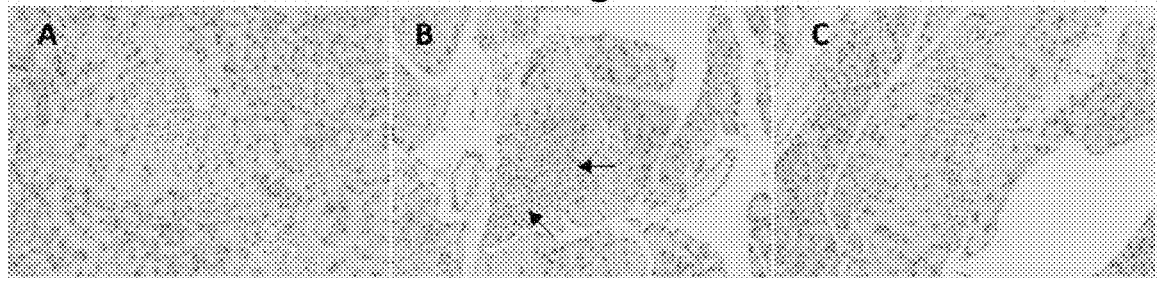
FIG. 36 shows the observed immunohistochemical results for IgM of the pancreatic islets after administration of plasminogen to mice with impaired PLG activity in a T1DM model for 28 days. A represents a blank control group, B represents a control group administered with vehicle PBS, and C represents a group administered with plasminogen. The research results of this experiment show that the positive expression of IgM (indicated by arrow) in the group administered with plasminogen is remarkably lower than that in the control group administered with vehicle PBS, and the result of the group administered with plasminogen is closer to that of the normal control group than that of the group administered with vehicle PBS. This indicates that plasminogen can reduce expression of IgM, thereby reducing impaired pancreatic islet in mice with impaired PLG activity in a T1DM model.

The research results show that the positive expression of IgM in the group administered with plasminogen (FIG. 36C) is remarkably lower than that in the control group administered with vehicle PBS (FIG. 36B), and the result of the group administered with plasminogen is closer to that of the blank control group (FIG. 36A) than that of the group administered with vehicle PBS. This indicates that plasminogen can reduce expression of IgM, suggesting that plasminogen can alleviate impaired pancreatic islet in mice with impaired PLG activity in a T1DM model.

Example 37. Plasminogen Reduces Pancreatic Islet Cell Apoptosis in 24- to 25-Week-Old Diabetic Mice Eleven male db/db mice and five male db/m mice, 24-25 weeks old, were weighed and the db/db mice were randomly divided, according to body weight, into two groups, a group of 5 mice administered with plasminogen and a control group of 6 mice administered with vehicle PBS, on the day the experiment started that was recorded as day 0; in addition, the db/m mice were used as a normal control group. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein or without any liquid, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. A tissue was circled with a PAP pen, and a proteinase K solution was added dropwise to cover the tissue, incubated at room temperature for 7 min, and washed three times with 0.01 M PBS for 3 minutes each time. A mixed liquid of reagent 1 and reagent 2 (5:45) of TUNEL kit (Roche) was added to the sections dropwise, incubated at a constant temperature of 37° C. for 40 min, and washed with 0.01 M PBS three times for 3 minutes each time. A 3% hydrogen peroxide aqueous solution (hydrogen peroxide:methanol=1:9) prepared by using methanol was added to the sections dropwise, incubated at room temperature for 20 minutes in the dark, and washed with 0.01 M PBS three times for 3 minutes each time. A tunel kit reagent 3 was added to the sections dropwise, incubated at a constant temperature of 37° C. for 30 min, and washed with 0.01 M PBS three times. A DAB kit (Vector laboratories, Inc., USA) was applied for development. After washed with water three times, counterstaining was carried out with hematoxylin for 30 seconds followed by rinsing with running water for 5 minutes. After dehydration with alcohol gradient, permeabilization with xylenehe, and sealing with a neutral gum, the sections were observed under an optical microscope at 200×.

TUNEL staining may be used to detect the breakage of nuclear DNA in tissue cells during the late stage of apoptosis.

Figure 37:
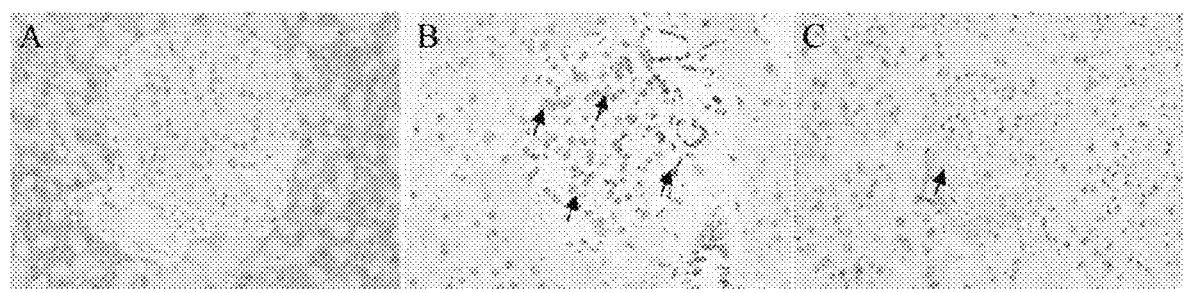
FIG. 37 shows the results of TUNEL staining of the pancreatic islets after administration of plasminogen to 24- to 25-week-old diabetic mice for 31 days. A represents a normal control group, B represents a control group administered with vehicle PBS, and C represents a group administered with plasminogen. The results of this experiment show that the number of positive cells (indicated by arrow) in the group administered with plasminogen is remarkably smaller than that in the control group administered with vehicle PBS. Positive TUNEL staining is extremely low in the normal control group. The apoptosis rate of the normal control group is about 8%, the apoptosis rate in the group administered with vehicle PBS is about 93%, and the apoptosis rate in the group administered with plasminogen is about 16%. This indicates that the plasminogen group can significantly reduce the apoptosis of pancreatic islet cells in diabetic mice.

The results of this experiment show that the number of positive cells (indicated by arrow) in the group administered with plasminogen (FIG. 37C) is remarkably smaller than that in the control group administered with vehicle PBS (FIG. 37B). Positive TUNEL staining is extremely low in the normal control group (FIG. 37A). The apoptosis rate of the normal control group is about 8%, the apoptosis rate in the group administered with vehicle PBS is about 93%, and the apoptosis rate in the group administered with plasminogen is about 16%. This indicates that the plasminogen group can significantly reduce the apoptosis of pancreatic islet cells in diabetic mice.

Example 38. Plasminogen Improves Secretion of Insulin in T1DM Model Mice

Six 9- to 10-week-old male C57 mice were randomly divided into two groups, a control group administered with vehicle PBS and a group administered with plasminogen, with 3 mice in each group. The two groups of mice were fasted for 4 hours and intraperitoneally injected with 200 mg/kg streptozotocin (STZ) (Sigma S0130), in a single dose, to induce T1DM[43]. 12 days after the injection of STZ, administration was carried out and this day was set as administration day 1. The group administered with plasminogen was injected with human plasmin at a dose of 1 mg/0.1 mL/mouse/day via the tail vein, and the control group administered with vehicle PBS was injected with an equal volume of PBS via the tail vein. Administration was carried out for 20 consecutive days. On day 21, the mice were fasted for 6 hours, and then, blood was taken from venous plexus in the eyeballs, the blood was centrifuged to obtain a supernatant, and the concentration of serum insulin was detected using an insulin detection kit (Mercodia AB) according to operating instructions.

Figure 38:
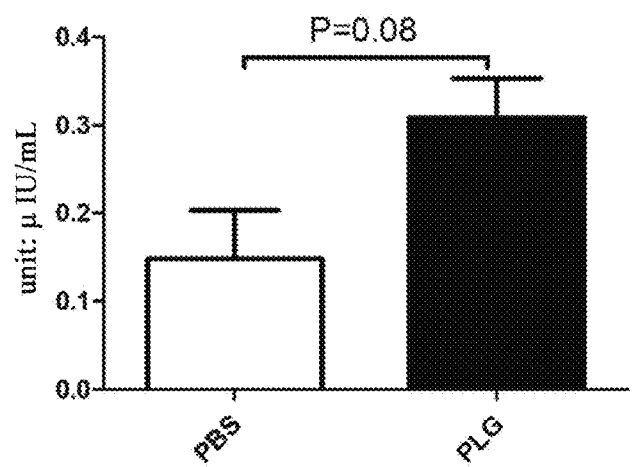
FIG. 38 shows detection results of serum insulin after administration of plasminogen to mice in a T1DM model for 20 days. The results show that the concentration of serum insulin in the mice in the control group administered with vehicle PBS is remarkably lower than that of the mice in the group administered with plasminogen, and the statistical difference is nearly significant (P=0.08). This indicates that plasminogen can promote secretion of insulin in T1DM mice.

The results show that the concentration of insulin in the mice in the control group administered with vehicle PBS is remarkably lower than that of the mice in the group administered with plasminogen, and the statistical difference is nearly significant (P=0.08) (FIG. 38). This indicates that plasminogen can promote secretion of insulin in T1DM mice.

REFERENCES

[1] International Diabetes Federation. IDF diabetes atlas [M]. 7th ed. Brussels: Karakas Print, 2015: 13.
[2] Lopez A P, de Dios A, Chiesa I, et al. Analysis of mutations in the glucokinase gene in people clinically characterized as MODY2 without a family history of diabetes. Diabetes Res Clin Pract, 2016, 118: 38-43.
[3] Fan M, Li W, Wang L, et al. Association of SLC30A8 gene polymorphism with type 2 diabetes, evidence from 46 studies: a meta-analysis. Endocrine, 2016, 53: 381-94.
[4] Liang J, Slingerland JM1 Multiple roles of the PI3K/PKB (Akt) pathway in cell cycle progress ion[J]. Cell Cycle, 2003, 2(4):339-451.
[5] Dhand R, Hiles I, Panayotou G, et al. PI3-kinase is a dual specificity enzyme: autoregulation by an intrinsic protein-serine kinase activity[J]. Em bo J, 1994,13(3):522-331.
[6] Perrin A J, Gunda M, Yu B, Yen K, Ito S, Forster S, Tissenbaum H A, Derry W B. Noncanonical control of C. elegans germline apoptosis by the insulin/IGF-1 and Ras/MAPK signaling pathways. Cell Death Differ. 2013 January; 20(1):97-107.
[7] Aguirre V, Uchida T, Yenush L, et al. Thec-Jun N H (2)-terminal kinase promotes insulin resistance during association with insulin receptor substrate-1 and phosphorylation of ser(307)[J]. J Biol Chem, 2000, 275:9047-9054.
[8] Hirosumi J, Tuneman G, Chang L, et al. A central or lefor JNKi no besity and insulin resistance. Natuer[J]. 2002, 420:333-336.
[9] Hotamisligil G S, Shargill N S, Spiegelman B M. Adipose expression of tumor necrosis factor-alpha: direct role in obesity-linked insulin resistance [J]. Science, 1993, 259(5091): 87-91.
[10] Hotamisligil G S. Inflammation and metabolic disorders[J]. Nature, 2006, 444(7121): 860-867.
[11] Swaroop J J, Rajarajeswari D, Naidu J N. Association of TNF-α with insulin resistance in type 2 diabetes mellitus[J]. Indian J Med Res, 2012, 135: 127-130.
[12] Kentish S J, O'Donnell T A, Isaacs N J, et al. Gastricvagal afferent modulation by leptin is influenced by food intake status[J]. J Physiol, 2013, 591(7): 1921-1934.
[13] Keane K N, Cruzat V F, Carlessi R, de Bittencourt P I Jr, Newsholme P. Molecular Events Linking Oxidative Stress and Inflammation to Insulin Resistance and β-Cell Dysfunction. Oxid Med Cell Longev. 2015; 2015:181643
[14] LUOTOLA K, PIETIL A, ZELLER T, et al. Associations between interleukin-1 (IL-1) gene variations or IL-1 receptor antagonist levels and the development of type 2 diabetes[J]. J Intern Med, 2011, 269(3):322-332.
[15] DONATH M Y, SHOELSON S E. Type 2 diabetes as an inflammatory disease[J]. Nature Reviews Immunology, 2011, 11(2):98-107.
[16] Reddy V P, Zhu X, Perry G, Smith M A. Oxidative stress in diabetes and Alzheimer's disease. J Alzheimers Dis 2009; 16(4): 763-774.
[17] Nishikawa T, Araki E. Impact of mitochondrial ROS production in the pathogenesis of diabetes mellitus and its complications. Antioxid Redox Signal 2007; 9(3): 343-353.
[18] Ceretta L B, Reus G Z, Abelaira H M, Ribeiro K F, Zappellini G, Felisbino F F, Steckert A V, Dal-Pizzol F, Quevedo J. Increased oxidative stress and imbalance in antioxidant enzymes in the brains of alloxan-induced diabetic rats. Exp Diabetes Res 2012; 2012: 302682.
[19] Kajimoto Y, Kaneto H. Role of oxidative stress in pancreatic 17 beta-cell dysfunction. Ann N Y Acad Sci 2004; 1011: 168-176.
[20] Valko M, Leibfritz D, Moncol J, Cronin M T, Mazur M, 18 Telser J. Free radicals and antioxidants in normal physiological functions and human disease. Int J Biochem Cell Biol 2007; 39(1): 44-84.
[21] Drews G, Krippeit-Drews P, Dufer M. Oxidative stress and 19 beta-cell dysfunction. Pflugers Arch 2010; 460(4): 703-718.
[22] Patel S, Santani D. Role of NF-κB in the pathogenesis of diabetes and its associated complications. Pharmacol Rep 2009; 61: 595-603.
[23] Hayden M R, Sowers J R. Isletopathy in type 2 diabetes mellitus: implications of islet RAS, islet fibrosis, islet amyloid, remodeling, and oxidative stress. Antioxid Redox Signal 2007; 9(7): 891-910.
[24] Mariappan N, Elks C M, Sriramula S, Guggilam A, Liu Z, Borkhsenious O, Francis J. NF-kappaB-induced oxidative stress contributes to mitochondrial and cardiac dysfunction in type II diabetes. Cardiovasc Res 2010; 85(3): 473-483.
[25] Hofmann M A, Schiekofer S, Isermann B, Kanitz M, Henkels M, Joswig M, Treusch A, Morcos M, Weiss T, Borcea V, Khalek A, Amiral J, Tritschler H, Ritz E, Wahl P, Ziegler R, Bierhaus A, Nawroth P P. Peripheral blood mononuclear cells isolated from patients with diabetic nephropathy show increased activation of the oxidative-stress sensitive transcription factor NF-κB. Diabetologia 1999; 42(2): 222-232.
[26] Eldor R, Yeffet A, Baum K, Doviner V, Amar D, Ben-Neriah Y, Christofori G Peled A, Carel J C, Boitard C, Klein T, Serup P, Eizirik D L, Melloul D. Conditional and specific NF-kappaB blockade protects pancreatic beta cells from diabetogenic agents. Proc Natl Acad Sci USA 2006; 103(13): 5072-5077.
[27] Caamano J, Hunter C A. NF-kappaB family of transcription factors: central regulators of innate and adaptive immune functions. Clin Microbiol Rev 2002; 15(3): 414-429.
[28] Lacraz G, Giroix M H, Kassis N, Coulaud J, Galinier A, Noll C, Cornut M, Schmidlin F, Paul J L, Janel N, Irminger J C, Kergoat M, Portha B, Donath M Y, Ehses J A, Homo-Delarche E Islet endothelial activation and oxidative stress gene expression is reduced by IL-1Ra treatment in the type 2 diabetic GK rat. PLoS One 2009; 4(9): e6963.
[29] Cheng C Y, Hsieh H L, Sun C C, Lin C C, Luo S F, Yang C M. IL-1 beta induces urokinase-plasminogen activator expression and cell migration through PKC alpha, JNK1/2, and NF-kappaB in A549 cells. J Cell Physiol 2009; 219(1):183-193.
[30] Mahadev K, Motoshima H, Wu X, Ruddy J M, Arnold R S, Cheng G, Lambeth J D, Goldstein B J. The NAD (P)H oxidase homolog Nox4 modulates insulin-stimulated generation of H2O2 and plays an integral role in insulin signal transduction. Mol Cell Biol 2004; 24(5): 1844-1854.
[31] Goldstein B J, Mahadev K, Wu X. Insulin action is facilitated by insulin-stimulated reactive oxygen species with multiple potential signaling targets. Diabetes 2005; 54(2): 311-321.
[32] Mahadev K, Wu X, Zilbering A, Zhu L, Lawrence J T R, Goldstein B J. Hydrogen peroxide generated during cellular insulin stimulation is integral to activation of the distal insulin signaling cascade in 3T3-L1 adipocytes. J Biol Chem 2001; 276: 48662-48669.
[33] Loh K, et al., Reactive oxygen species enhance insulin sensitivity. Cell Metab 2009; 10(4): 260-272.
[34] Nishikawa T, Araki E. Impact of mitochondrial ROS production in the pathogenesis of diabetes mellitus and its complications. Antioxid Redox Signal 2007; 9(3): 343-353.
[35] Evans J L, Goldfine I D, Maddux B A, Grodsky G M. Are oxidative stress-activated signaling pathways mediators of insulin resistance and beta-cell dysfunction? Diabetes 2003; 52(1): 1-8.
[36] Brownlee M. The pathobiology of diabetic complications: a unifying mechanism. Diabetes 2005; 54(6): 1615-1625.
[37] Henriksen E J, Diamond-Stanic M K, Marchionne E M. Oxidative stress and the etiology of insulin resistance and type 2 diabetes. Free Radic Biol Med 2011; 51(5): 993-999.
[38] Wang J, Ma H, Tong C, Zhang H, Lawlis G B, Li Y, Zang M, Ren J, Nijland M J, Ford S P, Nathanielsz P W, Li J. Overnutrition and maternal obesity in sheep pregnancy alter the JNK-IRS-1 signaling cascades and cardiac function in the fetal heart. FASEB J 2010; 24(6): 2066-2076.

[39] Marder V J, Novokhatny V. Direct fibrinolytic agents: biochemical attributes, preclinical foundation and clinical potential [J]. Journal of Thrombosis and Haemostasis, 2010, 8(3): 433-444.

[40] Hunt J A, Petteway Jr S R, Scuderi P, et al. Simplified recombinant plasmin: production and functional comparison of a novel thrombolytic molecule with plasma-derived plasmin [J]. Thromb Haemost, 2008, 100(3): 413-419.

[41] Sottrup-Jensen L, Claeys H, Zajdel M, et al. The primary structure of human plasminogen: Isolation of two lysine-binding fragments and one "mini"-plasminogen (MW, 38,000) by elastase-catalyzed-specific limited proteolysis [J]. Progress in chemical fibrinolysis and thrombolysis, 1978, 3: 191-209.

[42] Nagai N, Demarsin E, Van Hoef B, et al. Recombinant human microplasmin: production and potential therapeutic properties [J]. Journal of Thrombosis and Haemostasis, 2003, 1(2): 307-313.

[43] Brian L. Furman. Streptozotocin-Induced Diabetic Models UNIT 5.47 in Mice and Rats. Curr. Protoc. Pharmacol. 70:5.47.1-5.47.20.

[44] Parvesh Chaudhry, Mohan Singh, Sophie Parent et al. Prostate Apoptosis Response 4 (Par-4), a Novel Substrate of Caspase-3 during Apoptosis Activation. Mol Cell Biol. 2012 February; 32(4): 826-839.

[45] Patrick Viatour, Marie-Paule Merville, Vincent Bours et al. Phosphorylation of NF-kB and IkBproteins: implications in cancer and inflammation. TRENDS in Biochemical Sciences, 2005, 30 (1):43-52.

[46] Withers D J, Gutierrez J S, Towery H, et al. Disruption of IRS-2 causes type 2 diabetes in mice. Nature 1998; 391:900-904.

[47] Withers D J, Burks D J, Towery H H et al. White M F. Irs-2 coordinates Igf-1 receptor-mediated beta-cell development and peripheral insulin signalling. Nat Genet 1999; 23:32-40.

[48] Jacob CO1, Aiso S, Michie S A, McDevitt H O et al. Prevention of diabetes in nonobese diabetic mice by tumor necrosis factor (TNF): similarities between TNF-alpha and interleukin 1. Proc Natl Acad Sci USA. 1990 February; 87(3):968-72.

[49] Zhang M, Takahashi K, Alicot E M, Vorup-Jensen T, Kessler B, et al. Activation of the lectin pathway by natural IgM in a model of ischemia/reperfusion injury. J Immunol. 2006. 177: 4727-4734.

[50] Kim S J, Gershov D, Ma X, Brot N, Elkon K B (2002) I-PLA2 Activation during Apoptosis Promotes the Exposure of Membrane Lysophosphatidylcholine Leading to Binding by Natural Immunoglobulin M Antibodies and Complement Activation. The Journal of Experimental Medicine 196: 655-665.

[51] Ghinwa Barakat, Mohamed E Moustafa, Ibrahim Khalifeh ea al. Effects of exendin-4 and selenium on the expression of GLP-1R, IRS-1, and preproinsulin in the pancreas of diabetic rats. J Physiol Biochem. 2017 Jun. 7.

The invention claimed is:

1. A method for reducing blood glucose in a diabetic subject, comprising administering an effective amount of plasminogen to the subject, thereby reducing blood glucose in the subject.

2. The method of claim 1, wherein the blood glucose is selected from one or more of: a serum glucose level, a serum fructosamine level, and a serum glycated hemoglobin level.

3. The method of claim 1, wherein the diabetes mellitus is T1DM or T2DM.

4. The method of claim 1, wherein the plasminogen is administered in combination with one or more other drugs or therapies.

5. The method of claim 4, wherein the plasminogen is administered in combination with one or more drugs selected from anti-diabetic drugs, drugs against cardiovascular and cerebrovascular diseases, anti-thrombotic drugs, anti-hypertensive drugs, antilipemic drugs, anticoagulant drugs, and anti-infective drugs.

6. The method of claim 1, wherein the plasminogen has at least 75%, 80%, 85%, 90%, 95%, 96%, 97%, 98% or 99% sequence identity with SEQ ID NO. 2, and still has the plasminogen activity.

7. The method of claim 1, wherein the plasminogen is a protein that comprises a plasminogen active fragment and still has the plasminogen activity.

8. The method of claim 1, wherein the plasminogen is selected from Glu-plasminogen, Lys-plasminogen, mini-plasminogen, micro-plasminogen, delta-plasminogen or their variants that retain the plasminogen activity.

9. The method of claim 1, wherein the plasminogen is a natural or synthetic human plasminogen.

10. The method of claim 1, wherein the plasminogen is administered to the subject at a dosage of 1-100 mg/kg.

11. The method of claim 10, wherein the dosage of the plasminogen is repeated at least once.

12. The method of claim 10, wherein the plasminogen is administered at least daily.

13. The method of claim 1, wherein the subject is human.

14. A method for treating diabetes mellitus in a subject, comprising administering an effective amount of plasminogen to the subject to reduce secretion of glucagon in the subject after eating, wherein the plasminogen achieves a return to a normal or nearly normal level of blood glucose in the subject by promoting expression and/or secretion of insulin while reducing expression and/or secretion of glucagon in the subject, thereby treating diabetes mellitus in the subject.

15. The method of claim 14, wherein the blood glucose is postprandial blood glucose.

16. A method for promoting the utilization of glucose in a diabetic subject, comprising administering an effective amount of plasminogen to the subject, thereby promoting the utilization of glucose in the subject.

17. The method of claim 16, wherein the plasminogen improves the glucose tolerance in the diabetic subject.

18. A method for treating diabetes mellitus in a subject, comprising administering an effective amount of plasminogen to the subject to reduce secretion of glucagon in the subject after eating, wherein the plasminogen promotes expression and/or secretion of insulin while reducing expression and/or secretion of glucagon in the subject, thereby treating diabetes mellitus in the subject.

* * * * *

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial sequence
<220> FEATURE:
<223> OTHER INFORMATION: nucleotide sequence coding for the natural
      plasminogen(Glu-PLG,Glu-plasminogen)without the signal peptide

<400> SEQUENCE: 1
gagcctctgg atgactatgt gaatacccag ggggcttcac tgttcagtgt cactaagaag     60
cagctgggag caggaagtat agaagaatgt gcagcaaaat gtgaggagga cgaagaattc    120
acctgcaggg cattccaata tcacagtaaa gagcaacaat gtgtgataat ggctgaaaac    180
aggaagtcct ccataatcat taggatgaga gatgtagttt tatttgaaaa gaaagtgtat    240
ctctcagagt gcaagactgg gaatggaaag aactacagag ggacgatgtc caaaacaaaa    300
aatggcatca cctgtcaaaa atggagttcc acttctcccc acagacctag attctcacct    360
gctacacacc cctcagaggg actggaggag aactactgca ggaatccaga caacgatccg    420
caggggccct ggtgctatac tactgatcca gaaaagagat atgactactg cgacattctt    480
gagtgtgaag aggaatgtat gcattgcagt ggagaaaact atgacggcaa aatttccaag    540
accatgtctg gactggaatg ccaggcctgg gactctcaga gcccacacgc tcatggatac    600
attccttcca aatttccaaa caagaacctg aagaagaatt actgtcgtaa ccccgatagg    660
gagctgcggc cttggtgttt caccaccgac cccaacaagc gctgggaact ttgtgacatc    720
ccccgctgca acacaaccctcc accatcttct ggtcccacct accagtgtct gaagggaaca    780
ggtgaaaact atcgcgggaa tgtggctgtt accgtgtccg ggcacacctg tcagcactgg    840
agtgcacaga cccctcacac acataacagg acaccagaaa acttcccctg caaaaatttg    900
```

```
gatgaaaact actgccgcaa tcctgacgga aaaagggccc catggtgcca tacaaccaac    960
agccaagtgc ggtgggagta ctgtaagata ccgtcctgtg actcctcccc agtatccacg   1020
gaacaattgg ctcccacagc accacctgag ctaaccctg tggtccagga ctgctaccat    1080
ggtgatggac agagctaccg aggcacatcc tccaccacca cacaggaaa gaagtgtcag    1140
tcttggtcat ctatgacacc acaccggcac cagaagaccc cagaaaacta cccaaatgct   1200
ggcctgacaa tgaactactg caggaatcca gatgccgata aaggccctg gtgttttacc    1260
acagacccca gcgtcaggtg ggagtactgc aacctgaaaa aatgctcagg aacagaagcg   1320
agtgttgtag cacctccgcc tgttgtcctg cttccagatg tagagactcc ttccgaagaa   1380
gactgtatgt ttgggaatgg gaaaggatac cgaggcaaga gggcgaccac tgttactggg   1440
acgccatgcc aggactgggc tgcccaggag ccccatagac acagcatttt cactccagag   1500
acaaatccac gggcgggtct ggaaaaaaat tactgccgta accctgatgg tgatgtaggt   1560
ggtccctggt gctacacgac aaatccaaga aaactttacg actactgtga tgtccctcag   1620
tgtgcggccc cttcatttga ttgtgggaag cctcaagtgg agccgaagaa atgtcctgga   1680
agggttgtag gggggtgtgt ggcccaccca cattcctggc cctggcaagt cagtcttaga   1740
acaaggtttg aatgcactt ctgtggaggc accttgatat ccccagagtg ggtgttgact    1800
gctgcccact gcttggagaa gtccccaagg ccttcatcct acaaggtcat cctgggtgca   1860
caccaagaag tgaatctcga accgcatgtt caggaaatag aagtgtctag gctgttcttg   1920
gagcccacac gaaaagatat tgccttgcta aagctaagca gtcctgccgt catcactgac   1980
aaagtaatcc cagcttgtct gccatcccca aattatgtgg tcgctgaccg gaccgaatgt   2040
ttcatcactg gctggggaga acccaaggt acttttggag ctggccttct caaggaagcc   2100
cagctccctg tgattgagaa taaagtgtgc aatcgctatg agtttctgaa tggaagagtc   2160
caatccaccg aactctgtgc tgggcatttg gccggaggca ctgacagttg ccaggtgac   2220
agtggaggtc ctctggtttg cttcgagaag gacaaataca ttttacaagg agtcacttct   2280
tggggtcttg gctgtgcacg cccaataag cctggtgtct atgttcgtgt tcaaggttt    2340
gttacttgga ttgagggagt gatgagaaat aattaa                             2376
```

<210> SEQ ID NO 2
<211> LENGTH: 791
<212> TYPE: PRT
<213> ORGANISM: Artificial sequence
<220> FEATURE:
<223> OTHER INFORMATION: amino acid sequence of the natural plasminogen
      (Glu-PLG,Glu-plasminogen) without the signal peptide

<400> SEQUENCE: 2

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

-continued

```
Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
            115                 120                 125

Glu Glu Asn Tyr Cys Arg Asn Pro Asp Asn Asp Pro Gln Gly Pro Trp
        130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
            405                 410                 415

Trp Cys Phe Thr Thr Asp Pro Ser Val Arg Trp Glu Tyr Cys Asn Leu
        420                 425                 430

Lys Lys Cys Ser Gly Thr Glu Ala Ser Val Val Ala Pro Pro Pro Val
    435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
```

```
            515                 520                 525
Pro Arg Lys Leu Tyr Asp Tyr Cys Asp Val Pro Gln Cys Ala Ala Pro
            530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
            595                 600                 605

Pro Arg Pro Ser Ser Tyr Lys Val Ile Leu Gly Ala His Gln Glu Val
            610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
                660                 665                 670

Val Val Ala Asp Arg Thr Glu Cys Phe Ile Thr Gly Trp Gly Glu Thr
            675                 680                 685

Gln Gly Thr Phe Gly Ala Gly Leu Leu Lys Glu Ala Gln Leu Pro Val
690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
                740                 745                 750

Tyr Ile Leu Gln Gly Val Thr Ser Trp Gly Leu Gly Cys Ala Arg Pro
            755                 760                 765

Asn Lys Pro Gly Val Tyr Val Arg Val Ser Arg Phe Val Thr Trp Ile
770                 775                 780

Glu Gly Val Met Arg Asn Asn
785                 790

<210> SEQ ID NO 3
<211> LENGTH: 2433
<212> TYPE: DNA
<213> ORGANISM: Artificial sequence
<220> FEATURE:
<223> OTHER INFORMATION: nucleotide sequence coding for the natural
      plasminogen(from swiss prot)with the signal peptide

<400> SEQUENCE: 3
atggaacata aggaagtggt tcttctactt cttttatttc tgaaatcagg tcaaggagag        60
cctctggatg actatgtgaa tacccagggg gcttcactgt tcagtgtcac taagaagcag      120
ctgggagcag gaagtataga agaatgtgca gcaaaatgtg aggaggacga agaattcacc      180
tgcagggcat ccaatatcca gtaaaagag caacaatgtg tgataatggc tgaaaacagg      240
aagtcctcca taatcattag gatgagagat gtagttttat ttgaaaagaa agtgtatctc      300
tcagagtgca agactgggaa tggaaagaac tacagaggga cgatgtccaa aacaaaaaat      360
ggcatcacct gtcaaaaatg gagttccact tctccccaca gacctagatt ctcacctgct      420
acacacccct cagagggact ggaggagaac tactgcagga atccagacaa cgatccgcag      480
```

```
gggccctggt gctatactac tgatccagaa aagagatatg actactgcga cattcttgag    540
tgtgaagagg aatgtatgca ttgcagtgga gaaaactatg acggcaaaat ttccaagacc    600
atgtctggac tggaatgcca ggcctgggac tctcagagcc cacacgctca tggatacatt    660
ccttccaaat ttccaaacaa gaacctgaag aagaattact gtcgtaaccc cgatagggag    720
ctgcggcctt ggtgtttcac caccgacccc aacaagcgct gggaactttg tgacatcccc    780
cgctgcacaa cacctccacc atcttctggt cccacctacc agtgtctgaa gggaacaggt    840
gaaaactatc gcgggaatgt ggctgttacc gtgtccgggc acacctgtca gcactggagt    900
gcacagaccc ctcacacaca taacaggaca ccagaaaact tcccctgcaa aaatttggat    960
gaaaactact gccgcaatcc tgacggaaaa agggccccat ggtgccatac aaccaacagc   1020
caagtgcggt gggagtactg taagataccg tcctgtgact cctccccagt atccacggaa   1080
caattggctc ccacagcacc acctgagcta accctgtgg tccaggactg ctaccatggt   1140
gatggacaga gctaccgagg cacatcctcc accaccacca caggaaagaa gtgtcagtct   1200
tggtcatcta tgacaccaca ccggcaccag aagacccag aaaactaccc aaatgctggc   1260
ctgacaatga actactgcag gaatccagat gccgataaag gccctggtg ttttaccaca   1320 gaccccagcg tcaggtggga gtactgcaac ctgaaaaat gctcaggaac agaagcgagt   1380
gttgtagcac ctccgcctgt tgtcctgctt ccagatgtag agactccttc gaagaagac   1440 tgtatgtttg ggaatgggaa aggataccga ggcaagaggg cgaccactgt tactgggacg   1500
ccatgccagg actgggctgc ccaggagccc catagacaca gcattttcac tccagagaca   1560
aatccacggg cgggtctgga aaaaaattac tgccgtaacc ctgatggtga tgtaggtggt   1620
ccctggtgct acacgacaaa tccaagaaaa ctttacgact actgtgatgt ccctcagtgt   1680
gcggcccctt catttgattg tgggaagcct caagtggagc cgaagaaatg tcctggaagg   1740
gttgtagggg ggtgtgtggc ccacccacat tcctggccct ggcaagtcag tcttagaaca   1800
aggtttggaa tgcacttctg tggaggcacc ttgatatccc cagagtgggt gttgactgct   1860
gcccactgct tggagaagtc cccaaggcct tcatcctaca aggtcatcct gggtgcacac   1920
caagaagtga atctcgaacc gcatgttcag gaaatagaag tgtctaggct gttcttggag   1980
cccacacgaa aagatattgc cttgctaaag ctaagcagtc ctgccgtcat cactgacaaa   2040
gtaatcccag cttgtctgcc atccccaaat tatgtggtcg ctgaccggac cgaatgtttc   2100
atcactggct ggggagaaac ccaaggtact tttggagctg gccttctcaa ggaagcccag   2160
ctccctgtga ttgagaataa agtgtgcaat cgctatgagt ttctgaatgg aagagtccaa   2220
tccaccgaac tctgtgctgg gcatttggcc ggaggcactg acagttgcca gggtgacagt   2280
ggaggtcctc tggtttgctt cgagaaggac aaatacattt tacaaggagt cacttcttgg   2340
ggtcttggct gtgcacgccc caataagcct ggtgtctatg ttcgtgtttc aaggtttgtt   2400
acttggattg agggagtgat gagaaataat taa                                2433
```

<210> SEQ ID NO 4
<211> LENGTH: 810
<212> TYPE: PRT
<213> ORGANISM: Artificial sequence
<220> FEATURE:
<223> OTHER INFORMATION: amino acid sequence coding for the natural
      plasminogen(from swiss prot)with the signal peptide

<400> SEQUENCE: 4

Met Glu His Lys Glu Val Val Leu Leu Leu Leu Leu Phe Leu Lys Ser

-continued

```
1               5                   10                  15
Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
            115                 120                 125

Ser Thr Ser Pro His Arg Pro Arg Phe Ser Pro Ala Thr His Pro Ser
            130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
            195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
            275                 280                 285

Val Thr Val Ser Gly His Thr Cys Gln His Trp Ser Ala Gln Thr Pro
            290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
            355                 360                 365

Glu Leu Thr Pro Val Val Gln Asp Cys Tyr His Gly Asp Gly Gln Ser
            370                 375                 380

Tyr Arg Gly Thr Ser Ser Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430
```

Lys Gly Pro Trp Cys Phe Thr Thr Asp Pro Ser Val Arg Trp Glu Tyr
            435                 440                 445

Cys Asn Leu Lys Lys Cys Ser Gly Thr Glu Ala Ser Val Val Ala Pro
        450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 2145
<212> TYPE: DNA
<213> ORGANISM: Artificial sequence
<220> FEATURE:

<223> OTHER INFORMATION: nucleotide sequence coding for LYS77-PLG(Lys-
plasminogen)

<400> SEQUENCE: 5

| | | | | | |
|---|---|---|---|---|---|
| aaagtgtatc | tctcagagtg | caagactggg | aatggaaaga | actacagagg | gacgatgtcc | 60 |
| aaaacaaaaa | atggcatcac | ctgtcaaaaa | tggagttcca | cttctcccca | cagacctaga | 120 |
| ttctcacctg | ctacacaccc | ctcagaggga | ctggaggaga | actactgcag | gaatccagac | 180 |
| aacgatccgc | aggggccctg | gtgctatact | actgatccag | aaaagagata | tgactactgc | 240 |
| gacattcttg | agtgtgaaga | ggaatgtatg | cattgcagtg | gagaaaacta | tgacggcaaa | 300 |
| atttccaaga | ccatgtctgg | actgaatgc | caggcctggg | actctcagag | cccacacgct | 360 |
| catggataca | ttccttccaa | atttccaaac | aagaacctga | agaagaatta | ctgtcgtaac | 420 |
| cccgataggg | agctgcggcc | ttggtgtttc | accaccgacc | ccaacaagcg | ctgggaactt | 480 |
| tgtgacatcc | cccgctgcac | aacacctcca | ccatcttctg | gtcccaccta | ccagtgtctg | 540 |
| aagggaacag | gtgaaaaacta | tcgcgggaat | gtggctgtta | ccgtgtccgg | gcacacctgt | 600 |
| cagcactgga | gtgcacagac | ccctcacaca | cataacagga | caccagaaaa | cttcccctgc | 660 |
| aaaaatttgg | atgaaaacta | ctgccgcaat | cctgacggaa | aaagggcccc | atggtgccat | 720 |
| acaaccaaca | gccaagtgcg | gtgggagtac | tgtaagatac | cgtcctgtga | ctcctcccca | 780 |
| gtatccacgg | aacaattggc | tcccacagca | ccacctgagc | taaccctgt | ggtccaggac | 840 |
| tgctaccatg | gtgatggaca | gagctaccga | ggcacatcct | ccaccaccac | cacaggaaag | 900 |
| aagtgtcagt | cttggtcatc | tatgacacca | caccggcacc | agaagacccc | agaaaactac | 960 |
| ccaaatgctg | gcctgacaat | gaactactgc | aggaatccag | atgccgataa | aggcccctgg | 1020 |
| tgttttacca | cagaccccag | cgtcaggtgg | gagtactgca | acctgaaaaa | atgctcagga | 1080 |
| acagaagcga | gtgttgtagc | acctccgcct | gttgtcctgc | ttccagatgt | agagactcct | 1140 |
| tccgaagaag | actgtatgtt | tgggaatggg | aaaggatacc | gaggcaagag | ggcgaccact | 1200 |
| gttactggga | cgccatgcca | ggactgggct | gcccaggagc | cccatagaca | cagcattttc | 1260 |
| actccagaga | caaatccacg | ggcgggtctg | gaaaaaaatt | actgccgtaa | ccctgatggt | 1320 |
| gatgtaggtg | gtccctggtg | ctacacgaca | aatccaagaa | aactttacga | ctactgtgat | 1380 |
| gtccctcagt | gtgcggcccc | ttcatttgat | tgtgggaagc | ctcaagtgga | gccgaagaaa | 1440 |
| tgtcctggaa | gggttgtagg | ggggtgtgtg | gcccacccac | attcctggcc | ctggcaagtc | 1500 |
| agtcttagaa | caaggtttgg | aatgcacttc | tgtggaggca | ccttgatatc | cccagagtgg | 1560 |
| gtgttgactg | ctgcccactg | cttggagaag | tccccaaggc | cttcatccta | caaggtcatc | 1620 |
| ctgggtgcac | accaagaagt | gaatctcgaa | ccgcatgttc | aggaaataga | agtgtctagg | 1680 |
| ctgttcttgg | agcccacacg | aaaagatatt | gccttgctaa | gctaagcag | tcctgccgtc | 1740 |
| atcactgaca | aagtaatccc | agcttgtctg | ccatccccaa | attatgtggt | cgctgaccgg | 1800 |
| accgaatgtt | tcatcactgg | ctggggagaa | acccaaggta | cttttggagc | tggccttctc | 1860 |
| aaggaagccc | agctccctgt | gattgagaat | aaagtgtgca | atcgctatga | gtttctgaat | 1920 |
| ggaagagtcc | aatccaccga | actctgtgct | gggcatttgg | ccggaggcac | tgacagttgc | 1980 |
| cagggtgaca | gtggaggtcc | tctggtttgc | ttcgagaagg | acaaatacat | tttacaagga | 2040 |
| gtcacttctt | ggggtcttgg | ctgtgcacgc | cccaataagc | ctggtgtcta | tgttcgtgtt | 2100 |
| tcaaggtttg | ttacttggat | tgagggagtg | atgagaaata | attaa | | 2145 |

<210> SEQ ID NO 6

<211> LENGTH: 714
<212> TYPE: PRT
<213> ORGANISM: Artificial sequence
<220> FEATURE:
<223> OTHER INFORMATION: amino acid sequence of LYS77-PLG(Lys-plasminogen)

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
                100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
        130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
                180                 185                 190

Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
        210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
                260                 265                 270

Glu Leu Thr Pro Val Val Gln Asp Cys Tyr His Gly Asp Gly Gln Ser
            275                 280                 285

Tyr Arg Gly Thr Ser Ser Thr Thr Thr Gly Lys Lys Cys Gln Ser
        290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
                340                 345                 350

Cys Asn Leu Lys Lys Cys Ser Gly Thr Glu Ala Ser Val Val Ala Pro
            355                 360                 365

Pro Pro Val Val Leu Leu Pro Asp Val Glu Thr Pro Ser Glu Glu Asp
```

```
                370                 375                 380
Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
                420                 425                 430

Asn Tyr Cys Arg Asn Pro Asp Gly Asp Val Gly Gly Pro Trp Cys Tyr
                435                 440                 445

Thr Thr Asn Pro Arg Lys Leu Tyr Asp Tyr Cys Asp Val Pro Gln Cys
                450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
                500                 505                 510

Gly Thr Leu Ile Ser Pro Glu Trp Val Leu Thr Ala Ala His Cys Leu
                515                 520                 525

Glu Lys Ser Pro Arg Pro Ser Ser Tyr Lys Val Ile Leu Gly Ala His
                530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
                580                 585                 590

Pro Asn Tyr Val Val Ala Asp Arg Thr Glu Cys Phe Ile Thr Gly Trp
                595                 600                 605

Gly Glu Thr Gln Gly Thr Phe Gly Ala Gly Leu Leu Lys Glu Ala Gln
610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
                660                 665                 670

Lys Asp Lys Tyr Ile Leu Gln Gly Val Thr Ser Trp Gly Leu Gly Cys
                675                 680                 685

Ala Arg Pro Asn Lys Pro Gly Val Tyr Val Arg Val Ser Arg Phe Val
                690                 695                 700

Thr Trp Ile Glu Gly Val Met Arg Asn Asn
705                 710
```

<210> SEQ ID NO 7
<211> LENGTH: 1245
<212> TYPE: DNA
<213> ORGANISM: Artificial sequence
<220> FEATURE:
<223> OTHER INFORMATION: nucleotide sequence coding for delta-plg(delta-plasminogen)

<400> SEQUENCE: 7
gagcctctgg atgactatgt gaatacccag ggggcttcac tgttcagtgt cactaagaag    60
cagctgggag caggaagtat agaagaatgt gcagcaaaat gtgaggagga cgaagaattc    120

| | | |
|---|---|---|
| acctgcaggg cattccaata tcacagtaaa gagcaacaat gtgtgataat ggctgaaaac | 180 | |
| aggaagtcct ccataatcat taggatgaga gatgtagttt tatttgaaaa gaaagtgtat | 240 | |
| ctctcagagt gcaagactgg gaatggaaag aactacagag ggacgatgtc caaaacaaaa | 300 | |
| aatggcatca cctgtcaaaa atggagttcc acttctcccc acagacctag attctcacct | 360 | |
| gctacacacc cctcagaggg actggaggag aactactgca ggaatccaga caacgatccg | 420 | |
| caggggccct ggtgctatac tactgatcca gaaaagagat atgactactg cgacattctt | 480 | |
| gagtgtgaag aggcggcccc ttcatttgat tgtgggaagc ctcaagtgga gccgaagaaa | 540 | |
| tgtcctggaa gggttgtagg ggggtgtgtg gcccacccac attcctggcc ctggcaagtc | 600 | |
| agtcttagaa caaggtttgg aatgcacttc tgtggaggca ccttgatatc cccagagtgg | 660 | |
| gtgttgactg ctgcccactg cttggagaag tccccaaggc cttcatccta caaggtcatc | 720 | |
| ctgggtgcac accaagaagt gaatctcgaa ccgcatgttc aggaaataga agtgtctagg | 780 | |
| ctgttcttgg agcccacacg aaaagatatt gccttgctaa agctaagcag tcctgccgtc | 840 | |
| atcactgaca aagtaatccc agcttgtctg ccatccccaa attatgtggt cgctgaccgg | 900 | |
| accgaatgtt tcatcactgg ctggggagaa acccaaggta cttttggagc tggccttctc | 960 | |
| aaggaagccc agctccctgt gattgagaat aaagtgtgca atcgctatga gtttctgaat | 1020 | |
| ggaagagtcc aatccaccga actctgtgct gggcatttgg ccggaggcac tgacagttgc | 1080 | |
| cagggtgaca gtggaggtcc tctggtttgc ttcgagaagg acaaatacat tttacaagga | 1140 | |
| gtcacttctt ggggtcttgg ctgtgcacgc cccaataagc ctggtgtcta tgttcgtgtt | 1200 | |
| tcaaggtttg ttacttggat tgagggagtg atgagaaata attaa | 1245 | |

```
<210> SEQ ID NO 8
<211> LENGTH: 414
<212> TYPE: PRT
<213> ORGANISM: Artificial sequence
<220> FEATURE:
<223> OTHER INFORMATION: amino acid sequence of delta-plg(delta-
      plasminogen)

<400> SEQUENCE: 8
```

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Cys Val Ala His
            180                 185                 190

Pro His Ser Trp Pro Trp Gln Val Ser Leu Arg Thr Arg Phe Gly Met
            195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
            260                 265                 270

Leu Lys Leu Ser Ser Pro Ala Val Ile Thr Asp Lys Val Ile Pro Ala
            275                 280                 285

Cys Leu Pro Ser Pro Asn Tyr Val Val Ala Asp Arg Thr Glu Cys Phe
    290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
            340                 345                 350

Leu Ala Gly Gly Thr Asp Ser Cys Gln Gly Asp Ser Gly Gly Pro Leu
            355                 360                 365

Val Cys Phe Glu Lys Asp Lys Tyr Ile Leu Gln Gly Val Thr Ser Trp
    370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410

<210> SEQ ID NO 9
<211> LENGTH: 1104
<212> TYPE: DNA
<213> ORGANISM: Artificial sequence
<220> FEATURE:
<223> OTHER INFORMATION: nucleotide sequence coding for Mini-plg(mini-
      plasminogen)

<400> SEQUENCE: 9
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt    120
gggaatggga aggataccg aggcaagagg gcgaccactg ttactgggac gccatgccag      180
gactgggctg cccaggagcc ccatagacac agcattttca ctccagagac aaatccacgg    240
gcgggtctgg aaaaaaatta ctgccgtaac cctgatggtg atgtaggtgg tccctggtgc    300
tacacgacaa atccaagaaa actttacgac tactgtgatg tccctcagtg tgcggccct     360 tcatttgatt gtgggaagcc tcaagtggag ccgaagaaat gtcctggaag ggttgtaggg    420
gggtgtgtgg cccacccaca ttcctggccc tggcaagtca gtcttagaac aaggtttgga    480
atgcacttct gtgaggcac cttgatatcc ccagagtggg tgttgactgc tgcccactgc    540
ttggagaagt ccccaaggcc ttcatcctac aaggtcatcc tgggtgcaca ccaagaagtg    600

```
aatctcgaac cgcatgttca ggaaatagaa gtgtctaggc tgttcttgga gcccacacga    660
aaagatattg ccttgctaaa gctaagcagt cctgccgtca tcactgacaa agtaatccca    720
gcttgtctgc catccccaaa ttatgtggtc gctgaccgga ccgaatgttt catcactggc    780
tggggagaaa cccaaggtac ttttggagct ggccttctca aggaagccca gctccctgtg    840
attgagaata aagtgtgcaa tcgctatgag tttctgaatg gaagagtcca atccaccgaa    900
ctctgtgctg gcatttggc cggaggcact gacagttgcc agggtgacag tggaggtcct    960
ctggtttgct tcgagaagga caaatacatt ttacaaggag tcacttcttg gggtcttggc   1020
tgtgcacgcc ccaataagcc tggtgtctat gttcgtgttt caaggtttgt tacttggatt   1080
gagggagtga tgagaaataa ttaa                                          1104
```

<210> SEQ ID NO 10
<211> LENGTH: 367
<212> TYPE: PRT
<213> ORGANISM: Artificial sequence
<220> FEATURE:
<223> OTHER INFORMATION: amino acid sequence of Mini-plg(mini-
      plasminogen)

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
    130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
        195                 200                 205

Ile Glu Val Ser Arg Leu Phe Leu Glu Pro Thr Arg Lys Asp Ile Ala
    210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
```

```
              260               265               270
Leu Lys Glu Ala Gln Leu Pro Val Ile Glu Asn Lys Val Cys Asn Arg
            275               280               285

Tyr Glu Phe Leu Asn Gly Arg Val Gln Ser Thr Glu Leu Cys Ala Gly
            290               295               300

His Leu Ala Gly Gly Thr Asp Ser Cys Gln Gly Asp Ser Gly Gly Pro
305               310               315               320

Leu Val Cys Phe Glu Lys Asp Lys Tyr Ile Leu Gln Gly Val Thr Ser
            325               330               335

Trp Gly Leu Gly Cys Ala Arg Pro Asn Lys Pro Gly Val Tyr Val Arg
            340               345               350

Val Ser Arg Phe Val Thr Trp Ile Glu Gly Val Met Arg Asn Asn
            355               360               365

<210> SEQ ID NO 11
<211> LENGTH: 750
<212> TYPE: DNA
<213> ORGANISM: Artificial sequence
<220> FEATURE:
<223> OTHER INFORMATION: nucleotide sequence coding for Micro-plg(micro-
      plasminogen)

<400> SEQUENCE: 11
gccccttcat tgattgtgg gaagcctcaa gtggagccga agaaatgtcc tggaagggtt      60
gtaggggggt gtgtggccca cccacattcc tggccctggc aagtcagtct tagaacaagg   120
tttggaatgc acttctgtgg aggcaccttg atatccccag agtgggtgtt gactgctgcc   180
cactgcttgg agaagtcccc aaggccttca tcctacaagg tcatcctggg tgcacaccaa   240
gaagtgaatc tcgaaccgca tgttcaggaa atagaagtgt ctaggctgtt cttggagccc   300
acacgaaaag atattgcctt gctaaagcta agcagtcctg ccgtcatcac tgacaaagta   360
atcccagctt gtctgccatc cccaaattat gtggtcgctg accggaccga atgtttcatc   420
actggctggg gagaaaccca aggtactttt ggagctggcc ttctcaagga agcccagctc   480
cctgtgattg agaataaagt gtgcaatcgc tatgagtttc tgaatggaag agtccaatcc   540
accgaactct gtgctgggca tttggccgga ggcactgaca gttgccaggg tgacagtgga   600
ggtcctctgg tttgcttcga gaaggacaaa tacattttac aaggagtcac ttcttggggt   660
cttggctgtg cacgccccaa taagcctggt gtctatgttc gtgtttcaag gtttgttact   720
tggattgagg gagtgatgag aaataattaa                                      750

<210> SEQ ID NO 12
<211> LENGTH: 249
<212> TYPE: PRT
<213> ORGANISM: Artificial sequence
<220> FEATURE:
<223> OTHER INFORMATION: amino acid sequence coding for Micro-plg(micro-
      plasminogen)

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60
```

Lys Ser Pro Arg Pro Ser Ser Tyr Lys Val Ile Leu Gly Ala His Gln
65                  70                  75                  80

Glu Val Asn Leu Glu Pro His Val Gln Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
                115                 120                 125

Asn Tyr Val Val Ala Asp Arg Thr Glu Cys Phe Ile Thr Gly Trp Gly
130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 684
<212> TYPE: DNA
<213> ORGANISM: Artificial sequence
<220> FEATURE:
<223> OTHER INFORMATION: nucleotide sequence coding for the serine
      protease domain

<400> SEQUENCE: 13
gttgtagggg ggtgtgtggc ccacccacat tcctggccct ggcaagtcag tcttagaaca    60
aggtttggaa tgcacttctg tggaggcacc ttgatatccc cagagtgggt gttgactgct   120
gcccactgct tggagaagtc cccaaggcct tcatcctaca aggtcatcct gggtgcacac   180
caagaagtga atctcgaacc gcatgttcag gaaatagaag tgtctaggct gttcttggag   240
cccacacgaa aagatattgc cttgctaaag ctaagcagtc ctgccgtcat cactgacaaa   300
gtaatcccag cttgtctgcc atccccaaat tatgtggtcg ctgaccggac cgaatgtttc   360
atcactggct ggggagaaac ccaaggtact tttggagctg gccttctcaa ggaagcccag   420
ctccctgtga ttgagaataa agtgtgcaat cgctatgagt ttctgaatgg aagagtccaa   480
tccaccgaac tctgtgctgg gcatttggcc ggaggcactg acagttgcca gggtgacagt   540
ggaggtcctc tggtttgctt cgagaaggac aaatacattt tacaaggagt cacttcttgg   600
ggtcttggct gtgcacgccc caataagcct ggtgtctatg ttcgtgtttc aaggtttgtt   660
acttggattg agggagtgat gaga                                         684

<210> SEQ ID NO 14
<211> LENGTH: 228
<212> TYPE: PRT
<213> ORGANISM: Artificial sequence
<220> FEATURE:
<223> OTHER INFORMATION: amino acid sequence coding for the serine

```
    protease domain

<400> SEQUENCE: 14

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
                100                 105                 110

Val Ala Asp Arg Thr Glu Cys Phe Ile Thr Gly Trp Gly Glu Thr Gln
            115                 120                 125

Gly Thr Phe Gly Ala Gly Leu Leu Lys Glu Ala Gln Leu Pro Val Ile
        130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg
225
```